US012692306B2

(12) United States Patent
Boyman et al.

(10) Patent No.: US 12,692,306 B2
(45) Date of Patent: Jul. 28, 2026

(54) CD25-BIASED ANTI-IL-2 ANTIBODY

(71) Applicant: UNIVERSITÄT ZÜRICH, Zürich (CH)

(72) Inventors: Onur Boyman, Küsnacht (CH); Ufuk Karakus, Zurich (CH); Miro Raeber, Zurich (CH); Roman Meledin, Dübendorf (CH); Robert Maka, Zurich (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 711 days.

(21) Appl. No.: 18/042,213

(22) PCT Filed: Aug. 18, 2021

(86) PCT No.: PCT/EP2021/072960
§ 371 (c)(1),
(2) Date: Feb. 19, 2023

(87) PCT Pub. No.: WO2022/038193
PCT Pub. Date: Feb. 24, 2022

(65) Prior Publication Data
US 2023/0303680 A1 Sep. 28, 2023

(30) Foreign Application Priority Data

| | | | |
|---|---|---|---|
| Aug. 18, 2020 | (EP) | .................................... | 20191635 |
| Aug. 18, 2020 | (EP) | .................................... | 20191638 |
| Sep. 11, 2020 | (EP) | .................................... | 20195863 |

(51) Int. Cl.
*C07K 16/24* (2006.01)
*A61P 37/02* (2006.01)

(52) U.S. Cl.
CPC ............ *C07K 16/246* (2013.01); *A61P 37/02* (2018.01); *C07K 2317/565* (2013.01); *C07K 2317/92* (2013.01)

(58) Field of Classification Search
None
See application file for complete search history.

(56) References Cited

FOREIGN PATENT DOCUMENTS

| | | | | |
|---|---|---|---|---|
| CN | 108884157 | 11/2018 | | |
| CN | 110642934 | 1/2020 | | |
| WO | WO-2016005950 A1 * | 1/2016 | .............. | A61P 35/00 |
| WO | 2017/070561 | 4/2017 | | |
| WO | WO-2017122130 A1 * | 7/2017 | .......... | C07K 16/246 |
| WO | WO-2018217058 A1 * | 11/2018 | .............. | A61P 35/00 |
| WO | 2019/246404 | 12/2019 | | |

OTHER PUBLICATIONS

Janeway et al., Immunobiology, 3rd edition, Garland Publishing Inc., 1997, pp. 3:1-3:11.*
Rudikoff et al., Proc Natl Acad Sci U S A. Mar. 1982;79(6):1979-83. doi: 10.1073/pnas.79.6.1979. PMID: 6804947.*
Edwards et al., J Mol Biol. Nov. 14, 2003;334(1):103-18. doi: 10.1016/j.jmb.2003.09.054. PMID: 14596803.*
Llyod et al., Protein Eng Des Sel. Mar. 2009;22(3):159-68. doi: 10.1093/protein/gzn058. Epub Oct. 29, 2008. PMID: 18974080.*
Goel et al., J Immunol. Dec. 15, 2004; 173(12):7358-67 PMID: 15585860 DOI: 10.4049/jimmunol.173.12.7358.*
Lescar et al., J Biol Chem. Jul. 28, 1995;270(30):18067-76. doi: 10.1074/jbc.270.30.18067. PMID: 7629116.*
Kanyavuz et al., Nat Rev Immunol. Jun. 2019;19(6):355-368. doi: 10.1038/S41577-019-0126-7. PMID: 30718829.*
Zheng et al., Front Immunol. Jun. 9, 2021:12:586078. doi: 10.3389/fimmu.2021.586078. eCollection 2021. PMID: 34177881 PMCID: PMC8220221.*
Raeber et al., EBioMedicine. Apr. 2023:90:104539. doi: 10.1016/j.ebiom.2023.104539. Epub Mar. 31, 2023. PMID: 37004361 PM-CID : PMC10111960.*
Kipriyanov et al., Mol Biotechnol. Sep. 1999;12(2):173-201. doi: 10.1385/MB:12:2:173. PMID: 10596374.*
Mevissen M L C M et al: "Identification of structural differences between different forms of interleukin-2 (IL-2) using anti-(human recombinant) IL-2 monoclonal antibodies", Cytokine, Academic Press Ltd, Philadelphia, PA, US, vol. 3, No. 1, Jan. 1, 1991 (Jan. 1, 1991).
Onur Boyman et al: "The role of interleukin-2 during homeostasis and activation of the immune system", Nature Reviews Immunology, vol. 12, No. 3, Mar. 1, 2012 (Mar. 1, 2012), pp. 180-190.
Arenas-Ramirez Natalia et al: "Interleukin-2: Biology, Design and Application", Trends in Immunology, Elsevier Ltd. * Trends Journals, GB, vol. 36, No. 12, Nov. 10, 2015 (Nov. 10, 2015), pp. 763-777.
Trotta Eleonora et al: "A human anti-IL-2 antibody that potentiates regulatory T cells by a structure-based mechanism", Nature Medicine, Nature Pub. Co, New York, vol. 24, No. 7, Jun. 25, 2018 (Jun. 25, 2018), pp. 1005-1014.
Boyman Onur et al: "Potential use of IL-2/anti-IL-2 antibody immune complexes for the treatment of cancer and autoimmune disease", Expert Opinion on Biological Therapy, Informa Healthcare, vol. 6, No. 12, Dec. 1, 2006 (Dec. 1, 2006), pp. 1323-1331.

* cited by examiner

*Primary Examiner* — Michael Szperka
(74) *Attorney, Agent, or Firm* — JMB Davis Ben-David

(57) ABSTRACT

The invention provides a human IL-2 (hIL-2)-specific monoclonal antibody, wherein a complex of hIL-2 and the monoclonal induces IL-2 signalling preferentially via CD25 and the trimeric IL-2R. The invention further provides a pharmaceutical composition comprising hIL-2 and said hIL-2-mAb for use treating inflammatory disease.

11 Claims, 28 Drawing Sheets
Specification includes a Sequence Listing.

Fig. 3
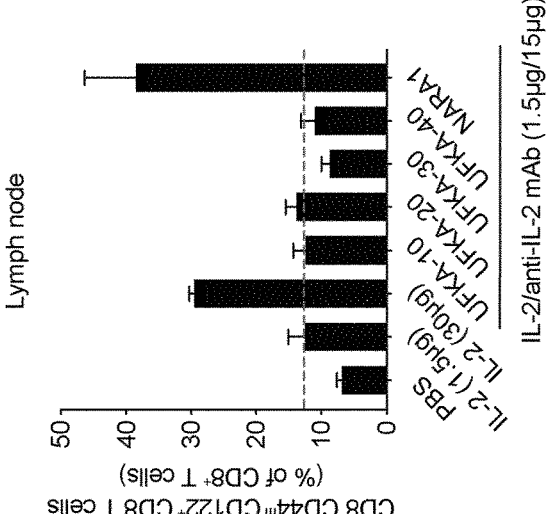
A
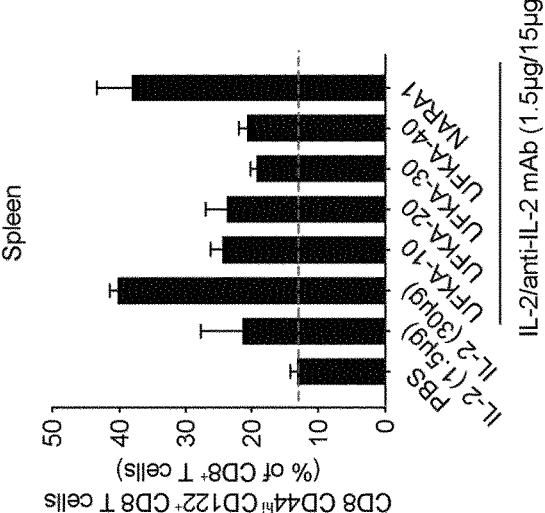
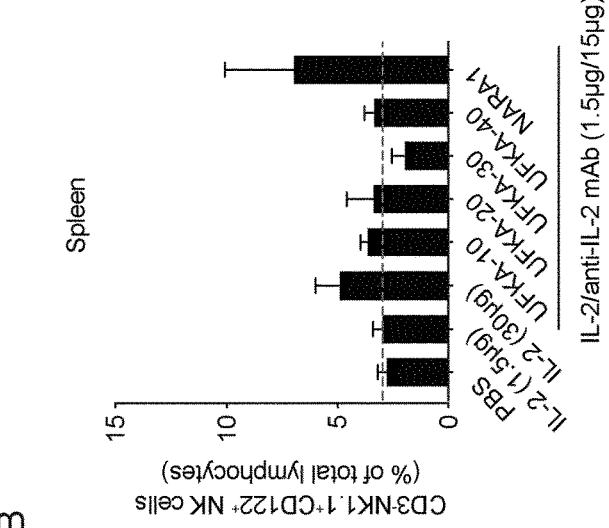
B

C

Fig. 8 (continued)
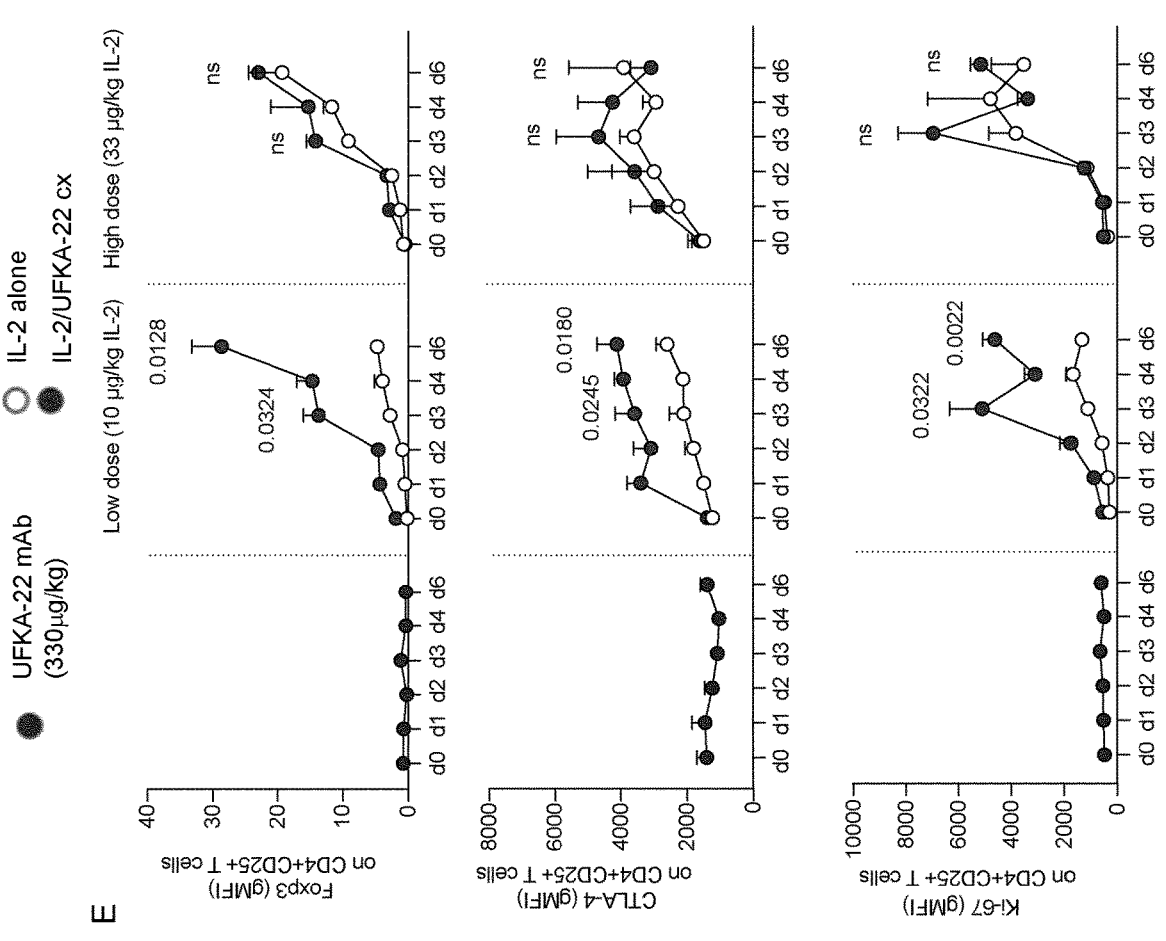
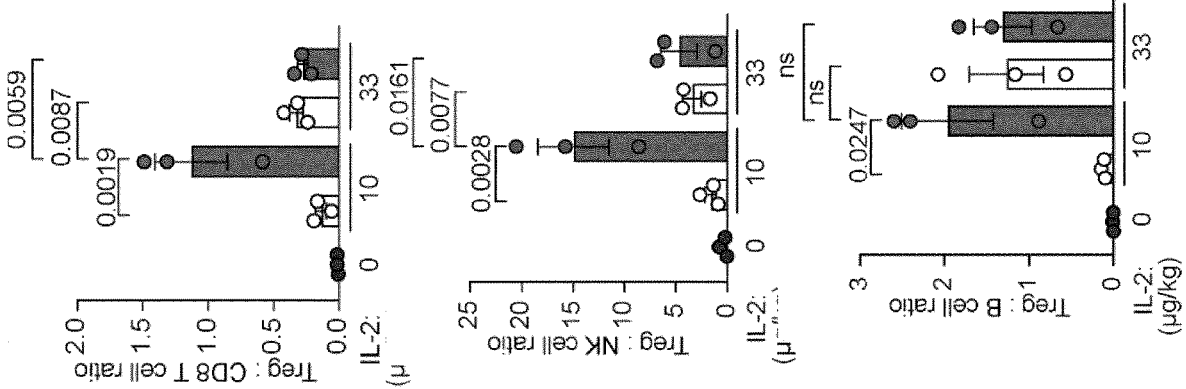

Buried surface area (BSA)

Fig. 10 (continued)

| Group | Residue | CD25 | CD122 | CD132 | UFKA20-00 | F5111 | NARA1 |
|---|---|---|---|---|---|---|---|
| B | LEU 53 | | | | | | |
| | LYS 54 | | | | | | |
| | HIS 55 | | | | | | |
| | LEU 56 | | | | | | |
| | GLN 57 | | | | Q57 16.85 | | |
| | CYS 58 | | | | | | |
| | LEU 59 | | | | | | |
| | GLU 60 | | | | E60 38.30 | | |
| | GLU 61 | E61 54.67 | | | E61 42.49 | | |
| | GLU 62 | E62 14.40 | | | | | |
| | LEU 63 | | | | L63 8.37 | | |
| B' | LYS 64 | K64 9.88 | | | K64 104.33 | | |
| | PRO 65 | P65 42.21 | | | | | |
| | LEU 66 | | | | | | |
| | GLU 67 | | | | E67 5.25 | | |
| | GLU 68 | E68 80.95 | | | E68 8.62 | | E68 8.41 |
| | VAL 69 | V69 5.35 | | | | | |
| | LEU 70 | | | | | | |
| | ASN 71 | | | | | N71 9.00 | N71 14.14 |
| | LEU 72 | L72 54.41 | | | | | L72 53.39 |
| | ALA 73 | | | | | | |
| | GLN 74 | | | | | Q74 12.00 | Q74 67.37 |
| | SER 75 | | | | | S75 8.00 | S75 10.94 |
| | LYS 76 | | | | | K76 149.00 | K76 120.02 |
| | ASN 77 | | | | | N 77 54.00 | N 77 26.89 |
| | PHE 78 | | | | | F78 6.00 | |
| | HIS 79 | | | | H79 0.98 | H79 110.00 | |
| | LEU 80 | | | | L80 46.55 | L80 17.00 | |
| C | ARG 81 | | R81 51.07 | | R81 57.63 | R81 149.00 | |
| | PRO 82 | | | | | P82 8.00 | |
| | ARG 83 | | | | R83 118.35 | R83 10.00 | |
| | ASP 84 | | D84 57.09 | | D84 62.84 | D84 49.00 | |
| | LEU 85 | | | | L85 2.84 | L85 15.00 | |
| | ILE 86 | | | | I86 10.20 | | |
| | SER 87 | | S87 16.04 | | S87 62.25 | | |
| | ASN 88 | | N88 61.85 | | N88 36.47 | N88 52.00 | |
| | ILE 89 | | | | | | |
| | ASN 90 | | | | N90 49.22 | | |
| | VAL 91 | | V91 85.45 | | V91 75.24 | | |
| | ILE 92 | | I92 34.48 | | I92 0.84 | | |
| | VAL 93 | | | | | | |
| | LEU 94 | | | | L94 56.19 | | |
| | GLU 95 | | E95 44.91 | | E95 10.18 | | |
| | LEU 96 | | | | | | |
| | LYS 97 | | | | K97 16.57 | | |
| | GLY 98 | | | | | | |
| | SER 99 | | | | | | |
| | GLU 100 | | | | | | |
| | THR 101 | | | | T101 59.92 | | |
| | THR 102 | | | | T102 11.80 | | |
| | PHE 103 | | | | F103 0.98 | | |
| | MET 104 | | | | M104 62.40 | | |

0  50  100  150

Buried surface area (BSA)

Fig. 10 (continued)

| | CD25 | CD122 | CD132 | UFKA20-00 | F5111 | NARA1 |
|---|---|---|---|---|---|---|
| CYS 105 | C105 10.78 | | | | | |
| GLU 106 | E106 21.41 | | | | | |
| TYR 107 | T107 33.74 | | | | | |
| ALA 108 | A108 3.31 | | | | | |
| ASP 109 | D109 20.71 | | | | | |
| GLU 110 | | | E110 26.47 | | | |
| THR 111 | | | | | | |
| ALA 112 | | | | | | |
| THR 113 | | | | | | |
| ILE 114 | | | | | | |
| VAL 115 | | | | | | |
| GLU 116 | | | | | | |
| PHE 117 | | | | | | |
| LEU 118 | | | | | | |
| ASN 119 | | | N119 27.97 | | | |
| ARG 120 | | | R120 4.79 | | | |
| TRP 121 | | | | | | |
| ILE 122 | | | | | | |
| THR 123 | | | T123 59.37 | | | |
| PHE 124 | | | | | | |
| CYS 125 | | | | | | |
| GLN 126 | | | Q126 82.64 | | | |
| SER 127 | | | S127 31.70 | | | |
| ILE 128 | | | | | | |
| ILE 129 | | | I129 40.05 | | | |
| SER 130 | | | S130 54.65 | | | |
| THR 131 | | | T131 0.34 | | | |
| LEU 132 | | | | | | |
| THR 133 | | | T133 29.49 | | | |

0    50    100    150

Buried surface area (BSA)

Fig. 11
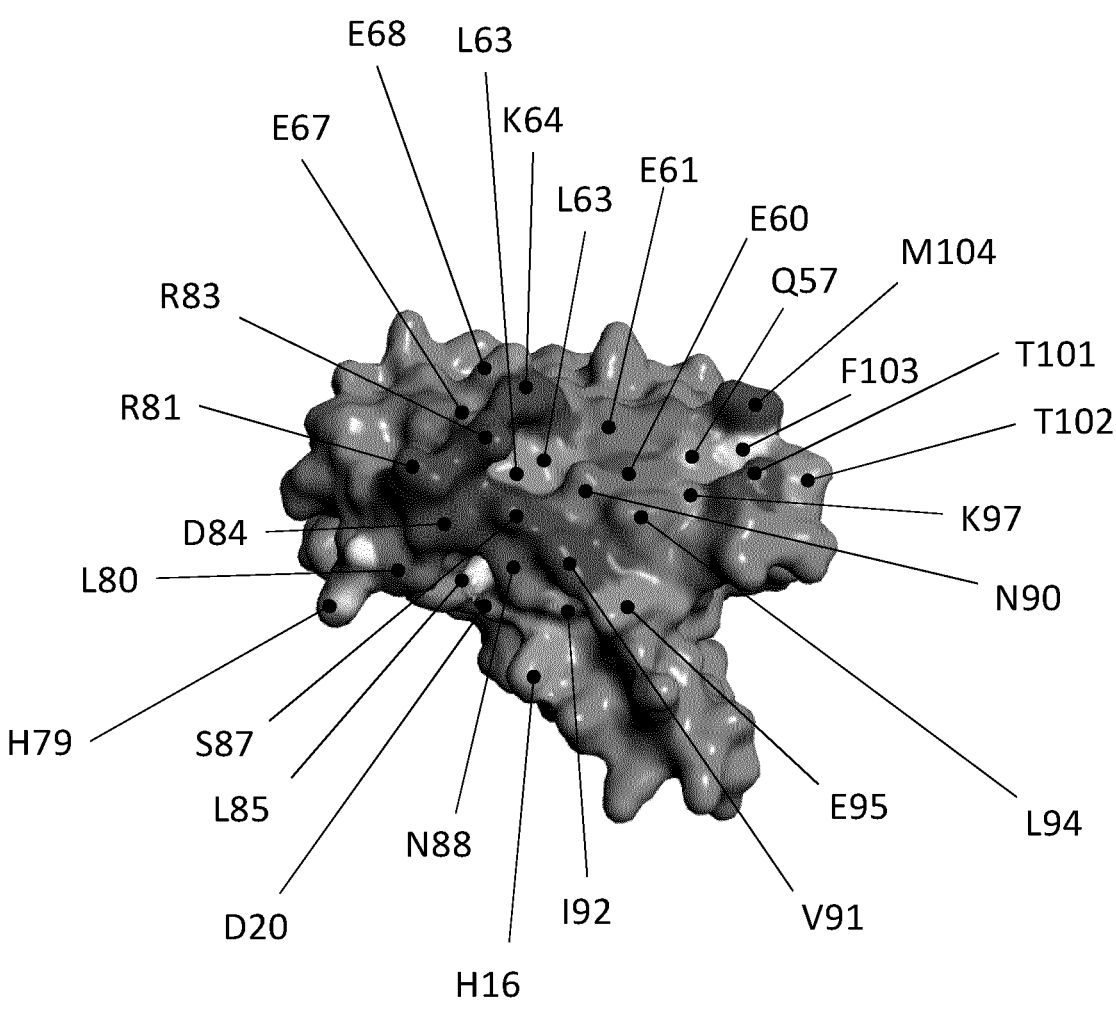
Buried Surface Area
 < 5
>5; <20
>20; <50
>50

E
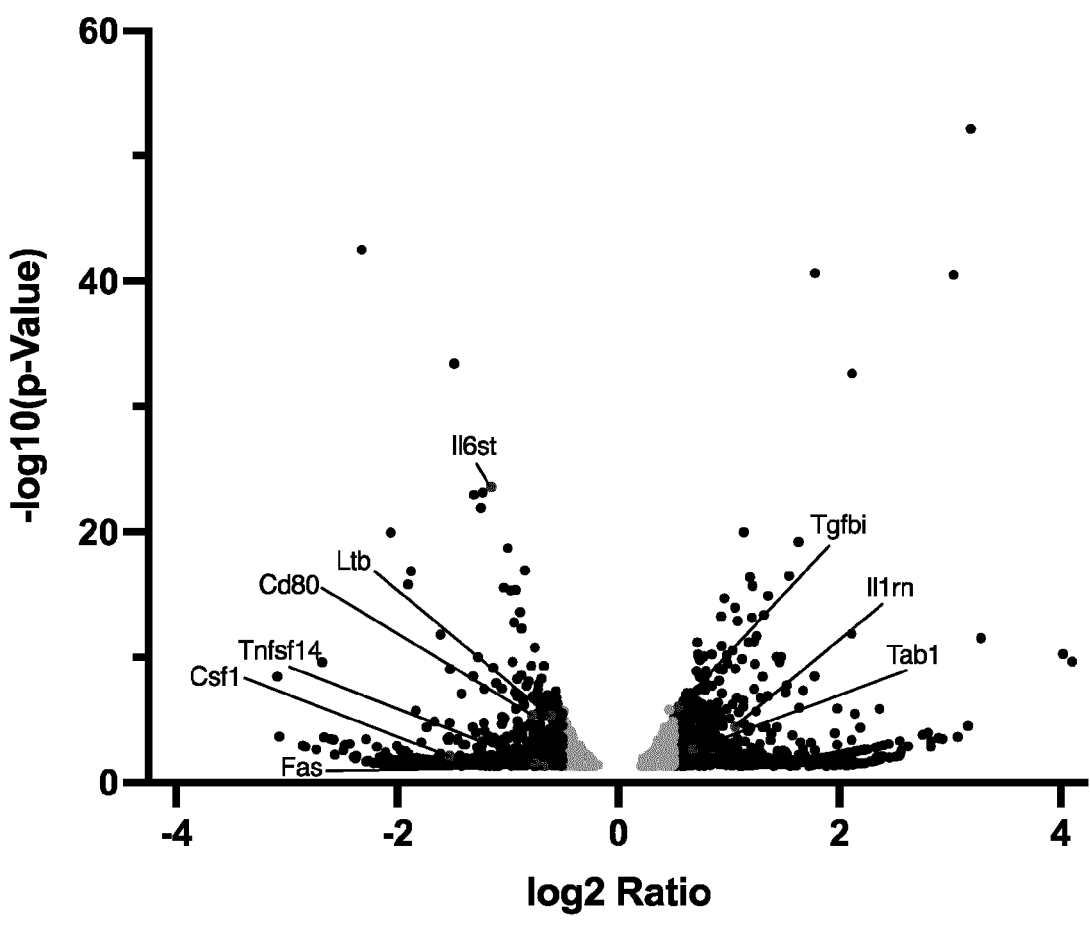

CD25-BIASED ANTI-IL-2 ANTIBODY

CROSS-REFERENCE TO RELATED APPLICATIONS

This is the U.S. National Stage of International Patent Application No. PCT/EP2021/072960 filed on Aug. 18, 2021, which claims priority to European Patent Application No. 20191635.0 filed on Aug. 18, 2020; European Patent Application No. 20191638.4 filed on Aug. 18, 2020; and European Patent Application No. 20195863.4 filed on Sep. 11, 2020.

INCORPORATION BY REFERENCE OF SEQUENCE LISTING

The Sequence Listing submitted as part of International Patent Application No. PCT/EP2021/072960, which is about 29,000 Bytes, is incorporated by reference herein in its entirety.

The present invention relates to an antibody specifically reactive to human IL-2 that is capable of biasing the IL-2's effect towards a tolerogenic, CD25-mediated immune reaction instead of towards a CD122-mediated immune reaction. The invention further provides specific pharmaceutical compositions and treatments using the invention's antibody.

BACKGROUND OF THE INVENTION

Interleukin-2 (IL-2) is a 15.5 kDa, four-$\alpha$-helix-bundle cytokine and a crucial T cell growth factor, which signals through specific IL-2 receptors (IL-2Rs). IL-2-IL-2R engagement initiates downstream signalling pathways, including the Janus kinase-signal transducer and activator of transcription (STAT), phosphoinositide 3-kinase (PI3K)—AKT, and mitogen-activated protein kinase (MAPK) pathway (Arenas-Ramirez, *Trends Immunol.* 2015, 36:763). There are two types of IL-2Rs able to signal, the dimeric and trimeric IL-2Rs (Ross, *Annu. Rev. Immunol.* 2018, 36:411). Dimeric IL-2Rs are made of IL-2RB (CD122) and the common gamma chain ($\gamma$c; CD132) and display an intermediate affinity to IL-2 (dissociation constant $[K_d] \approx 10^{-9}$ M); trimeric IL-2Rs consist of CD122, CD132, and IL-2Ra (CD25), with CD25 serving to further increase the IL-2R's affinity by 100-fold, which is why trimeric IL-2Rs ($K_d \approx 10^{-11}$ M) are also referred to as high-affinity IL-2Rs (Arenas-Ramirez, 2015). As a consequence, cells that robustly express high levels of trimeric IL-2Rs, such as forkhead box p3 (Foxp3)$^+$CD25$^{high}$ CD4$^+$ regulatory T ($T_{reg}$) cells, have a competitive advantage over CD25-cells, provided both cells subsets show similar expression of CD122 and CD132. However, complicating IL-2 immunotherapy, CD4+$T_{reg}$ cells carry high levels of CD25 but only low to intermediate levels of CD122, whereas antigen-experienced (memory) CD8$^+$ T cells and natural killer (NK) cells express high levels of CD122 but only background levels of CD25 at steady state. Thus, CD4$^+T_{reg}$ cells, CD8$^+$ T cells and NK cells can compete for IL-2 during IL-2 immunotherapy (Arenas-Ramirez, *Sci. Transl. Med.* 2016, 8:367; Raeber, *Immunol. Rev.* 2018, 283:176).

The pleiotropic action of IL-2 on both immunosuppressive $T_{reg}$ cells and immunostimulatory effector immune cells makes its therapeutic use challenging. Multiple approaches have been pursued to improve IL-2's therapeutic properties. IL-2 can be biased to the dimeric or trimeric IL-2R by introducing mutations into IL-2 (also termed IL-2 muteins), by PEGylating IL-2 at specific sites, or by using IL-2/anti- IL-2 monoclonal antibody (mAb) complexes (briefly, IL-2cx). The anti-mouse IL-2 specific mAb clone JES6-1 was the prototypic antibody developed for this purpose. Complexing recombinant wild-type (WT) mouse IL-2 with JES6-1 results in IL-2/JES6-1cx, which vigorously stimulate CD25$^{high}$ $T_{reg}$ cells in vivo, whereas resting CD8$^+$ T cells and NK cells are barely affected by these IL-2cx (Boyman, *Science* 2006, 311:1924; Letourneau, PNAS 2010, 107: 2171). Due to their in vivo effects, IL-2/JES6-1cx and similar IL-2cx are called CD25-directed or CD25-biased IL-2cx.

CD25-biased IL-2cx have been assessed in multiple models of solid allograft transplantation as well as chronic-inflammatory and autoimmune diseases, including autoimmune diabetes, experimental autoimmune encephalomyelitis (a model of multiple sclerosis), collagen-induced arthritis, inflammatory colitis, and systemic lupus erythematosus-like syndrome in mice (Tang, *Immunity* 2008, 28:687; Webster, *J. Exp. Med.* 2009, 206:751; Lee, *Immunol.* 2012, 137:305; Spangler, *Immunity* 2015, 42:815; Yan, *Kidney Int.* 2017, 91:603). The receptor bias function of IL-2cx was thought to be achieved by a mAb eclipsing the IL-2 binding site of either the high affinity, or intermediate affinity receptor. Structural analysis of the IL-2/JES6-1cx suggested that JES6-1 sterically interfered with IL-2 binding to CD132 and additionally caused mild allosteric changes in the IL-2 structure to affect the interaction of IL-2 with CD25 (Spangler, *Immunity,* 2015). Conversely, in the CD25-biased human IL-2cx made of the anti-human IL-2 mAb F5111.2, the epitopes covered by F5111.2 belonged to the CD122-binding site and induced mild allosteric changes in the CD25 epitope (Trotta, *Nat. Med.* 2018, 24:1005). It is not known whether a CD25-biasing anti-IL-2 mAb has to dissociate from the IL-2cx once IL-2 has bound to CD25, for IL-2 to bind to the CD122-CD132 dimer and initiate signalling.

Based on the above-mentioned state of the art, the objective of the present invention is to provide improved means and methods to bias IL-2 signals towards the high affinity IL-2 receptor, particularly expressed on T$^{reg}$, to inhibit inflammation. This objective is attained by the subject-matter of the independent claims of the present specification.

SUMMARY OF THE INVENTION

Drawing on the results of a novel cell-based in vitro screening method allowing the selection of IL-2cx-forming IL-2 antibodies based on their binding to CD25 and subsequent delivery of IL-2 to CD122-CD132 dimeric IL-2Rs, the invention provides an anti-human IL-2 (hIL-2) mAb which is particularly efficient in delivering IL-2 to cells expressing a high abundance of CD25 (also termed IL-2R$\alpha$); these cell must also carry CD122 (also called IL-2R$\beta$) and CD132 (also termed IL-2R$\gamma$) in order to initiate intracellular signalling pathways. Administration of human IL-2 in complex with a human interleukin-2 (hIL-2)-specific monoclonal antibody (mAb) results in preferential expansion of $T_{reg}$ cells in vivo in mice and in macaques.

A first aspect of the invention is an anti-hIL-2 mAb, or antibody fragment, specific for an epitope comprising defined amino acid residues of the hIL-2 molecule, while leaving other residues uncovered. In particular embodiments, the binding of anti-hIL-2 mAb to hIL-2 is characterised by a dissociation constant $(K_D) \leq 5.51 \times 10^{-9}$, particularly $\leq 5.13 \times 10^{-9}$, an on-rate $(K_{on}) \geq 4.12 \times 10^5$ Lmol$^{-1}$s$^{-1}$, particularly $\geq 4.66 \times 10^5$ Lmol$^{-1}$s$^{-1}$ and an off-rate $(K_{off})$ $\leq 2.83 \times 10^{-3}$ s$^{-1}$, particularly $\leq 2.39 \times 10^{-3}$ s$^{-1}$, or a complex of the anti-hIL-2 mAb according to the invention with hIL-2 binds preferentially to CD25 compared to CD122, and the anti-hIL-2 mAb dissociates from IL-2 when the complex interacts with a cell expressing high abundance of CD25 in addition to expressing CD122 and CD132. These characteristics provide an anti-hIL-2 mAb, that when associated with hIL-2, forms a complex which binds to IL-2R$\alpha^+$+T$_{regs}$ with an EC50 of 0.154 ng/ml, while binding IL-2R$\beta^+$+CD8$^+$+ CD44$^{hi}$ CD122$^+$+T cells with an EC50 of 442.9 ng/ml.

Another aspect of the invention is an anti-hIL-2 mAb, particularly bearing characteristics according to the first aspect of the invention, with a heavy chain variable (V$_H$) region comprising a V$_H$ complementarity determining region CDR$_H$1, CDR$_H$2 and CDR$_H$3, and a variable light chain (V$_L$) region comprising a V$_L$ complementarity determining region CDR$_L$1, CDR$_L$2 and CDR$_L$3, and wherein the CDR$_H$1, CDR$_H$2, CDR$_H$3, CDR$_L$1, CDR$_L$2 and CDR$_L$3 comprise, or are identical to SEQ ID NO 001, SEQ ID NO 002, SEQ ID NO 003, SEQ ID NO 004, SEQ ID NO 005, and SEQ ID NO 006 respectively. In some embodiments the CDR are included in a V$_H$ sequence of SEQ NO ID 007, and a V$_L$ sequence of SEQ ID NO 015, or certain functionally similar sequences.

Another aspect of the invention is a hIL-2 fusion protein comprising a hIL-2 protein domain, and an anti-hIL-2 mAb domain joined by a peptide linker, particularly a peptide linker about 30 amino acids in length.

Further aspects provide a nucleic acid molecule encoding the anti-hIL-2 mAb, or antibody fragment thereof, or hIL-2 fusion protein according to the invention, or a vector comprising said nucleic acid molecule, or a cell, or hybridoma line comprising, or capable of producing the anti-hIL-2 mAb, or fusion protein according to the invention.

An additional aspect of the invention relates to a pharmaceutical composition comprising the hIL-2-specific mAb, or antigen-binding fragment together with hIL-2, optionally non-covalently associated, for use as a medicament, particularly to treat immune inflammation such as allograft-related disorders, chronic inflammation, allergy or autoimmunity. The pharmaceutical composition comprising the anti-hIL-2 mAb may also comprise an additional immunosuppressant drug, or a pharmaceutically acceptable carrier.

Another, distinct aspect of the invention is a pharmaceutical composition for use in a patient with a condition benefiting from enhanced dendritic cell (DC) function, comprising an IL-2 complex. Said IL-2 complex comprises both a human IL-2 (hIL-2) polypeptide, and a hIL-2-specific monoclonal antibody (mAb). An example of an appropriate hIL-2-specific mAb is disclosed in US20170114130A1, the contents of which are incorporated herein by reference, or a hIL-2-specific mAb according to any one of the aspects and embodiments provided above. The IL-2 complex according to this aspect of the invention preferentially binds to CD25, and/or the high-affinity IL-2 receptor comprising CD122, CD132 and CD25, compared to the intermediate-affinity IL-2R comprising CD122 and CD132.

DETAILED DESCRIPTION OF THE INVENTION

Terms and Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry).

Standard techniques are used for molecular, genetic and biochemical methods (see generally, Sambrook et al., Molecular Cloning: A Laboratory Manual, 4th ed. (2012) Cold Spring Harbor Laboratory Press, Cold Spring Harbor, N.Y. and Ausubel et al., Short Protocols in Molecular Biology (2002) 5th Ed, John Wiley & Sons, Inc.) and chemical methods.

In the present specification, the term positive, when used in the context of expression of a marker, refers to expression of an antigen assayed by a fluorescently labelled antibody, wherein the label's fluorescence on the structure (for example, a cell) referred to as "positive" is at least 30% higher ($\geq$30%), particularly $\geq$50% or $\geq$80%, in median fluorescence intensity in comparison to staining with an isotype-matched fluorescently labelled antibody which does not specifically bind to the same target. Such expression of a marker is indicated by a superscript "plus" (+), following the name of the marker, e.g. CD25$^+$.

In the present specification, the term negative, when used in the context of expression of a marker, refers to expression of an antigen assayed by a fluorescently labelled antibody, wherein the median fluorescence intensity is less than 30% higher, particularly less than 15% higher, than the median fluorescence intensity of an isotype-matched antibody which does not specifically bind the same target. Such expression of a marker is indicated by a superscript minus (−), following the name of the marker, e.g. CD25$^-$.

High expression of a marker, for example high expression of CD25, refers to the expression level of such marker in a clearly distinguishable cell population that is detected by FACS showing the highest fluorescence intensity per cell compared to the other populations characterized by a lower fluorescence intensity per cell. A high expression is indicated by superscript "high" or "hi" following the name of the marker, e.g. CD44$^{high}$. The term "is expressed highly" refers to the same feature.

Low expression of a marker, for example low expression of CD25, refers to the expression level of such marker in a clearly distinguishable cell population that is detected by FACS showing the lowest fluorescence intensity per cell compared to the other populations characterized by higher fluorescence intensity per cell. A low expression is indicated by superscript "low" or "lo" following the name of the marker, e.g. CD25$^{low}$. The term "is expressed lowly" refers to the same feature.

The expression of a marker may be assayed via techniques such as fluorescence microscopy, flow cytometry, ELISPOT, ELISA or multiplex analyses.

Amino acid residue sequences are given from amino to carboxyl terminus. Capital letters for sequence positions refer to L-amino acids in the one-letter code (Stryer, Biochemistry, 3$^{rd}$ ed. p. 21). Lower case letters for amino acid sequence positions refer to the corresponding D- or (2R)-amino acids. Sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term gene refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

The terms gene expression or expression, or alternatively the term gene product, may refer to either of, or both of, the processes—and products thereof—of generation of nucleic acids (RNA) or the generation of a peptide or polypeptide, also referred to transcription and translation, respectively, or any of the intermediate processes that regulate the processing of genetic information to yield polypeptide products. The term gene expression may also be applied to the transcription and processing of a RNA gene product, for example a regulatory RNA or a structural (e.g. ribosomal) RNA. If an expressed polynucleotide is derived from genomic DNA, expression may include splicing of the mRNA in a eukaryotic cell. Expression may be assayed both on the level of transcription and translation, in other words mRNA and/or protein product.

The term Nucleotides in the context of the present specification relates to nucleic acid or nucleic acid analogue building blocks, oligomers of which are capable of forming selective hybrids with RNA or DNA oligomers on the basis of base pairing. The term nucleotides in this context includes the classic ribonucleotide building blocks adenosine, guanosine, uridine (and ribosylthymine), cytidine, the classic deoxyribonucleotides deoxyadenosine, deoxyguanosine, thymidine, deoxyuridine and deoxycytidine. It further includes analogues of nucleic acids such as phosphotioates, 2'O-methylphosphothioates, peptide nucleic acids (PNA;

N-(2-aminoethyl)-glycine units linked by peptide linkage, with the nucleobase attached to the alpha-carbon of the glycine) or locked nucleic acids (LNA; 2'O, 4'C methylene bridged RNA building blocks).

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

In the context of the present specification, the terms sequence identity and percentage of sequence identity refer to a single quantitative parameter representing the result of a sequence comparison determined by comparing two aligned sequences position by position. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless stated otherwise, sequence identity values provided herein refer to the value obtained using the BLAST suite of programs (Altschul, J. Mol. Biol. 215:403-410 (1990)) using the above identified default parameters for protein and nucleic acid comparison, respectively.

Reference to identical sequences without specification of a percentage value implies 100% identical sequences (i.e. the same sequence).

In the context of the present specification, the term antibody refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains interconnected by disulphide bonds. Each heavy chain is comprised of a heavy chain variable region ($V_H$) and a heavy chain constant region ($C_H$). The heavy chain constant region of IgG is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system. The term antibody may also refer to an antibody-like molecule.

Similarly, the term antigen-binding antibody fragment or antigen-binding fragment encompasses a portion of an antibody molecule that retains the antigen binding capacity, such as antibody fragment selected from, but not limited to, a monovalent or bivalent antibody fragment (F(ab) or F(ab)$_2$ respectively), a so-called nanobody or single domain antibody, or an antibody fragment consisting of one, or several single monomeric variable antibody domains each comprising a $V_H$ and $V_L$.

In the context of the present specification, the term humanized antibody refers to an antibody originally produced by immune cells of a non-human species, the protein sequences of which have been modified to increase their similarity to antibody variants produced naturally in humans. The term humanized antibody as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term antibody-like molecule in the context of the present specification refers to a molecule capable of specific binding to another molecule or target with high affinity/a Kd≤10E-8 mol/l. An antibody-like molecule binds to its target similarly to the specific binding of an antibody. The term antibody-like molecule encompasses a repeat protein, such as a designed ankyrin repeat protein (Molecular Partners, Zürich), an engineered antibody mimetic proteins exhibiting highly specific and high-affinity target protein binding (see US2012142611, US2016250341, US2016075767 and US2015368302, all of which are incorporated herein by reference). The term antibody-like molecule further encompasses, but is not limited to, a polypeptide derived from armadillo repeat proteins, a polypeptide derived from leucine-rich repeat proteins and a polypeptide derived from tetratricopeptide repeat proteins.

The term antibody-like molecule further encompasses a specifically binding polypeptide derived from
  a protein A domain,
  fibronectin domain FN3,
  consensus fibronectin domains,
  a lipocalin (Skerra, *Biochim. Biophys. Acta* 2000, 1482 (1-2): 337-50),
  a polypeptide derived from a Zinc finger protein (Kwan, *Structure* 2003, 11 (7): 803-813),
  Src homology domain 2 (SH2) or Src homology domain 3 (SH3),
  a PDZ domain,
  gamma-crystallin,
  ubiquitin,
  a cysteine knot polypeptide or a knottin,
  cystatin,
  Sac7d,
  a triple helix coiled coil (also known as alphabodies),
  a Kunitz domain or a Kunitz-type protease inhibitor and
  a carbohydrate binding module 32-2.

8

The term protein A domains derived polypeptide refers to a molecule that is a derivative of protein A and is capable of specifically binding the Fc region and the Fab region of immunoglobulins.

The term armadillo repeat protein refers to a polypeptide comprising at least one armadillo repeat, wherein an armadillo repeat is characterized by a pair of alpha helices that form a hairpin structure.

The term humanized camelid antibody in the context of the present specification refers to an antibody consisting of only the heavy chain or the variable domain of the heavy chain (VHH domain) and whose amino acid sequence has been modified to increase their similarity to antibodies naturally produced in humans and, thus show a reduced immunogenicity when administered to a human being. A general strategy to humanize camelid antibodies is shown in Vincke et al. "General strategy to humanize a camelid single-domain antibody and identification of a universal humanized nanobody scaffold", J Biol Chem. 2009 Jan. 30; 284 (5): 3273-3284, and US2011165621A1.

The term specific binding in the context of the present invention refers to a property of ligands that bind to their target with a certain affinity and target specificity. The affinity of such a ligand is indicated by the dissociation constant of the ligand. A specifically reactive ligand has a dissociation constant of ≤$10^{-7}$ mol/L when binding to its target, but a dissociation constant at least three orders of magnitude higher in its interaction with a molecule having a globally similar chemical composition as the target, but a different three-dimensional structure.

In the context of the present specification, the term dissociation constant ($K_D$) is used in its meaning known in the art of chemistry and physics; it refers to an equilibrium constant that measures the propensity of a complex composed of [mostly two] different components to dissociate reversibly into its constituent components. The complex can be e.g. an antibody-antigen complex AbAg composed of antibody Ab and antigen Ag. $K_D$ is expressed in molar concentration [mol/l] and corresponds to the concentration of [Ab] at which half of the binding sites of [Ag] are occupied, in other words, the concentration of unbound [Ab] equals the concentration of the [AbAg] complex. The dissociation constant can be calculated according to the following formula:

$$K_D = \frac{[Ab]*[Ag]}{[AbAg]}$$

[Ab]: concentration of antibody; [Ag]: concentration of antigen; [AbAg]: concentration of antibody antigen complex In the context of the present specification, the terms off-rate ($K_{off}$; [1/sec]) and on-rate ($K_{on}$; [L/sec*mol]) are used in their meaning known in the art of chemistry and physics; they refer to a rate constant that measures the dissociation ($K_{off}$) or association ($K_{on}$) of an antibody with its target antigen. $K_{off}$ and $K_{on}$ can be experimentally determined using methods well established in the art. A method for determining the $K_{off}$ and $K_{on}$ of an antibody employs surface plasmon resonance. This is the principle behind biosensor systems such as the Biacore® or the ProteOn® system. They can also be used to determine the dissociation constant $K_D$ by using the following formula:

$$K_D = \frac{[K_{off}]}{[K_{on}]}$$

The natural upper limit for the on-rate $K_{on}$ is $10^9$ L/sec*mol.

As used herein, the term pharmaceutical composition refers to a compound of the invention, or a pharmaceutically acceptable salt thereof, together with at least one pharmaceutically acceptable carrier. In certain embodiments, the pharmaceutical composition according to the invention is provided in a form suitable for topical, parenteral or injectable administration.

As used herein, the term pharmaceutically acceptable carrier includes any solvents, dispersion media, coatings, surfactants, antioxidants, preservatives (for example, antibacterial agents, antifungal agents), isotonic agents, absorption delaying agents, salts, preservatives, drugs, drug stabilizers, binders, excipients, disintegration agents, lubricants, sweetening agents, flavouring agents, dyes, and the like and combinations thereof, as would be known to those skilled in the art (see, for example, Remington: the Science and Practice of Pharmacy, ISBN 0857110624).

As used herein, the term treating or treatment of any disease or disorder (e.g. cancer) refers in one embodiment, to ameliorating the disease or disorder (e.g. slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described hereinbelow.

The term interleukin-2, IL-2, or hIL-2 in the context of the complex provide in the present specification refers to the human IL-2 polypeptide, unless indicated otherwise. Numbering of human IL-2 residues throughout refers to that indicated in FIG. 10 (UniProt P60568). The term encompasses recombinantly produced IL-2 protein, such as the substances teceleukin (0094218-75-4), aldesleukin (CAS 110942-02-4), or its variant BAY 50-4798. Nuclear magnetic resonance spectroscopy suggests that the IL-2 protein comprises 4 major helices (A-D), flanked by two shorter helices (Arkin M. R et al. PNAS 2003, 100:1603-1608).

The term trimeric IL-2 receptor, or high-affinity IL-2 receptor used in the context of the current specification refers to a multimeric receptor made up of CD122 (IL-2Rα), CD132, and CD25 (IL-2Rα). The presence of CD25 increases the IL-2R's affinity with IL-2 by 100-fold compared to the dimeric IL-2R, which is why trimeric IL-2Rs ($K_d \approx 10^{-11}$ M) are also referred to as high-affinity IL-2Rs.

The terms intermediate affinity IL-2 receptor or dimeric IL-2 receptor in the context of the present specification refer to the IL-2 receptor comprising CD122 (IL-2Rβ) and the common gamma chain (γc; CD132). This dimeric IL-2R displays an intermediate affinity to IL-2 with a dissociation constant [$K_d$] of approximately $10^{-9}$ M, which is reduced when IL-2 interacts with the receptor in the context of a complex with the anti-hIL-2 mAb according to the invention due to steric hindrance of the bound antibody with the IL-2 binding site.

In the context of the present specification, the term peptide linker refers to a polypeptide of variable length that is used to connect two polypeptides in order to generate a single chain polypeptide. Exemplary embodiments of linkers useful for practicing the invention specified herein are oligopeptide chains consisting of 30, 40 or 50 amino acids.

The term T regulatory cells, and $T_{reg}$ in the context of the present specification refers particularly to CD3$^+$CD4$^+$ CD25$^+$immune cells with an immune-suppressive, or regulatory function. The intracellular expression of the $T_{reg}$ master transcription factor forkhead box P3 (Foxp3) identifies T cells with an immune-suppressive function. Further surface and intracellular markers associated with $T_{reg}$ cells are known in the art (Miyara M. et al. Autoimmun Rev 2011, 10:744). It is also possible to estimate the number of $T_{reg}$ in a sample by measuring a suppressive function, rather than measuring the expression of $T_{reg}$ markers on the surface of the cell. A suppression assay that would be useful for this purpose comprises combining the $T_{reg}$-containing sample with an active immune cell sample, particularly CD8+ T cells, and measuring inhibition of their function in terms of cell killing, proliferation, or production of effector molecules selected from, but not limited to, granzyme, perforin, interferon gamma (IFN) or tumour necrosis factor (TNF).

A first aspect of the invention provides a hIL-2 mAb, or a hIL-2-binding antibody fragment, wherein the hIL-2-specific mAb interacts with a defined epitope of hIL-2 amino acid residues comprising:

H16, D20 on the alpha helix;

Q57. E60, E61. L63, K64. E67, E68 on the B and B' helix; and

L80, R81, R83, D84, 186, S87, N88, N90, V91, L94, E95, K97, T101, T102, M104 on the C helix and C-D loop.

Crystal structure analysis shows that the following rhIL-2 residues are more than (>) 5 A$^2$ covered by the hIL-2-specific mAb antibody when the two molecules are associated:

H16, D20;

Q57, E60, E61, L63, K64, E67, E68; and

L80, R81, R83, D84, 186, S87, N88, N90, V91, L94, E95, K97, T101, T102, M104.

The following rhIL-2 residues are more than (>) 15 A$^2$ covered by the hIL-2-specific mAb antibody when the two molecules are associated, and are thus highly likely to mediate the important biological effector functions which characterise the antibody as outlined below:

H16;

Q57, E60, E61, K64, and

L80, R81, R83, D84, 186, S87, N88, N90, V91, L94, K97, T101, M104.

The data provided in the examples suggests hIL-2-specific mAb according to the invention differs from the previously described IL-2 mAb F5111.2 clone, as the epitope of an antibody according to the invention does not comprise the hIL-2 residues M23, G27, N71, Q74, S75, K76, N77, F78, P82.

Crystal structure analysis provided in the examples shows that Interactions between the anti-hIL-2 mAb and these specific residues block, or interrupt the interaction site between IL-2 and the intermediate-affinity IL-2 receptor consisting of CD122 and CD132. A complex of the anti-hIL-2 mAb and an IL-2 polypeptide has preferential, or biased, association with CD25, or the high affinity, trimeric IL-2R consisting of CD25, CD122, and CD132, resulting in increased IL-2 signalling in cells bearing this receptor, such as $T_{regs}$. The anti-hIL-2 mAb epitope according to the invention comprises the hIL-2 residues Q57, E60, E61, L64 and K64. The 6.3% overlap of the IL-2 CD25 binding obtained by the anti-hIL-2 mAb epitope provided here (and summarised in FIGS. 9 and 10 of the examples) helps the IL-2 be released from the anti-hIL-2 mAb complex, and delivered to the receptor unimpeded, resulting in improved IL-2 signalling compared to other antibody clones which do not include these residues in their epitope.

The epitope in the context of hIL-2 this invention, refers to the amino acid residues of the hIL-2 polypeptide that the hIL-2 specific mAb, or antibody fragment according to the invention specifically binds to, or attaches to. The hIL-2 epitope was defined by means of structural analysis of hIL-2 crystalized in complex with a Fab variant of the parent murine antibody UFKA-20, the CDRs of which were used to generate the humanised UFKA-22 clone and other hIL-2 specific mAb according to the invention (Table 1, FIGS. 9, 10, and 11). Equilibrium surface plasmon resonance (SPR) was performed on IL-2 captured by immobilized UFKA-20 to determine the crystal structure of the complex. The amino acids residues comprising the epitope according to the invention are defined as those with a buried surface area (measured in square angstroms, or $Å^2$) more than 0, calculated based using the software PDBePISA (Krissinel, *J Mol Biol* 2007 372, 774-797). In other words, the hIL-2 epitope comprises, or consists of, those IL-2 amino acids which, touch, interact with, are covered by, or are overlapped by the UFKA-20 antibody heavy and light chain polypeptides, particularly the complementary determining regions (CDR), but also by those residues which the antibody does not cover, or impede from receptor interactions.

The data in the examples demonstrates the utility of complete antibody molecules, with the hIL-2 epitope specified above, for forming a complex with hIL-2 which increases hIL-2 signalling to the trimeric IL-2R. Previous studies have shown that F(ab')2 antibody fragments, lacking the Fc portion of the antibody, can also form a hIL-2/mAb complex with a specific signalling bias, however they must be administered more frequently due to the shorter half-life of these fragments. Repeated injections of IL-2-specific F(ab')2 complexes with IL-2, but not of IL-2 alone, were able to mimic the potent activity of IL-2/mAb CD122-targeting complexes, thus suggesting that the specific binding, CDR containing portion of an anti-IL-2 mAb is crucial for in vivo activity (Letourneau, PNAS2010, 107 (5): 2171). Moreover, the inventors have shown in a related study with IL-7/anti-IL-7 (clone M25) mAb complexes, F(ab')2 antibody fragments worked as well as whole antibody molecules (Boyman, *J Immunol* 2008. 180 (11): 7265). Therefore, antibodies fragments lacking the Fc portion, such as Fab and F(ab') 2 fragments as well as scFv fragments are encompassed by the terms antibody, or antibody fragments according to the current invention.

A second aspect of the invention is an anti-hIL-2 mAb, or antigen-binding antibody fragment that is defined by characteristics of the interaction with the anti-hIL-2 antibody and the hIL-2 polypeptide. This aspect of the invention provides an anti-hIL-2 mAb, or a hIL-2-binding antibody fragment, wherein the binding of the hIL-2-specific mAb to hIL-2 is characterized by:

a dissociation constant $(K_D) \leq 5.51 \times 10^{-9}$ molL$^{-1}$, particularly a $K_D \leq 5.13 \times 10^{-9}$ moll-1 (the $K_D$ of clone UFKA-22-00);

an on-rate $(K_{on}) \geq 4.12 \times 10^5$ Lmol$^{-1}$s$^{-1}$ (the $K_{on}$ of clone UFKA-22-02), particularly a $K_{on} \geq 4.66 \times 10^5$ Lmol$^{-1}$s$^{-1}$ (the $K_{on}$ of the UFKA-22-00 clone)

an off-rate $(K_{off}) \leq 2.83 \times 10^{-3}$ s$^{-1}$ (the $K_{off}$ of clone UFKA-22-10), particularly a $K_{off} \leq 2.39 \times 10^{-3}$ s$^{-1}$ (the $K_{off}$ of clone UFKA-22-00).

The hIL-2 mAb according to this aspect of the invention has $K_D$ value$\leq 5.51 \times 10^{-9}$ molL-1 which is the highest $K_D$ value of the anti-hIL-2 mAb UFKA-22-02 amongst the selection of UFKA-20-derived clones demonstrated to have similar hIL-2-binding properties, and sharing the same CDR sequences. In particular embodiments, the anti-hIL-2 mAb according to the invention has a $K_D$ value$\leq 5.13 \times 10^{-9}$ molL$^{-1}$, the $K_D$ value of the hIL-2-specific clone UFKA-22-00, with no back mutations to the mouse framework region that might generate immune responses in a patient receiving this mAb as a component of a medicament. Secondly, the anti-hIL-2 mAb according to this aspect of the invention a $K_{on}$ value of $\geq 4.12 \times 10^5$ Lmol$^{-1}$s$^{-1}$ (derived from clone UFKA-22-02), and particularly a $K_{on} \geq 4.66 \times 10^5$ Lmol$^{-1}$ s$^{-1}$ (derived from UFKA-22-00). Lastly, the anti-hIL-2 mAb according to this aspect of the invention is characterised by a $K_{off} \leq 2.83 \times 10^{-3}$ s$^{-1}$ (derived from the clone UFKA-22-05), and particularly a $K_{off} \leq 2.39 \times 10^{-3}$ s$^{-1}$ (the $K_{off}$ of UFKA-22-00). The inventors find that antibodies that bind to IL-2 with the characteristics outlined above have similar kinetics of IL-2 binding and receptor delivery as the murine UFKA-20 clone used in preclinical studies in the examples (HC SEQ ID NO 019 and LC SEQ ID NO 020). An antibody with the above characteristics in complex with hIL-2 will preferentially deliver IL-2 signals to the high-affinity IL-2R. Importantly it will also dissociate from the complex, in other words, detach from the IL-2 polypeptide upon binding to the receptor, in order to allow delivery of an unimpeded, optimal signalling stimulus without steric hindrance from the antibody.

In other embodiments the interaction of hIL-2 and the hIL-2 mAb, or fragment thereof according to the invention is characterised by a $K_D \leq 5.51 \times 10^{-9}$ molL$^{31\ 1}$, particularly a $K_D \leq 5.13 \times 10^{-9}$ molL$^{-1}$ which is also more than an upper affinity limit of 1.856-10. The variant heavy and light chains 5+9 antibody that bound IL-2 with the highest affinity, showed reduced in vivo activity was observed with regards to CD4$^+$CD25$^+$Foxp3$^+$ T$_{reg}$ cell stimulation. In particular embodiments, the $K_D$ of said interaction is about 10$^{-10}$ M.

In some embodiments, the anti-hIL-2 mAb according to the invention is characterised by the biological function of a complex between hIL-2 and the anti-hIL-2 mAb, as measured by in vitro or in vivo experimental methods. The hIL-2 and anti-hIL-2 mAb complex according to the invention comprises a hIL-2 polypeptide, non-covalently associated with the anti-hIL-2 mAb according to the invention. These hIL-2 mAb complexes have been demonstrated to function effectively when the elements are combined at a 2:1 ratio (Boyman, *Science* 2006, 311:1924; Krieg, *PNAS* 2010, 107:11906; Arenas-Ramirez, *Sci Transl Med* 2016, 8, 367ra166), or at a 1:1 ratio (Letourneau, *PNAS* 2010, 107:11906; Arenas-Ramirez, *Sci Transl Med* 2016, 8: 367ra1660). The combination of the two components of the complex is performed in solution, and the time, temperature and conditions of this combination procedure are not particularly limited according to the invention. The complex may be formed, for example, by combining hIL-2 and the anti-hIL-2 mAb in physiological solution such as phosphate buffered saline at room temperature for 15 minutes. The preparation and activity of IL-2 mAb complexes using other mAb that bias IL-2 signalling towards IL-2Rα or IL-2Rβ, and therefore increase STAT5 phosphorylation in T$_{reg}$ or CD8$^+$ T cells has been demonstrated (Letourneau, *PNAS* 2010, 107:11906; Krieg, *PNAS* 2010, 107:11906; Trotta, *Nat Med* 2018, 24:1005).

In certain embodiments the complex of hIL-2 and the anti-hIL-2 mAb according to the invention shows increased binding affinity for the high-affinity IL-2R consisting of CD25, CD122 and CD132, in comparison to the binding affinity for the intermediate affinity IL-2R consisting of CD122 and CD132. In other words, the ratio of binding to the high affinity receptor, compared to the binding to the intermediate affinity IL-2R, is larger than 1. Particularly, this ratio is larger than 2, 4 or even 8. More particularly, the binding to the high affinity receptor is between 20 and 121 fold greater, or even more particularly, 71 times greater than binding to the intermediate affinity receptor. The data in the examples assessing interactions of the receptors and the hIL-2 complex differs with a fold change of 71, with an error range±50.

In certain embodiments, the complex of hIL-2 and the anti-hIL-2 mAb according to the invention shows increased binding affinity for CD25 alone, compared to the intermediate affinity receptor, particularly a fold change in affinity of between 277 and 483 times higher for CD25, more particularly 380 time greater than the intermediate affinity receptor. The data in the examples assessing interactions of the receptors and the hIL-2 complex differs with a fold change of 380, with an error range±103.

In the data presented in the examples, IL-2$_{Rhod}$/UFKA-20cx preferentially associated with CD25, with about two thirds of the measured interactions being made by IL-2$_{Rhod}$/UFKA-20cx, while in less than a third IL-2Rhod alone was detected on CD25. Binding of IL-2$_{Rhod}$/UFKA-20cx to CD122+CD132 was disfavoured by the presence of UFKA-20 compared to IL-2$_{Rhod}$ (FIG. 1D), demonstrating that UFKA-20 conferred a "CD25 bias" to IL-2$_{Rhod}$.

In certain embodiments of the anti-hIL-2 mAb, the anti-hIL-2 mAb disassociates from the complex of hIL-2 and the anti-hIL-2 mAb once the complex binds to the high-affinity hIL-2 receptor. In other words, the two components are associated before binding to the receptor, and upon binding, free hIL-2 is released, to enable optimal signalling through the receptor.

In FIG. 1D of the examples, CD25 bias and dissociation of the anti-hIL-2 mAb from hIL-2 is demonstrated by biased delivery of the complex to CD25, or CD25/CD122/CD132 expressed by HEK cells, leaving IL-2 in place binding to the receptor, as observed using flow cytometry where each component is fluorescently labelled. hIL-2$_{Rhod}$/UFKA-20cx rapidly dissociated upon interaction with trimeric CD25$^+$ CD122+CD132, as evidenced by less than 8.4% of this interaction being formed by IL-2$_{Rhod}$/UFKA-20cx and 91.6% by uncomplexed, free IL-2$_{Rhod}$ binding to CD25$^+$ CD122+CD132 (FIG. 1D-1F). Delivery is defined as free IL2rhodamine binding to over 40% of CD25/CD122/CD132+ cells, when delivered in hIL-2 complex with the anti-hIL-2 mAb according to the invention. UFKA-30 and UFKA-40 enforced a stronger CD25 bias upon IL-2$_{Rhod}$, but failed to dissociate, or deliver, IL-2 to trimeric IL-2R (FIG. 1D to H).

In certain embodiments, the anti-hIL-2 mAb according to the invention activates human CD3$^+$CD4$^+$Foxp3$^+$ T$_{reg}$ cells with an EC50<0.154 ng/ml, and human CD8$^+$ T cells with an EC50>442.9 ng/ml, when delivered to cells in a complex with hIL-2. The methodology by which T$_{reg}$ or CD8$^+$ T cell activation is measured in order to calculate an EC50 of the complex is not particularly limited according to the invention. In the data presented here in the examples, T$_{reg}$ activation by the hIL-2 complex with the anti-hIL-2 mAb is measured by the level of phosphorylated STAT5 (pSTAT5) induced in human T cells in FIG. 6, measured by flow cytometry after cell culture, but may be measured by other activation features such as proliferation, or effector cytokine production.

Alternatively, in other embodiments of the anti-hIL-2 mAb, preferential promotion of T$_{reg}$ proliferation is determined by ascertaining the ratio of CD3$^+$CD4$^+$CD25$^+$ T$_{reg}$ cells over CD8$^+$CD44$^{hi}$ CD122$^+$ memory T cells after treatment with the complex. In the examples, this treatment resulted in 2-3 fold larger increase in T$_{regs}$, compared to the increase in CD8$^+$ memory T cells in the spleen or lymph nodes of macaques (FIG. 8), or human cells cultured in vitro (FIG. 6). In other words, the ratio of the percent increase of T$_{reg}$ cells, compared to the percent increase of CD8$^+$ CD44$^{hi}$ CD122$^+$ T cells is greater than 1, when the anti-hIL-2 mAb according to the invention is delivered to humans or macaque cells in a complex with IL-2, compared to either an untreated, or pre-treatment sample. This ratio of T$_{reg}$ activation may alternatively be calculated in comparison to the total number or percent of IL2Rα-cells, such as, but not limited to, CD8$^+$ T cells, natural killer cells, and/or B cells.

A third aspect of the invention is a hIL-2-specific mAb, or an antigen-binding antibody fragment thereof, comprising a V$_H$ region characterised by a CDR$_H$1, CDR$_H$2 and CDR$_H$3, and a light chain variable, particularly a kappa light (V$_L$) region comprising a CDR$_L$1, CDR$_L$2 and CDR$_L$3. According to this aspect of the invention, the CDR$_H$1, CDR$_H$2, CDR$_H$3, CDR$_L$1, CDR$_L$2 and CDR$_L$3 comprise, or are identical to SEQ ID NO 001, SEQ ID NO 002, SEQ ID NO 003, SEQ ID NO 004, SEQ ID NO 005, and SEQ ID NO 006, respectively. The anti-hIL-2 mAb according to this aspect of the invention may optionally be characterised by the epitope or binding characteristics according to any of the previous aspects of the invention.

In another embodiment, the anti-hIL-2 mAb, or antigen-binding fragment thereof according to the invention, particularly an antibody characterised by any of the previous aspects, is characterised by:
- a. a CDR$_H$1, CDR$_H$2 and CDR$_H$3 comprised in a V$_H$ sequence selected from SEQ ID NO 007, SEQ ID NO 008, SEQ ID NO 009, SEQ ID NO 010, SEQ ID NO 011, SEQ ID NO 012, SEQ ID NO 013, or SEQ ID NO 014, particularly wherein the CDR$_H$ are comprised in SEQ ID NO 007, and,
- b. a CDR 1, CDR$_L$2 and CDR$_L$3 comprised in a V$_L$ sequence selected from SEQ ID NO 015, or SEQ ID NO 016, particularly wherein the CDR, are comprised in SEQ ID NO 015.

In the data presented in the examples, Table 2 shows similar K$_{off}$, K$_{on}$, K$_D$ values in a range of hIL-2 antibodies corresponding to the sequences above, demonstrating that these are functional alternatives. These biochemical values are a predictable indicator of function and performance by other in vitro or in vivo measures described in previous aspects of the invention. The UFKA-22-00 clone provided with a heavy chain of SEQ NO 007 and light chain of SEQ ID NO 015 is considered most desirable only insomuch as other options contain "back" mutations that resemble the mouse Ig molecule, and maybe have a higher risk of generating anti-drug immunity in a human patient.

A fourth aspect of the hIL-2-specific mAb according to the invention, particularly a hIL-2-specific mAb according to any of the previous aspects, is an anti-hIL-2 mAb characterised by a V$_H$ region sequence ≥96% identical to SEQ ID NO 007, particularly a V$_H$ region sequence ≥96% identical to SEQ ID NO 007, and wherein
positions 74, and/or 84 are serine, and/or
position 93 is methionine, and/or
position 122 is alanine.

Additionally, the mAb according to this aspect of the invention is characterised by a V$_L$ region ≥99% identical to SEQ ID NO 015, particularly a V$_L$ region ≥99% identical to SEQ ID NO 015, and wherein position 69 is isoleucine.

The data in Table 2 of the examples demonstrates clones bearing the essential CDR regions, and additional framework mutations having similar interactions with hIL-2 as the primary heavy and light chains sequences SEQ ID NO 007 and SEQ ID NO 015, respectively, that were tested in the largest range of functional assays. If all positions in the heavy chain listed in a. were to differ, the sequence would be 5.74% different from SEQ ID NO 007, in other words, more than 96% identical to SEQ ID NO 007. If position 69 of the light chain is exchanged for an isoleucine, the resulting SEQ ID NO 016 sequence is 0.88% different from the parent SEQ ID NO 15 sequence, in other words, more than 99% identical to SEQ ID NO 015.

A fifth aspect of the hIL-2-specific mAb, or antigen-binding fragment thereof, particularly one characterised by any previous aspect or embodiment of the invention, is an anti-hIL-2 mAb with a $V_H$ or $V_L$ sequences with at most two, or particularly one, conservative amino acid substitution. In other words, the anti-hIL-2 mAb $V_H$ region comprises a sequence selected from SEQ ID NO 007 ($V_H1$), SEQ ID NO 008 ($V_H2$), SEQ ID NO 009 ($V_H3$), SEQ ID NO 010 ($V_H4$), SEQ ID NO 011 ($V_H5$), SEQ ID NO 012 ($V_H6$), SEQ ID NO 013 ($V_H7$), or SEQ ID NO 014 ($V_H8$), or a functionally similar sequence derived from any one of these reference sequences by the substitution rules given below. In addition, the anti-hIL-2 mAb $V_L$ region comprises a sequence selected from SEQ ID NO 015 ($V_L1$), SEQ ID NO 016 ($V_L2$), or a functionally similar sequence derived from any one of these reference sequences by following substitution rules. The rules to provide possible conservative amino acid changes, lists amino acids with similar biochemical properties which may be exchanged and result in a functionally similar sequence to their respective reference sequence. The substitution rules are:

I. glycine (G) and alanine (A) are interchangeable; valine (V), leucine (L), and isoleucine (I) are interchangeable, A and V are interchangeable;

II. tryptophan (W) and phenylalanine (F) are interchangeable, tyrosine (Y) and F are interchangeable;

III. serine(S) and threonine (T) are interchangeable;

IV. aspartic acid (D) and glutamic acid (E) are interchangeable

V. asparagine (N) and glutamine (Q) are interchangeable; N and S are interchangeable; N and D are interchangeable; E and Q are interchangeable;

VI. methionine (M) and Q are interchangeable;

VII. cysteine (C), A and S are interchangeable;

VIII. proline (P), G and A are interchangeable;

IX. arginine (R) and lysine (K) are interchangeable;

A further aspect of the invention provides an anti-hIL-2 mAb, wherein the antibody or antibody fragment is characterised by an epitope according to the first aspect of the invention, or binds to hIL-2 with the characteristics provided by the second aspect of the invention, as well as comprising:

a. a first sequence ≥90% identical, particularly ≥94%, ≥96% or even ≥98% identical to at least one of SEQ ID NO 007 ($V_H1$), SEQ ID NO 008 ($V_H2$), SEQ ID NO 009 ($V_H3$), SEQ ID NO 010 ($V_H4$), SEQ ID NO 011 ($V_H5$), SEQ ID NO 012 ($V_H6$), SEQ ID NO 013 ($V_H7$), SEQ ID NO 014 ($V_H8$) or SEQ ID NO 017 (HC); and b. a second sequence ≥90% identical, particularly ≥94%, ≥96% or even ≥98% identical to at least one of SEQ ID NO 015 ($V_L1$), SEQ ID NO 016 ($V_L2$), or SEQ ID NO 018 (LC).

In particular embodiments of the anti-hIL-2 monoclonal antibody, the antibody consists of heavy chains with the sequence designated SEQ ID NO 017, associated with light chains of the sequence designated SEQ ID NO 018.

A next aspect of the invention provides a hIL-2 fusion protein comprising a hIL-2-specific mAb according to any one of the aspects of the invention herein, and a hIL-2 polypeptide, wherein these two components are joined by a peptide linker.

The hIL-2 fusion protein comprises a hIL-2-specific mAb made up of an antibody heavy chain having an N terminus and a C terminus; and an antibody light chain having an N terminus and a C terminus. Said antibody heavy chain comprises from N to C terminus, a $CDR_H1$, $CDR_H2$ and $CDR_H3$ with the sequences designated SEQ ID NO 001, SEQ ID NO 002, SEQ ID NO 003, respectively. In particular embodiments, these CDR are comprised in a $V_H$ sequence selected from SEQ ID NO 007, SEQ ID NO 008, SEQ ID NO 009, SEQ ID NO 010, SEQ ID NO 011, SEQ ID NO 012, SEQ ID NO 013, or SEQ ID NO 014. In more particular embodiments, the three $CDR_H$ are comprised in SEQ ID NO 007. Likewise, the antibody light chain includes the complementary determining regions CDR 1, $CDR_L2$ and $CDR_L3$ with sequences SEQ ID NO 004, SEQ ID NO 005, SEQ ID NO 006, respectively. In particular embodiments, these are comprised in a $V_L$ sequence selected from SEQ ID NO 015, or SEQ ID NO 016. In more particular embodiments, the $CDR_L$ are comprised in SEQ ID NO 015.

The hIL-2 polypeptide portion of the hIL-2 fusion protein according to the invention, also having an N terminus and a C terminus, may be any natural IL-2 polypeptide, or a recombinant IL-2 protein such as teceleukin or aldesleukin. In particular embodiments, the polypeptide sequence of the hIL-2 portion of the fusion protein is that of the hIL-2 protein P60568.

The peptide linker of joining the antibody to the IL-2 portion of the fusion protein according to the invention is preferably between 30 and 50 amino acids in length. In particular embodiments, the peptide linker is 30 to 40 amino acids in length. In more particular embodiments, the peptide linker is between 30 and 35 amino acids in length. In still more particular embodiments, the peptide linker is about 30 amino acids in length. In particular embodiments, the peptide linker of the hIL-2 fusion protein according to the invention joins the C-terminus of the hIL-2 polypeptide to either the N-terminus of the antibody heavy chain, or to the N-terminus of the antibody light chain. In more particular embodiments, the peptide linker joins the C-terminus of the hIL-2 polypeptide to the N-terminus of the antibody light chain, as demonstrated in the embodiment of the hIL-2 fusion protein mAb LC component designated SEQ ID NO 028.

In particular embodiments of the hIL-2 fusion protein according the invention, the peptide linker is comprised of about 85% glycine and about 15% serine amino acid residues, as these are residues that offer reduced immunogenicity. In particular embodiments of the hIL-2 fusion protein, the peptide linker has the sequence SEQ ID NO 027. In still more particular embodiments, the hIL-2 fusion protein is a bivalent molecule wherein each heavy chain, or each light chain, is independently fused to hIL-2 by said peptide linker. In other embodiments, the hIL-2 fusion protein comprises a signal peptide permitting secretion of the recombinant protein, for example, the signal peptide with the sequence SEQ ID NO 027. In still further particular embodiments, the hIL-2 fusion protein consists of LC fused to hIL-2 providing the sequence designated SEQ ID NO 028, further associated with the $V_H$ chain SEQ ID NO 017.

A next aspect of the invention provides a nucleic acid molecule encoding the hIL-2-specific mAb, or antigen-binding antibody fragment, according to any one of the previous aspects or embodiments specified above. Another aspect of the invention relates to a nucleic acid molecule encoding the hIL-2 fusion protein according to the invention. Another aspect of the invention provides a vector comprising said nucleic acid, while further aspects provides a cell, or a monoclonal antibody-producing hybridoma line comprising the anti-hIL-2 mAb or fragment thereof, hIL-2 fusion protein, the nucleic acid, or the vector according to the specifications listed in the above aspects of the invention.

Another aspect of the invention is a pharmaceutical formulation for use as a medicament, particularly for use treating a patient with harmful immune-mediated inflammation, more particularly harmful immune-mediated infiltration derived from an allograft-related disorder, chronic inflammation such as vasculitis, or an allergic, or autoimmune condition. The pharmaceutical formulation according to this aspect of the invention comprises at least two components:

- a. the hIL-2-specific mAb, or antigen-binding fragment thereof, according to any one of the aspects or embodiments of the invention listed above, and
- b. hIL-2.

The inventors believe that improved IL-2Ra-bias delivered by the IL-2-specific mAb according to the invention in complex with a hIL-2 polypeptide, will plausibly provide improved therapeutic effects in medical indications which may be treated by current IL-2 administration approaches. IL-2 immunotherapy has been shown to alleviate rheumatoid arthritis, ankylosing spondylitis, psoriasis, inflammatory bowel disease, autoimmune hepatitis, amyotrophic lateral sclerosis, HCV-related vasculitis, Type I diabetes, chronic graft-versus-host disease (GVHD), lupus, alopecia areata, systemic lupus erythematosus and improved liver transplantation protocols in human clinical trials (Ye, *Signal Transduct Target Ther* 2018, 3:2; Sharabi, *Nat. Rev. Drug Discov.* 2018, 17:823). Mouse models of human disease suggest IL-2 based immunotherapy to improve IL-2Rα signalling can improve clinical features of multiple sclerosis, inflammatory or autoimmune myopathy, inflammatory colitis, lupus, xenogeneic GVHD, allergic asthma, metabolic disease such as obesity related inflammation and insulin resistance that characterise type I and II diabetes, as well as atherosclerosis and Duchenne muscular dystrophy (Arenas-Ramirez, *Trends Immunol* 2015, 36:763, Tang, *Immunity* 2008, 28:687; Webster, *J. Exp. Med.* 2009, 206: 751; Lee, *Immunol.* 2012, 137:305; Spangler, *Immunity* 2015, 42:815; Yan, *Kidney Int.* 2017, 91:603, Trotta, *Nat Med* 2018, 24:1005).

Immune-mediated medical conditions where enhanced IL-2 immunotherapy has improved clinical outcomes, achieved, for example, by means of low dose IL-2, recombinant IL-2 molecules, or IL-2-containing pharmaceutical formulations, may also be considered for treatment by the hIL-2 mAb and hIL-2 complex according to the invention. These immune-mediated medical indication include, for example, chronic inflammation conditions, allergy, or autoimmunity, and metabolic diseases amenable to IL-2 immunotherapy. In addition, the treatment of allograft-related disorders is encompassed, for example, whole organ transplantation, tissue transplantation, or bone marrow transfer, and may include application of the IL-2-specific mAb associated with IL-2 before the transplant procedure, as a conditioning approach, and/or after the transplant procedure. In certain embodiments, the allograft-related disorder is the transplantation of an entire organ, for example, kidney, or lung transplantation.

In the data provided in the examples, the anti-hIL-2 mAb and IL-2 used as a medicament in vivo are associated at a 1:1 ratio, and substantially devoid of free hIL-2, but the ratio in which the components are combined may differ, for example may be 2:1, 1:1 or even 1:2. Parenteral, or local injection of this type of complex increases the ratio of $T_{regs}$ to inflammatory cells, suppressing immune activation that causes harmful tissue pathology in allergy, infection or autoimmune disease.

In some embodiments, the hIL-2 and the anti-hIL-2 mAb comprised in the pharmaceutical formulation are covalently associated. The data in the examples suggests that disassociation of IL-2 from the anti-hIL-2 mAb is a distinguishing feature of the mAb according to the invention, suggesting that any linkage between the hIL-2 and hIL-2mAb according to this embodiment should not impede the ability of hIL-2 to deliver an optimal signal through the high-affinity IL-2R. In particular embodiments, the covalently associated hIL-2 and anti-hIL-2 mAb are in form of an hIL-2 fusion protein according to the invention.

In other embodiments the hIL-2 containing pharmaceutical composition according to the previous aspects of the invention, is a compound medicament which further comprises an mTOR inhibitor, particular an mTOR inhibitor selected from rapamycin (sirolimus), everolimus, an anti-inflammatory mAb, particularly a mAb selected from anti-TNF, anti-IL-6, oranti-OX40L blockade, a corticosteroid drug, a sphingosine-1-phosphate (S1P) pathway inhibitor, particularly an S1P pathway inhibitor selected from FTY720, or an S1P receptor blocker, an anti-inflammatory antioxidant drug, particularly an anti-inflammatory antioxidant drug selected from metformin or N-acetyl cysteine, calmodulin kinase type II or type IV inhibitors, PI3K inhibitors, or pyrazopyramidine derivatives, $T_{reg}$ cell-specific histone deacetylases such as HDAC6, $T_{reg}$ cell therapy, for example, Chimeric antigen receptor or transgenic T cell receptor $T_{reg}$ therapy and/or low-dose IL-2, Ig-fusion IL-2, or pegylated IL-2.

The synergy of the hIL-2 and anti-hIL-2 mAb complex according to the invention with the medicaments listed above are due to their complementary mechanisms of action by a review from an expert in the field IL-2 biology and oncology (Sharabi A. et al. *Nat. Rev. Drug Discov.* 2018, 17:823).

Another aspect of the invention is a method of treating immune inflammation comprising:

- i. selecting a patient diagnosed with a condition characterized by a harmful inflammation, particularly allograft-related disorders, chronic inflammation, allergy, or autoimmunity, and
- ii. administering the anti-hIL-2 mAb according to any one of the claims 1 to 8, and hIL-2 in a complex of 2:1 or 1:2, particularly combined at a ratio of 1:1.

A further aspect provides the use the hIL-2-specific mAb, or antigen-binding fragment, or hIL-2 fusion protein according any of the previous aspects of the invention, in the manufacture of a medicament for use in the treatment of immune-mediated diseases, particularly allograft-related disorders, chronic inflammation, allergy, or autoimmune conditions.

Another aspect of the invention provides an isolated antibody or antigen-binding fragment thereof, which binds to a hIL-2 epitope comprising the hIL-2 residues H16, D20, Q57, E60, E61, L63, K64, E67, E68, L80, R81, R83, D84, 186, S87, N88, N90, V91, L94, E95, K97, T101. T102, M104 and excluding the hIL-2 residues M23, G27, N71, Q74, S75, K76, N77, F78, P82.

A final aspect of the invention provides an isolated antibody or antigen-binding fragment thereof, which comprises an antigen recognition surface having epitope recognition characteristics equivalent to an antibody or molecule according to any of the specification provided above.

Medical Treatment, Dosage Forms and Salts

Similarly, within the scope of the present invention is a method or treating inflammatory disorders in a patient in need thereof, comprising administering to the patient a pharmaceutical composition comprising hIL-2 and an anti-hIL-2 mAb according to the above description.

In certain embodiments, the anti-hIL-2 mAb is an antibody, antibody fragment, an antibody-like molecule, or a protein A domains derived polypeptide.

In some embodiments, the anti-hIL-2 mAb is an immunoglobulin consisting of two heavy chains and two light chains. In some embodiments, the anti-hIL-2 mAb is a single domain antibody, consisting of an isolated variable domain from a heavy or light chain.

In certain embodiments, the anti-hIL-2 mAb is an antibody fragment. In certain embodiments, the anti-hIL-2 mAb is a Fab fragment, i.e. the antigen-binding fragment of an antibody, or a single-chain variable fragment, i.e. a fusion protein of the variable region of heavy and the light chain of an antibody connected by a peptide linker. Multiple single chain variable fragments, with either the same, or differing antigen specificity, may be combined into a multimeric format which forms two or more discrete epitope binding regions.

In other embodiments, the composition comprises a covalently linked hIL-2 and anti-hIL-2 mAb. In particular embodiments, said composition comprises a hIL-2 fusion protein.

Similarly, a dosage form for the prevention or treatment of inflammatory conditions is provided, comprising a complex of anti-hIL-2 mAb and IL-2 according to any of the above aspects or embodiments of the invention.

The skilled person is aware that any specifically mentioned drug may be present as a pharmaceutically acceptable salt of said drug. Pharmaceutically acceptable salts comprise the ionized drug and an oppositely charged counterion. Non-limiting examples of pharmaceutically acceptable anionic salt forms include acetate, benzoate, besylate, bitatrate, bromide, carbonate, chloride, citrate, edetate, edisylate, embonate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate, phosphate, diphosphate, salicylate, disalicylate, stearate, succinate, sulfate, tartrate, tosylate, triethiodide and valerate. Non-limiting examples of pharmaceutically acceptable cationic salt forms include aluminium, benzathine, calcium, ethylene diamine, lysine, magnesium, meglumine, potassium, procaine, sodium, tromethamine and zinc.

IL-2 complexes have been successfully applied by subcutaneous, intravenous and intraperitoneal routes in experimental models, therefore parenteral administration may be used, such as subcutaneous, intravenous, intrahepatic or intramuscular injection forms.

However the inventors predict dosage forms for topical, or enteral administration, such as nasal, buccal, rectal, transdermal or oral administration, or as an inhalation form or suppository may also produce the desired physiological outcomes. Optionally, a pharmaceutically acceptable carrier and/or excipient may be present.

Topical administration is also within the scope of the advantageous uses of the invention. The skilled artisan is aware of a broad range of possible recipes for providing topical formulations, as exemplified by the content of Benson and Watkinson (Eds.), Topical and Transdermal Drug Delivery: Principles and Practice (1st Edition, Wiley 2011, ISBN-13:978-0470450291); and Guy and Handcraft: Transdermal Drug Delivery Systems: Revised and Expanded ($2^{nd}$ Ed., CRC Press 2002, ISBN-13:978-0824708610); Osborne and Amann (Eds.): Topical Drug Delivery Formulations ($1^{st}$ Ed. CRC Press 1989; ISBN-13:978-0824781835).

Pharmaceutical Compositions and Administration

Another aspect of the invention relates to a pharmaceutical composition comprising a compound of the present invention, or a pharmaceutically acceptable salt thereof, and a pharmaceutically acceptable carrier. In further embodiments, the composition comprises at least two pharmaceutically acceptable carriers, such as those described herein.

In certain embodiments of the invention, the compound of the present invention is typically formulated into pharmaceutical dosage forms to provide controlled dosage of the drug.

In embodiments of the invention relating to topical uses of the compounds of the invention, the pharmaceutical composition is formulated in a way that is suitable for topical administration such as aqueous solutions, suspensions, ointments, creams, gels or sprayable formulations, e.g., for delivery by aerosol or the like, comprising the active ingredient together with one or more of solubilizers, stabilizers, tonicity enhancing agents, buffers and preservatives that are known to those skilled in the art.

The pharmaceutical composition can be formulated for oral administration, parenteral administration, or rectal administration. In addition, the pharmaceutical compositions of the present invention can be made up in a solid form (including without limitation capsules, tablets, pills, granules, powders or suppositories), or in a liquid form (including without limitation solutions, suspensions or emulsions).

The dosage regimen for the compounds of the present invention will vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. In certain embodiments, the compounds of the invention may be administered in a single daily dose, or the total daily dosage may be administered in divided doses of two, three, or four times daily.

In certain embodiments, the pharmaceutical composition or combination of the present invention can be in unit dosage of about 1-1000 mg of active ingredient(s) for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The pharmaceutical compositions of the present invention can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. They may be produced by standard processes, for instance by conventional mixing, granulating, dissolving or lyophilizing processes. Many such procedures and methods for preparing pharmaceutical compositions are known in the art, see for example L. Lachman et al. The Theory and Practice of Industrial Pharmacy, 4th Ed, 2013 (ISBN 8123922892).

Wherever alternatives for single separable features such as, for example, an isotype protein or coding sequence, ligand type or medical indication are laid out herein as "embodiments", it is to be understood that such alternatives may be combined freely to form discrete embodiments of the invention disclosed herein. Thus, any of the alternative embodiments for an antibody may be combined with any medical indication mentioned herein.

The invention further encompasses the following items:

1. A human interleukin-2 (hIL-2)-specific monoclonal antibody (mAb), or antigen-binding fragment thereof, wherein the hIL-2-specific mAb interacts with hIL-2 amino acid residues to provide an epitope, and wherein the epitope comprises the hIL-2 residues

H16, D20,

Q57. E60, E61, L63, K64, E67, E68, and

L80, R81, R83, D84, I86, S87. N88, N90, V91, L94, E95, K97, T101, T102, M104.

2. A hIL-2-specific mAb, or antigen-binding fragment thereof, particularly a hIL-2-specific mAb, or antigen-binding fragment thereof according to item 1, wherein the binding of the hIL-2-specific mAb to hIL-2 is characterized by:

a dissociation constant ($K_D$) equal or smaller than ($\leq$) $4.3\times10^{-9}$, particularly a $K_D \leq 5.13\times10^{-9}$, an on-rate ($K_{on}$) equal or greater than (2) $4.12\times10^{5}$ $Ms^{-1}$, particularly a $K_{on} \geq 4.66\times10^{5}$ $Ms^{-1}$, and an off-rate ($K_{off}$)$\leq 2.20\times10^{-3}$ $s^{-1}$, particularly a $K_{off} \leq 2.39\times10^{-3}$ $s^{-1}$.

3. The hIL-2-specific mAb, or antigen-binding fragment thereof, according to item 1 or 2, wherein a complex of the hIL-2-specific mAb and hIL-2 combined in a ratio between 2:1 to 1:2, particularly combined in a ratio of 1:1 is characterized by:

a ratio of binding to the high-affinity hIL-2 receptor compared to the intermediate-affinity hIL-2 receptor of between 20 to 121, particularly a ratio of between 71 and 121, and/or a ratio of binding affinity for CD25 alone, compared to the intermediate-affinity hIL-2 receptor of between 277 to 483, particularly a ratio of between 380 to 483, and/or dissociation of the hIL-2 mAb from hIL-2 on binding of the complex to the high-affinity hIL-2 receptor, and/or activating human CD3$^+$CD4$^+$CD127low Foxp3$^+$ $T_{reg}$ cells with an EC50$\leq$0.154, and human CD8$^+$ T cells with an EC50$\geq$442.9.

4. A hIL-2-specific mAb, or antigen-binding fragment thereof, particularly a hIL-2-specific mAb according to any one of the items 1 to 3, which comprises a heavy chain variable ($V_H$) region comprising a $V_H$ complementarity determining region CDR$_H$1, CDR$_H$2 and CDR$_H$3, and a variable light chain ($V_L$) region comprising a $V_L$ complementarity determining region CDR$_L$1, CDR$_L$2 and CDR$_L$3, and wherein a. CDR$_H$1 comprises, or is identical to SEQ ID NO 001; and b. CDR$_H$2 comprises, or is identical to SEQ ID NO 002, and c. CDR$_H$3, comprises, or is identical to SEQ ID NO 003; and d. CDR$_L$1 comprises, or is identical to SEQ ID NO 004; and e. CDR$_L$2 comprises, or is identical to SEQ ID NO 005; and f. CDR$_L$3 comprises, or is identical to SEQ ID NO 006.

5. A hIL-2-specific mAb, or antigen-binding fragment thereof, particularly a hIL-2-specific mAb according to any one of the items 1 to 4, wherein a. the CDR$_H$1, CDR$_H$2 and CDR$_H$3 are comprised in a $V_H$ sequence selected from SEQ ID NO 007, SEQ ID NO 008, SEQ ID NO 009, SEQ ID NO 010, SEQ ID NO 011, SEQ ID NO 012, SEQ ID NO 013, and SEQ ID NO 014, particularly wherein the CDR$_H$ are comprised in SEQ ID NO 007, and wherein, b. the CDR$_L$1, CDR$_L$2 and CDR$_L$3 are comprised in a $V_L$ sequence selected from SEQ ID NO 015, and SEQ ID NO 016, particularly wherein the CDR$_L$ are comprised in SEQ ID NO 015.

6. A hIL-2-specific mAb, or antigen-binding fragment thereof, particularly a hIL-2-specific mAb according to any one of the items 1 to 5, which comprises:

a. a $V_H$ region sequence $\geq$96% identical to SEQ ID NO 007, and wherein:

positions 74, and/or 84 are serine, and/or position 93 is methionine, and/or position 122 is alanine;

and, b. a $V_L$ region $\geq$99% identical to SEQ ID NO 015, and wherein:

position 69 is isoleucine.

7. A hIL-2-specific mAb, or antigen-binding fragment thereof, particularly a hIL-2-specific mAb according to any one of the items 1 to 5, wherein a. the $V_H$ region comprises a sequence selected from SEQ ID NO 007, SEQ ID NO 008, SEQ ID NO 009, SEQ ID NO 010, SEQ ID NO 011, SEQ ID NO 012, SEQ ID NO 013, and SEQ ID NO 014, or a functionally similar sequence derived from any one of these reference sequences by the substitution rules given below; and b. the $V_L$ region comprises a sequence selected from SEQ ID NO 015, and SEQ ID NO 016, or a functionally similar sequence derived from any one of these reference sequences by the substitution rules given below, and wherein the substitution rules for deriving the functionally similar sequence from their respective reference sequence are:

i. glycine (G) and alanine (A) are interchangeable; valine (V), leucine (L), and isoleucine (I) are interchangeable, A and V are interchangeable;

ii. tryptophan (W) and phenylalanine (F) are interchangeable, tyrosine (Y) and F are interchangeable;

iii. serine(S) and threonine (T) are interchangeable;

iv. aspartic acid (D) and glutamic acid (E) are interchangeable 23 24 v. asparagine (N) and glutamine (Q) are interchangeable; N and S are interchangeable; N and D are interchangeable; E and Q are interchangeable;

vi. methionine (M) and Q are interchangeable;

vii. cysteine (C), A and S are interchangeable;

viii. proline (P), G and A are interchangeable;

ix. arginine (R) and lysine (K) are interchangeable;

particularly wherein at most two amino acids are exchanged, more particularly wherein at most one amino acid is exchanged by the substitution rules given above.

8. The hIL-2-specific mAb, or antigen-binding fragment thereof, with characteristics according to any one of the items 1 to 3, and further comprising
   a. a first sequence ≥90% identical, particularly ≥94%, ≥96% or even ≥98% identical to at least one of SEQ ID NO 007, SEQ ID NO 008, SEQ ID NO 009, SEQ ID NO 010, SEQ ID NO 011, SEQ ID NO 012, SEQ ID NO 013, SEQ ID NO 014, and SEQ ID NO 017; and
   b. a second sequence ≥90% identical, particularly ≥94%, ≥96% or even ≥98% identical to at least one of SEQ ID NO 015, SEQ ID NO 016, and SEQ ID NO 018.

9. The hIL-2-specific mAb according to any one of the items 1 to 8, wherein the hIL-2-specific mAb comprises:
   a. a heavy chain, said heavy chain comprising or consisting of SEQ ID NO 017; and
   b. a light chain, said light chain comprising or consisting of SEQ ID NO 018.

10. A hIL-2 fusion protein comprising:
    a. a human interleukin-2 (hIL-2)-specific monoclonal antibody (mAb) according to any one of items 1 to 9, said antibody comprising consisting of
       i. an antibody heavy chain; and
       ii. an antibody light chain; and
    b. a hIL-2 polypeptide;
    c. a peptide linker between 25 and 50 amino acids in length, particularly 25 to 35 amino acids in length, more particularly 30 amino acids in length, and
    wherein the peptide linker joins the C-terminus of the hIL-2 polypeptide to either the N-terminus of the antibody heavy chain, or to the N-terminus of the antibody light chain, particularly wherein the peptide linker joins the C-terminus of the hIL-2 polypeptide to the N-terminus of the antibody light chain.

11. The hIL-2 fusion protein according to item 10, wherein the peptide linker is comprised of about 85% glycine and about 15% serine, particularly wherein the peptide linker has the sequence SEQ ID NO 026.

12. A nucleic acid molecule encoding the hIL-2-specific mAb, or antigen-binding fragment thereof, according to any one of the claims 1 to 9, or the hIL-2 fusion protein according to items 10 or 11.

13. A pharmaceutical composition for use as a medicament, particularly for use in the treatment of immune-mediated diseases amenable to IL-2 immunotherapy, more particularly immune-mediated diseases selected from allograft-related disorders, chronic inflammation, allergy, autoimmunity, and metabolic disease comprising:
    a. the hIL-2-specific mAb, or antigen-binding fragment thereof, according to any one of the items 1 to 9, and
    b. hIL-2.

14. The pharmaceutical composition for use according to item 13, wherein the IL-2 and the hIL-2-specific mAb are covalently associated, particularly wherein the IL-2 and hIL-2-specific mAb are comprised within a hIL-2 fusion protein according to item 10 or 11.

15. The pharmaceutical composition comprising the hIL-2-specific mAb for use according to item 13 or 14, wherein the autoimmune disease is selected from systemic lupus erythematosus, rheumatoid arthritis, ankylosing spondylitis, autoimmune hepatitis, amyotrophic lateral sclerosis, type-1 diabetes mellitus, type-2 diabetes mellitus, atherosclerosis, multiple sclerosis, inflammatory and autoimmune myopathies, alopecia areata, psoriasis or inflammatory bowel disease.

16. The pharmaceutical composition comprising the hIL-2-specific mAb for use according to any of the items 13 to 15, wherein the allograft related disorder is diagnosed in a patient receiving a solid organ transplant procedure.

17. An isolated antibody, or antigen-binding fragment thereof, which binds to a hIL-2 epitope comprising the hIL-2 residues H16, D20, Q57, E60, E61, L63, K64, E67, E68 L80, R81, R83, D84, 186, S87, N88, N90, V91, L94, E95, K97, T101, T102, M104, and wherein the epitope does not comprise the hIL-2 residues M23, G27, N71, Q74, S75, K76, N77, F78, P82.

18. An isolated antibody or antigen-binding fragment thereof, which comprises an antigen recognition surface having epitope recognition characteristics equivalent to an antibody or molecule according to any one of the items 1 to 11.

Background of Dendritic Cell Stimulation by IL-2

Dendritic cells (DCs) are a subgroup of professional antigen-presenting cells considered indispensable in orchestrating T cell responses to intracellular pathogens and tumours (Mildner A. et al. *Immunity,* 2014, 30:1; Durei V. and Murphy K. M. *Immunity* 2014, 40:642). Human blood DCs have traditionally been subdivided into conventional DCs (CDC) and plasmacytoid DCs (pDC); however, results from single-cell RNA and protein analysis identified differentiation into type-1 cDCs (cDC1) that are controlled by interferon-regulatory factor 8 (IRF8) and basic leucine zipper transcriptional factor ATF-like 3 (BATF3) and type-2 cDCs (cDC2) that are controlled by IRF4 in mice and humans (Villani A. C. et al. *Science* 2017, 356:6335; Dutertre C. A. et al. *Immunity* 2019, 51:573, Schraml B. U. and Reis e Souse C. *Curr Opin Immunol* 2015, 32:13). DC subsets in non-lymphoid tissues, including the tumour microenvironment (TME), vary considerably in terms of phenotypic and functional properties (Worbs T. et al. *Nat. Rev. Immunol* 2017, 17:30; Broz M. L. et al. *Cancer Cell* 2014, 26:638). However, the upstream molecular and cellular factors favouring the on-demand generation and expansion of cDCs in anti-tumour responses are ill-defined.

Two studies have implicated NK cells in facilitating DC infiltration of tumours, which correlated with prolonged survival in humans (Bottcher J. P. et al. *Cell* 2018, 172:1022; Barry K. C. et al. *Nat Med* 2018, 24:1178). NK cells are lymphoid cells, and their survival and homeostasis depend on signals mediated through the common gamma chain cytokine receptor (γc, also termed CD132), encoded by Il2rg. Members of the CD132 cytokine family comprise IL-2, IL-4, IL-7, IL-9, IL-15, and IL-21 (Raeber M. E. et al. *Immunol Rev* 2018, 283:176). IL-2 signals either through an intermediate-affinity dimeric IL-2 receptor (IL-2R), comprised of IL-2Rβ (CD122) and CD132, or a trimeric IL-2R additionally including IL-2Rα (CD25). The dimeric receptor is found mainly on memory CD8$^+$ T and NK cells, whereas the trimeric receptor is predominantly found on $T_{reg}$ cells at the steady state and is transiently upregulated on recently activated effector T cells (Arenas-Ramirez J. et al. *Trends Immunol* 2015, 36:763). In addition to its effects on T cells and NK cells, IL-2 can also stimulate innate lymphoid cells (ILC), particularly type 2 ILCs (ILC2), NKT cells, and activated B cells, as well as certain non-immune cells (Malek R. T and Castro I. *Immunity* 2010, 33:153); Abbas A. K. et al. *Sci Immunol* 2018, 3 (25): eaat1482). However, IL-2 is not known to affect DC homeostasis in vivo.

Summary of Dendritic Cell Stimulation by hIL-2 mAb Compositions

Example 5 relates a clinical trial to study immune responses in systemic lupus erythematosus patients receiving IL-2 therapy to induce immune tolerance, where the inventors made an unexpected observation of a prominent increase in several DC subsets. IL-2 immunotherapy studies in both mice and humans demonstrated expansion and activation of DCs by complexes comprising IL-2 and trimeric IL-2R- or IL-2Rα-biased mAb. This pathway is driven by IL-2, and stimulates expansion of both DC populations and DC processes.

A first aspect of the invention is an IL-2 complex pharmaceutical composition for use in patients in need of enhanced dendritic cell function, wherein the IL-2 complex comprises both human hIL-2 and a hIL-2-specific mAb, and the IL-2 complex preferentially binds the high affinity IL-2R or CD25 rather than the intermediate-affinity IL-2R.

In some embodiments, the pharmaceutical composition for use comprises a hIL-2-specific mAb comprising heavy chain variable ($V_H$) region with a $V_H$ complementarity determining region $CDR_H1$, $CDR_H2$ and $CDR_H3$, and a variable light chain ($V_L$) region with a $V_L$ complementarity determining region CDR 1, $CDR_L2$ and CDR 3, and wherein the $CDR_H1$, $CDR_H2$, $CDR_H3$, CDR 1, $CDR_L2$ and $CDR_L3$ comprise, or are identical to SEQ ID NO 001, SEQ ID NO 002, SEQ ID NO 003, SEQ ID NO 004, SEQ ID NO 005, and SEQ ID NO 006 respectively. In further embodiments the CDR are included in a $V_H$ sequence of SEQ NO ID 007, and a Vi sequence of SEQ ID NO 015, or functionally similar sequences. In other embodiments the pharmaceutical composition for use in patients to enhance DC function is biased towards increased $T_{reg}$ activation, and promotes DC activation or proliferation in patients.

The invention further provides a method of treating patient diagnosed with an autoimmune or inflammatory condition, with the IL-2 complex according to the invention.

Detailed Description of Dendritic Cell Stimulation by hIL-2 mAb Compositions

For purposes of interpreting the specification, the definitions provided in the section entitled "Terms and Definitions" continue to apply and whenever appropriate, terms used in the singular will also include the plural and vice versa.

A first aspect of the invention is a pharmaceutical composition for use in a patient with a condition benefiting from enhanced DC function, comprising an IL-2 complex itself comprising both a human IL-2 (hIL-2) polypeptide, and a hIL-2-specific monoclonal antibody (mAb). An example of an appropriate hIL-2-specific mAb is disclosed in US20170114130A1, the contents of which are incorporated herein by reference. The IL-2 complex according to this aspect of the invention preferentially binds to CD25, and/or the high-affinity IL-2 receptor comprising CD122, CD132 and CD25, compared to the intermediate-affinity IL-2R comprising CD122 and CD132.

The data in FIGS. 15 and 17 of the examples demonstrates that both a commercial CD25-biased anti-IL-2 antibody clone 5344, or the UKFA-20 clone described herein, in complex with IL-2 can expand the total number of DC in the spleen at an equivalent level to IL-2 complexes prepared with the CD122-biased anti-IL-2 NARA1 clone. This data suggests that the pharmaceutical composition will provide benefits to patients diagnosed with inflammatory or autoimmune conditions by increasing the number of DCs with a toleragenic phenotype.

An IL-2 complex comprising a CD25-biased mAb will deliver IL-2 signals preferentially to cells expressing abundant CD25 such as $T_{reg}$, which secrete tolerogenic molecules such as IL-10 and transforming growth factor beta. The pharmaceutical composition is therefore expected to be of particular use in patients diagnosed with conditions benefitting from enhanced tolerogenic DC function. A tolerogenic DC may be identified, for example, by a tolerogenic signature including expression of the following genes or their products: CD274, PDCD1LG2, CD200, CD205, FAS, ALDH1A2, SOCS1, SOCS2, IL4R, IL411, IL10, CCL17, CCL22, TNFRSF4 and BCL2L1 (Maier, *Nature* 2020, 580: 257).

In particular embodiments, the hIL-2 and anti-hIL-2 mAb complex according to the invention comprises a hIL-2 polypeptide, non-covalently associated with the anti-hIL-2 mAb according to the invention. The ratio in which the hIL-2, and the hIL-2-specific mAb comprising the IL-2 complex are combined is not particularly limited according to the invention. These hIL-2 mAb complexes have been demonstrated to function effectively when the elements are combined at a 2:1 ratio (Boyman, Science 2006, 311:1924; Krieg, *PNAS* 2010, 107:11906; Arenas-Ramirez, *Sci Transl Med* 2016, 8, 367ra166), or at a 1:1 ratio (Letourneau, PNAS 2010, 107:11906; Arenas-Ramirez, *Sci Transl Med* 2016, 8, 367ra1660). The combination of the two components of the complex is performed in solution, and the time, temperature and conditions of this combination procedure are also not particularly limited according to the invention. The complex may be formed, for example, by combining hIL-2 and the anti-hIL-2 mAb in physiological solution such as phosphate buffered saline at room temperature for 15 minutes. The preparation and activity of IL-2 mAb complexes using mAb that bias IL-2 signalling towards IL-2Rα or IL-2Rβ, and therefore increase STAT5 phosphorylation in $T_{reg}$ or $CD8^+$ T cells has been demonstrated (Letourneau, *PNAS* 2010, 107: 11906; Krieg, *PNAS* 2010, 107:11906; Trotta, *Nat Med* 2018, 24:1005). In other embodiments, the hIL-2 and the anti-hIL-2 mAb of the pharmaceutical composition according to the invention are covalently associated, particularly joined by a peptide linker.

In particular embodiments of the pharmaceutical composition comprising an IL-2 complex for use increases activation, for example measured by STAT5 phosphorylation, and/or proliferation, in regulatory T ($T_{reg}$) cells to a greater extent than it does in $CD8^+$ T cells. In certain embodiments, the pharmaceutical composition for use as specified above increases the ratio of $T_{reg}$ cells to $CD8^+$ T cells, natural killer (NK) cells, innate lymphoid cells (ILC), and/or B cells when applied to a human, or primate immune cells.

The inventors have generated a novel hIL-2-specific mAb UFKA-20, and its humanized derivative UFKA-22. IL-2 complex formed with the mAb highly efficiently and specifically stimulate T cells expressing CD25. The inventors demonstrate that hIL-2-specific mAb according to this aspect of the invention will efficiently expand tolerogenic DC populations compared to other previously described CD122-targeting antibody clones. In particular embodiments, the hIL-2-specific mAb of the IL-2 complex pharmaceutical composition for use in patients comprises a $V_H$ region comprising a $CDR_H1$, $CDR_H2$ and $CDR_H3$, and a $V_L$ region comprising a CDR 1, $CDR_L2$ and $CDR_L3$. According to this embodiment:

$CDR_H1$ comprises, or is identical to SEQ ID NO 001; and $CDR_H2$ comprises, or is identical to SEQ ID NO 002, and $CDR_H3$, comprises, or is identical to SEQ ID NO 003; and $CDR_L1$ comprises, or is identical to SEQ ID NO 004; and $CDR_L2$ comprises, or is identical to SEQ ID NO 005; and $CDR_L3$ comprises, or is identical to SEQ ID NO 006.

In an alternative embodiment, the $CDR_H1$, $CDR_H2$ and $CDR_H3$ of the hIL-2 mAb comprised in the IL-2 complex pharmaceutical complex for use in patients requiring DC enhancement, are comprised in at least one $V_H$ sequence selected from SEQ ID NO 007, SEQ ID NO 008, SEQ ID NO 009, SEQ ID NO 010, SEQ ID NO 011, SEQ ID NO 012, SEQ ID NO 013, or SEQ ID NO 014, or SEQ ID NO 017, particularly wherein the $CDR_H$ are comprised in SEQ ID NO 007. In addition, the CDR 1, $CDR_L2$ and $CDR_L3$ of the hIL-2 mAb are comprised in at least one $V_L$ sequence selected from SEQ ID NO 015, SEQ ID NO 016, or SEQ ID NO 0018, particularly wherein the $CDR_L$ are comprised in SEQ ID NO 015. The isolated antibody hIL-2-specific antibody, or antigen-binding fragment thereof according to this aspect of the invention, binds to a hIL-2 epitope comprising the hIL-2 residues H16, D20, Q57, E60, E61, L63, K64, E67, E68. L80, R81, R83, D84, 186, S87, N88, N90, V91, L94, E95, K97, T101, T102, M104 and excluding the hIL-2 residues M23, G27, N71, Q74, S75, K76, N77, F78, P82. An antibody with the above characteristics in complex with hIL-2 will preferentially deliver IL-2 signals to the high-affinity IL-2R. Importantly it will also dissociate from the complex, in other words, detach from the IL-2 polypeptide upon binding to the receptor, in order to allow delivery of an unimpeded, optimal signalling stimulus without steric hindrance from the antibody.

According to another embodiment, the pharmaceutical composition comprising an IL-2 complex for use according to the invention promotes proliferation and/or activation of DCs in a patient. DC proliferation can be measured by incorporation of a detectable DNA interchelating agent such as Brdu, 7AAD, or by an increase in numbers over time, or by upregulation of a surface marker indicating entry into the cell cycle, such as Ki67. Activation may be defined as an increase in measurements of a factor produced by mature dendritic cells, such as MHC, or co-stimulatory molecules. Alternatively, the activation may be defined by an increase in those molecules shown to drive activation and proliferation of dendritic cells in the examples, particularly tumour necrosis factor (TNF, TNFA, TNFSF2, Uniprot P01375), Fms-related tyrosine kinase 3 ligand (Flt31, UniProt P49771), and granulocyte-macrophage colony stimulating factor (CSF2, UniProt P04141).

The data presented in FIGS. 15 and 17 demonstrate that parenteral administration of an IL-2 complexes comprising a CD25-biased antibody expands the DC populations in the spleen of murine recipients IL-2 complex stimulation induces both proliferation of mature dendritic cells, as measured by BrdU incorporation, and the maturation of DC precursors intoa supressive, measured by modulation of activations markers (FIGS. 15 and 17).

In certain embodiments of the pharmaceutical composition comprising an IL-2 complex for use according the invention, the composition is administered to a patient having been diagnosed with an immune-mediated condition. Autoimmune and autoinflammatory diseases where DC-based treatments may benefit that patient include, but are not limited to, systemic lupus erythematosus, rheumatoid arthritis, Sjögren's disease, type I diabetes, psoriasis, vitiligo, inflammatory bowel diseases, multiple sclerosis, hemophagocytic lymphohistiocytosis. In addition, the importance of dendritic cells in priming and sustaining T cell responses suggests that patients diagnosed with an allergic or atopic disorders such as asthma or atopic dermatitis may also benefit from administration of the pharmaceutical composition comprising an IL-2 complex according to the invention.

In an alternative embodiment, the pharmaceutical composition comprising an IL-2 complex for use according to the invention is administered to a patient diagnosed with an allotransplant related disorder (for example, acute and chronic graft-versus-host disease, or vasculitis such as granulomatosis with polyangiitis). In addition, it may be administered in order to encourage future allograft acceptance in transplantation. Administration of the pharmaceutical composition comprising an IL-2 complex may thus occur prior, or concurrent to an allogenic tissue graft or organ transplantation procedure, or after a patient previously received a tissue graft or organ transplantation procedure.

FIG. 16 of the examples demonstrates that IL-2 immunotherapy with aldesleukin expands dendritic cells in human systemic lupus erythematosus patients, with particular enhancement of cDC1 and cDC2 numbers. FIGS. 15 and 17 show that treatment with an IL-2 complex comprising NARA1, or a CD25-biased pharmaceutical composition comprising an IL-2 complex according to the invention achieves similar acute DC expansion in mice. Furthermore, IL-2 complexes as provided by the invention, are known to be superior to IL-2 immunotherapy in terms of efficacy, reduced side-effects, and longevity of response (Arenas-Ramirez J. et al. *Trends Immunol* 2015, 36:763). CD25 biased hIL-2-specific mAb complexes are demonstrated to enhance DC with a tolerogenic phenotype, characterised by reduced CD80 and MHC II expression, and upregulation of the PD-1 family of checkpoint inhibition molecules.

A further aspect of the invention is a method for treating a patient in need of enhanced DC function, such as a patient with cancer, or an autoimmune, inflammatory or allograft-related condition, comprising administering an effective amount of the pharmaceutical composition comprising a hIL-2 polypeptide in association with a hIL-2-specific mAb according the specifications of the invention.

The invention further encompasses the following additional items:

A. A pharmaceutical composition comprising an IL-2 complex, wherein the IL-2 complex comprises a human IL-2 (hIL-2) polypeptide associated with a hIL-2-specific monoclonal antibody (mAb), and wherein the IL-2 complex preferentially binds to CD25, and/or a high-affinity IL-2 receptor comprising CD122, CD132 and CD25, compared to an intermediate-affinity IL-2R comprising CD122 and CD132, for use in a patient with a condition benefiting from enhanced dendritic cell (DC) function.

B. The pharmaceutical composition comprising an IL-2 complex for use according to item A, wherein the IL-2 complex a. increases STAT5 phosphorylation in regulatory T ($T_{reg}$) cells to a greater extent than it increases STAT5 phosphorylation in CD8$^+$ T cells, and/or b. increases proliferation of $T_{reg}$ cells to a greater extent than it increases proliferation of CD8$^+$ T cells, and/or c. increases the ratio of $T_{reg}$ cells to CD8$^+$ T cells, natural killer (NK) cells, innate lymphoid cells (ILC), and/or B cells.

C. The pharmaceutical composition comprising an IL-2 complex for use according to item A or B, wherein the hIL-2-specific mAb comprises a heavy chain variable (VA) region comprising a $V_H$ complementarity determining region (CDR$_H$) CDR$_H$1, CDR$_H$2 and CDR$_H$3, and a light chain variable ($V_L$) region comprising a $V_L$ complementarity determining region (CDR$_L$) CDR$_L$1, CDR$_L$2 and CDR$_L$3, and wherein:

a. CDR$_H$1 comprises, or is identical to SEQ ID NO 001; and b. CDR$_H$2 comprises, or is identical to SEQ ID NO 002, and c. CDR$_H$3, comprises, or is identical to SEQ ID NO 003; and d. CDR$_L$1 comprises, or is identical to SEQ ID NO 004; and e. CDR$_L$2 comprises, or is identical to SEQ ID NO 005; and f. CDR$_L$3 comprises, or is identical to SEQ ID NO 006.

D. The pharmaceutical composition comprising an IL-2 complex for use according to any one of the items A to C, wherein c. the CDR$_H$1, CDR$_L$2 and CDR$_H$3 of the hIL-2 mAb are comprised in a $V_H$ sequence selected from SEQ ID NO 007, SEQ ID NO 008, SEQ ID NO 009, SEQ ID NO 010, SEQ ID NO 011, SEQ ID NO 012, SEQ ID NO 013, or SEQ ID NO 014, particularly wherein the CDR$_H$ are comprised in SEQ ID NO 007, and wherein, d. the CDR 1, CDR$_L$2 and CDR$_L$3 of the hIL-2 mAb are comprised in a $V_L$ sequence selected from SEQ ID NO 015, or SEQ ID NO 016, particularly wherein the CDR$_L$ are comprised in SEQ ID NO 015.

E. The pharmaceutical composition comprising an IL-2 complex for use according to any one of the items A to D, wherein the pharmaceutical composition promotes proliferation and/or activation of DCs in a patient.

F. The pharmaceutical composition comprising an IL-2 complex for use according to any one of the items A to E, wherein the composition is administered to a patient having been diagnosed with an immune-mediated condition.

G. The pharmaceutical composition comprising an IL-2 complex for use according to any one of the items A to F, wherein the composition is administered to a patient prior to an allogenic tissue graft or organ transplantation procedure, or to a patient that has previously received a tissue graft or organ transplantation procedure.

H. A method for treating a patient with cancer, an auto-immune, inflammatory or allograft-related condition comprising administering an effective amount of the pharmaceutical composition comprising a hIL-2 poly-peptide in association with a hIL-2-specific mAb according to any of the items A to G.

The invention is further illustrated by the following examples and figures, from which further embodiments and advantages can be drawn. These examples are meant to illustrate the invention but not to limit its scope.

DESCRIPTION OF THE FIGURES

FIG. 3 Wild-type (WT) C57BL/6 mice were injected with IL-2 (1.5 μg or 30 μg) and IL-2/anti-IL-2 complexes (1.5 μg/15 μg) on days 0, 1, and 2, and euthanized on day 4 to determine cell subset frequencies in lymph nodes and spleens by flow cytometry. (A) Frequencies of CD8$^+$CD44$^{hi}$ CD122$^+$ T cells in lymph nodes and spleens on day 4. (B) Frequencies of splenic CD3-NK1.1+CD122$^+$NK cells.

Figure 1:
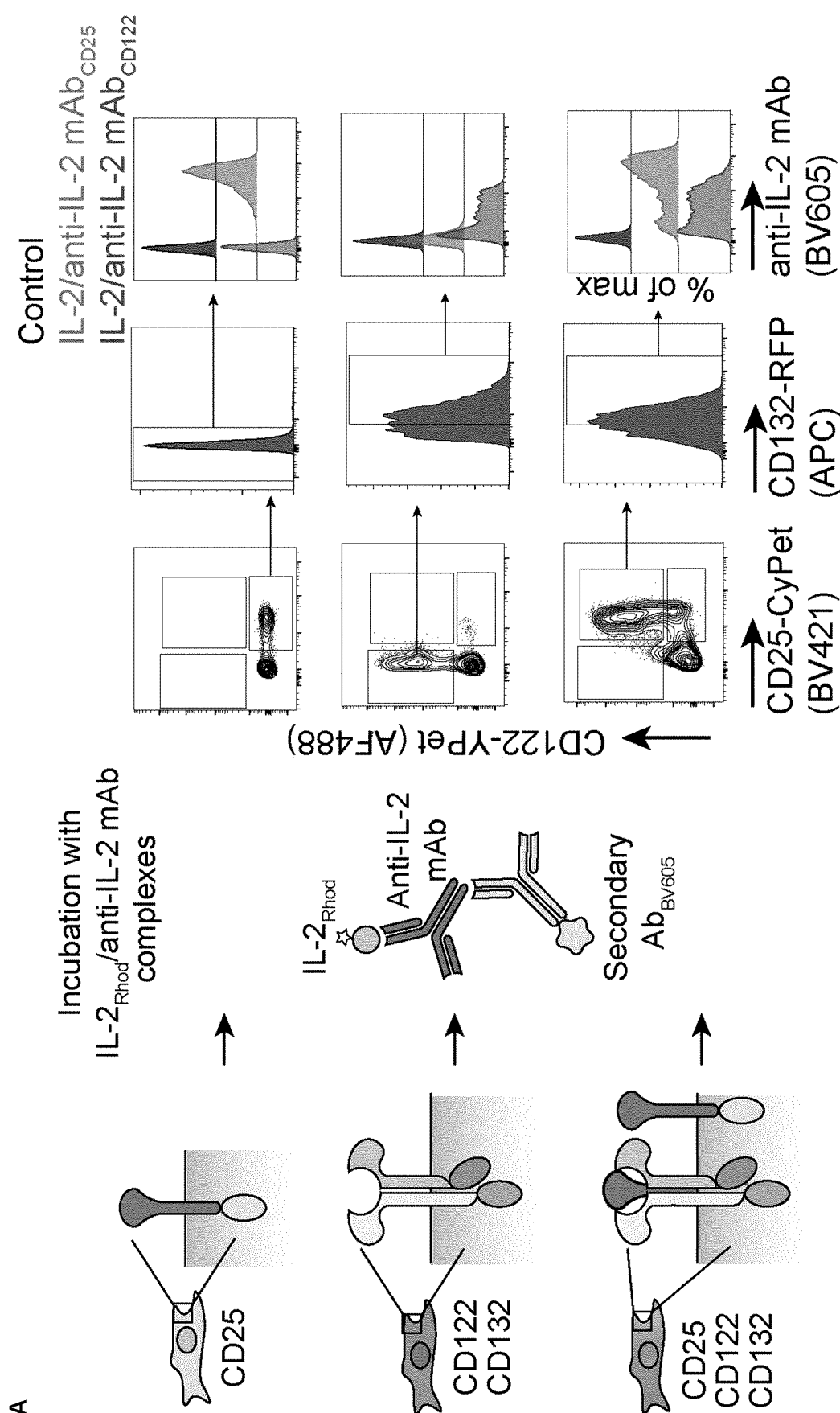
FIG. 1(A) Screening design to identify IL-2 receptor (IL-2R)-biasing anti-hIL-2 mAbs with in vivo agonistic properties. Cell-based IL-2R binding assay and flow cytometry plots of cells expressing CD25, CD122$^+$CD132 or CD25$^+$CD122$^+$CD132, gated based on their fluorescent "barcode". Emission spectra of CD25-CyPet, CD122-YPet and CD132-RFP were detected in the AF488, BV421 and APC channels respectively. IL-2 complex (IL-2cx) binding was recorded in the BV605 channel using a rat anti-mouse IgG-BV605. Histograms (right) show binding of IL-2/anti-IL-2 mAb$_{CD25}$ (middle), IL-2/anti-IL-2 mAb$_{CD122}$ (bottom) and negative control (top). (B) Quantification of IL-2cx-binding as in (A). Readout is the geometric mean fluorescence intensity (gMFI) of BV605 quantified on cells expressing CD25 (white bars) or CD122$^+$CD132 (gray bars) and plotted individually for each anti-IL-2 mAb. Pooled data from 3-4 experiments±SEM. gMFI background was subtracted. Unpaired t-test, two-tailed. (C) Quantification of flow cytometry of IL-2$_{Rhod}$ (PE channel) and anti-IL-2 mAb (rat anti-mouse IgG-BV605) binding to HEK293T cells expressing CD25-CyPet, CD122-YPet+CD132 RFP or CD25-CyPet+CD122-YPet+CD132-RFP, gated as in (A). Control cells were incubated without IL-2$_{Rhod}$. Bar graphs represent frequencies±SEM of IL-2$_{Rhod}$ positive (unfilled) or IL-2$_{Rhod}$/anti-IL-2 mAb double positive (filled) fractions. Pooled data from 3-4 experiments. (D) Matrix of IL-2$_{Rhod}$/anti-IL-2 mAb cx clustered based on their binding to CD25 (Y-axis) or CD122$^+$CD132 (X-axes) (left plot), and CD25 (Y-axis) or CD25$^+$CD122$^+$CD132 (X-axis) (right plot). Mean percentages of IL-2$_{Rhod}$/anti-IL-2 mAb cx positive population obtained in (C). (E) Comparison of complexed and free IL-2$_{Rhod}$ upon incubation with cells expressing the trimeric high affinity IL-2R. Mean percentages of IL-2$_{Rhod}$ versus IL-2$_{Rhod}$/anti-IL-2 mAb complex positive populations obtained in (C). (F) Matrix of "CD25 bias" and "IL-2 delivery" of indicated anti-IL-2 mAb clones. Cluster shows IL-2$_{Rhod}$/anti-IL-2 mAb cx binding to CD25-binding (Y-axis) versus free IL-2$_{Rhod}$ binding to CD25$^+$CD122$^+$ CD132 (X-axis). Mean percentages of IL-2Rhod/anti-IL-2 mAb cx positive and IL-2$_{Rhod}$ positive populations obtained in (C) are displayed. (G) Difference or Ratio between IL-2$_{Rhod}$/anti-IL-2 cx-binding to CD25 and CD25$^+$CD122$^+$ CD132, indicating anti-IL-2 mAb release. (H) Summary of tested anti-IL-2 mAb clones.
Figure 1:
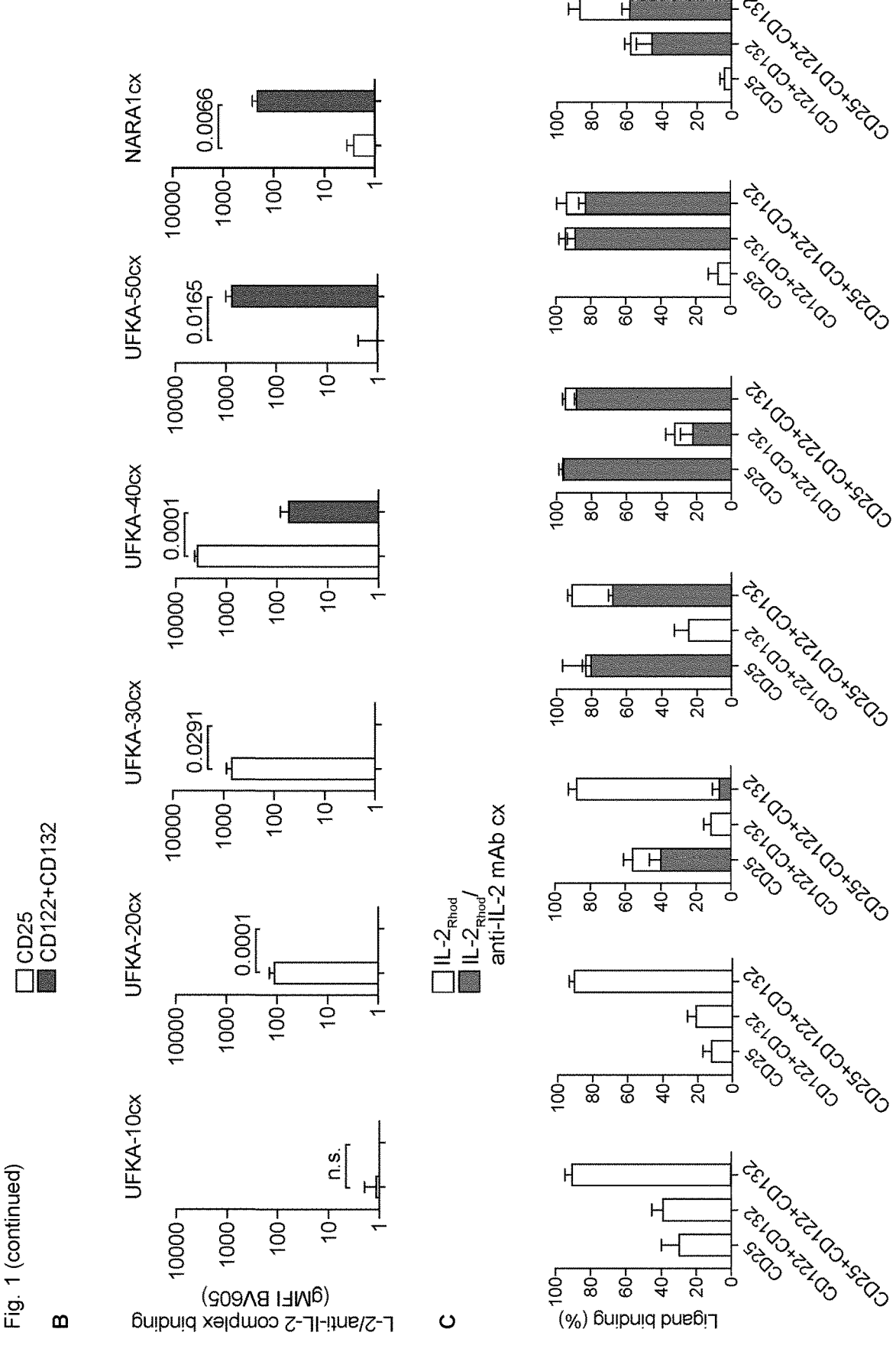
Figure 1:
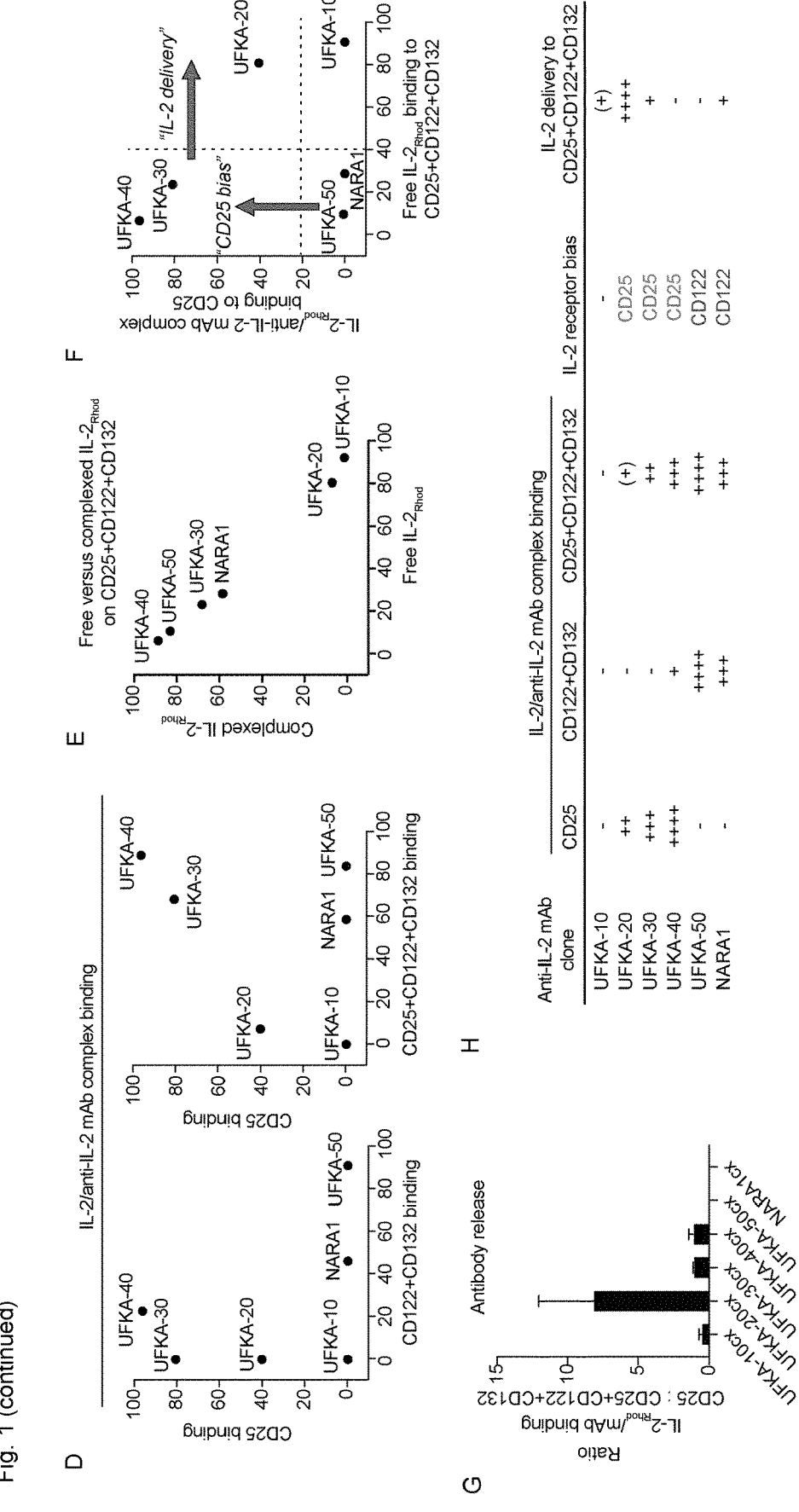

Mean values±SEM from 2-3 experiments, n=2 for IL-2 (30 µg) and UFKA-50; n=5 for IL-2 (1.5 µg), UFKA-10, UFKA-30, UFKA-40, and NARA1; n=6 for PBS and UFKA-20. Red dashed lines represent mean values obtained in IL-2 (1.5 pg)-treated animals.

FIG. 4A single dose of IL-2 (1 µg or 30 µg) or IL-2/UFKA-20 complexes (1 µg/10 µg) was injected into C57BL/6. (A) Mice were euthanized and the frequency of phosphorylated STAT5$^+$ (pSTAT5) cells among splenic CD4$^+$CD25$^+$, CD8$^+$ T and NK cells was measured by flow cytometry after 2 hours (2 hr), on day 1 (d1), day 2 (d2), day 4 (d4), and day 8 (d8) after injection with PBS (gray), IL-2 (1 µg, white), IL-2 (30 µg, black) or IL-2/UFKA-20 complex (dark grey). Data are represented as mean±SEM of three independent experiments, n=5 mice per group. One-way ANOVA with Tukey's multiple comparison test. (D) Cell counts of splenic CD4$^+$CD25$^+$Foxp3$^+$, CD8$^+$ T and NK cells displayed as fold change to PBS. Data are represented as mean±SEM of 3 independent experiments, n=5 mice per group. One-way ANOVA with Tukey's multiple comparison test.

Figure 5:
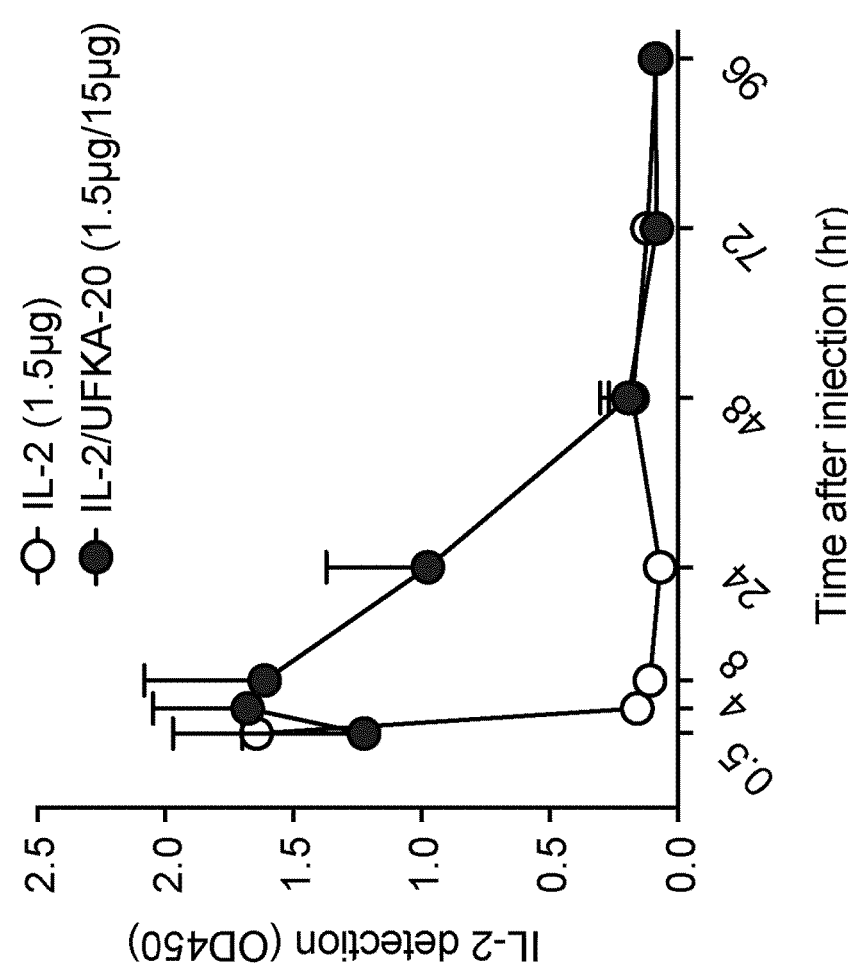

FIG. 5 Wild-type (WT) C57BL/6 mice received a single injection of IL-2 (1.5 µg; open symbols), IL-2/UFKA-20 complexes (IL-2/UFKA-20cx; closed black symbols) or IL-2/UFKA-22 complexes (IL-2/UFKA-22cx; closed red symbols). IL-2/UFKA-20cx and IL-2/UFKA-22cx were generated by complexing human IL-2 (1.5 µg) with UFKA-20 (15 µg) and UFKA-22 (15 µg), respectively, at a 1:1 molar ratio. Blood samples were collected at indicated time points (in hours, hr) after injection, and human IL-2 was detected in serum using a sandwich enzyme-linked immunosorbent assay (ELISA). Half-life ($t_{1/2}$) values were calculated by fitting exponential, one-phase decay curves. Shown are mean values of n=7 for IL-2, n=9 for IL-2/UFKA-20cx, and n=3 for IL-2/UFKA-22cx.

Figure 6:
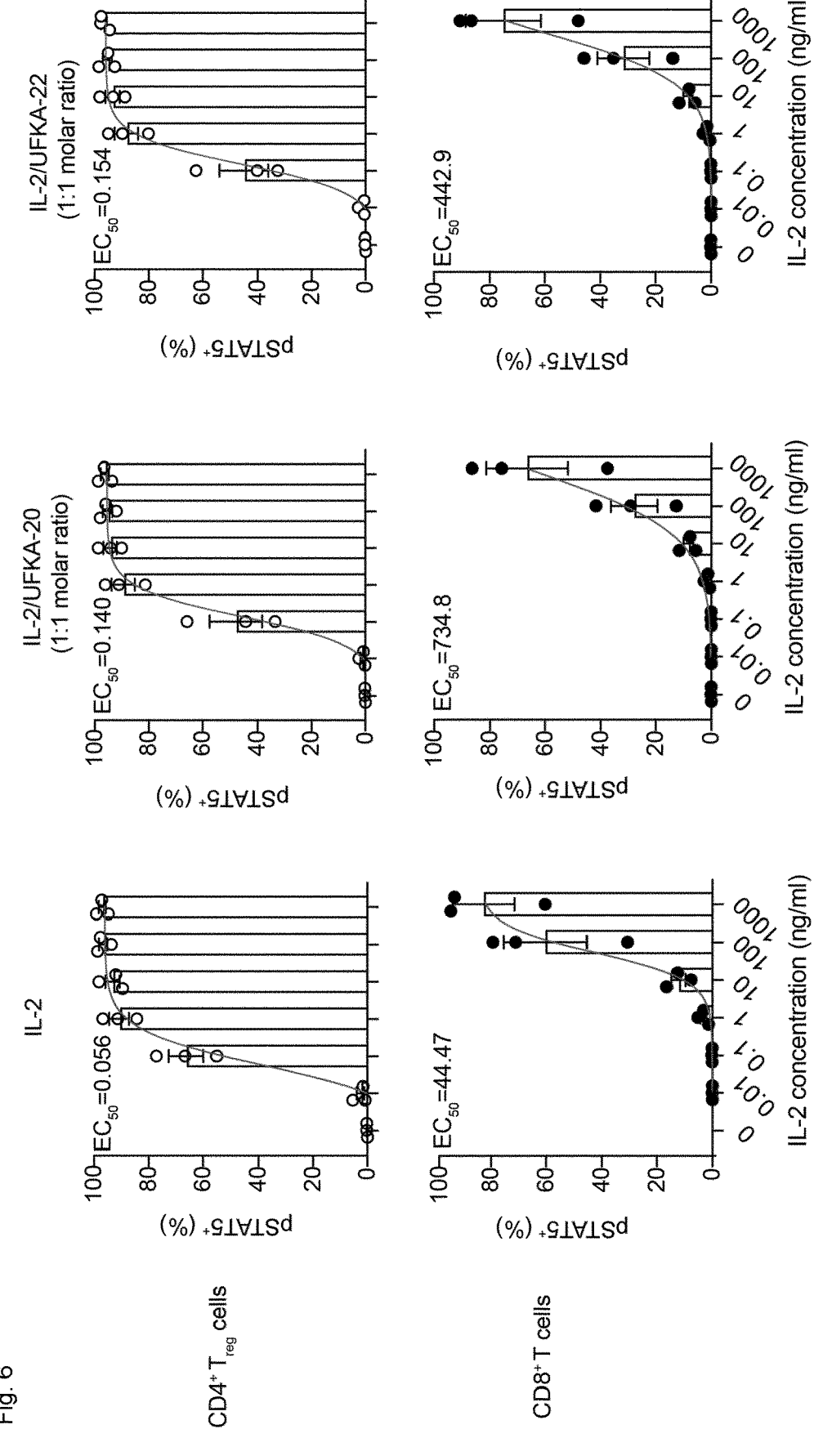

FIG. 6 Quantification of IL-2 cx stimulation of pSTAT5 in human CD4$^+$CD127low Foxp3$^+$ $T_{reg}$ and CD8$^+$ T cells measured by flow cytometry. 100 ng/ml IL-2 was complexed at a 1:1 molar ratio with UFKA-20 or UFKA-22. The pSTAT5 levels on indicated human T cell subsets responding to titrated IL-2 (left graphs), IL-2/UFKA-20cx (middle graphs) and IL-2/UFKA-22cx (right graphs). Half maximal effective concentrations (EC50) were calculated for each condition in both CD4$^+$CD127low Foxp3$^+$ $T_{reg}$ (open symbols) and CD8$^+$ T cells (closed symbols). Fitted dose-response curves are shown as lines. Data are represented as mean±SEM of three independent experiments.

Figure 2:
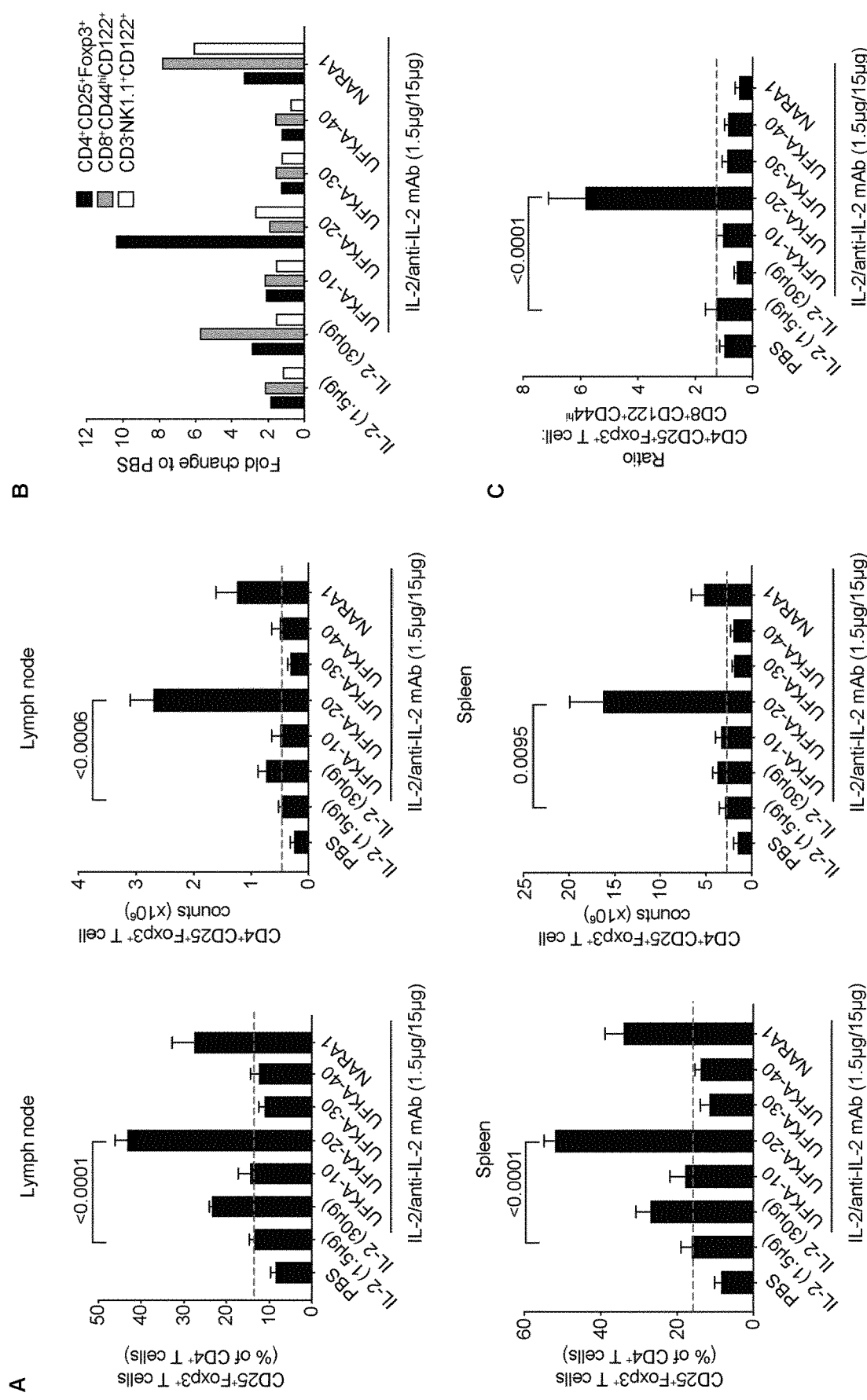
FIG. 2(A) C57BL/6 mice injected with IL-2 (1.5 μg or 30 μg) and IL-2/anti-IL-2 complexes (1.5 μg/15 μg) on days 0, 1 and 2, euthanized on day 4, and frequencies of CD4+ CD25$^+$Foxp3$^+$ T cells and CD8$^+$CD44$^{hi}$ CD122$^+$ T cells were analysed in lymph nodes (LN) and spleens using flow cytometry. (A) Frequency and counts of CD4$^+$CD25$^+$ Foxp3$^+$ T cells in spleens and LNs quantified on day 4. Shown are mean values±SEM from 2-3 experiments, n=2 for IL-2 (30 μg) and UFKA-50; n=5 for IL-2 (1.5 μg), UFKA-10, UFKA-30, UFKA-40, NARA1; n=6 for PBS and UFKA-20. Unpaired t-test, two-tailed. (B) Mean cell counts of CD4$^+$CD25$^+$Foxp3$^+$ T cells, CD8$^+$CD44$^{hi}$ CD122$^+$ T cells, and CD3-NK1.1$^+$CD122$^+$ from spleens are shown as fold changes to PBS-treated mice. (C) Ratios of splenic CD4$^+$CD25$^+$Foxp3$^+$ T and CD8$^+$CD44$^{hi}$ CD122$^+$ T cell counts are plotted. Mean values±SEM. Unpaired t-test, two-tailed. Red dashed lines represent mean values, obtained from IL-2 (1.5 μg)-treated animals.

FIG. 7(A) Experimental setup as described in FIG. 2. Mice received three injections of PBS, IL-2 (1 µg) alone or in complex (1:1 molar ratio) with a chimeric UFKA-20 mAb (chUFKA-20) or the humanized UFKA-20 variants UFKA-22-00 (referred to as UFKA-22), UFKA-22-02, and UFKA-22-07. Mice were euthanized on day 4, frequencies of CD4$^+$CD25$^+$Foxp3$^+$ T cells and CD8$^+$CD44$^{hi}$ CD122$^+$ T cells were analysed in spleens using flow cytometry. Frequency and counts of CD4$^+$CD25$^+$ Foxp3$^+$ T cells in spleens were quantified on day 4. (B) Ratios of splenic CD4$^+$CD25$^+$ Foxp3$^+$ T and CD8$^+$CD44$^{hi}$ CD122$^+$ T cell counts are plotted. Mean values±SEM from 3 experiments, n=3 for PBS, IL-2, and UFKA-22-07; n=5 for UFKA-20, chUFKA-20, UFKA-22-02 and UFKA-22-07.

Figure 8:
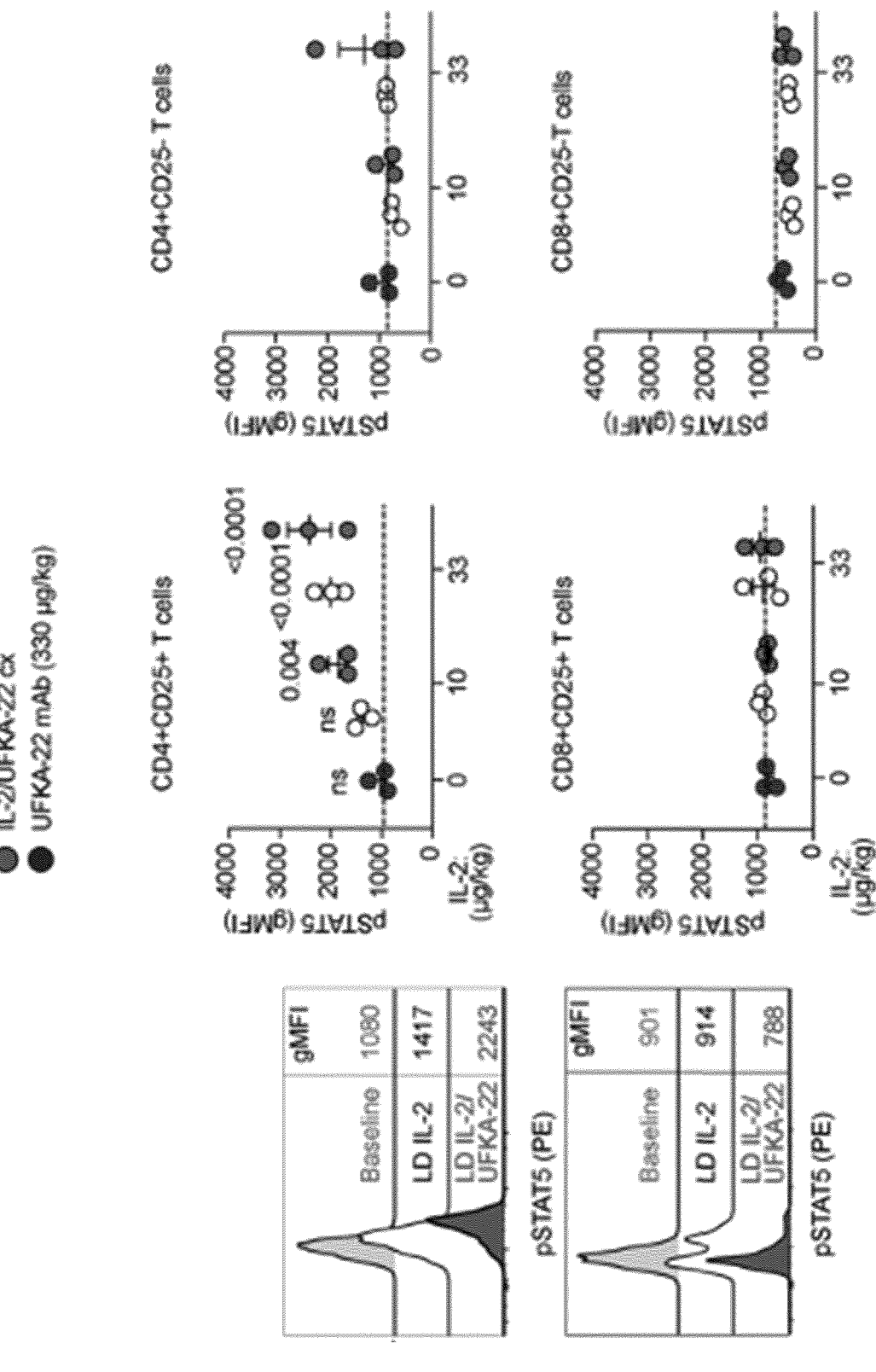
Figure 8:
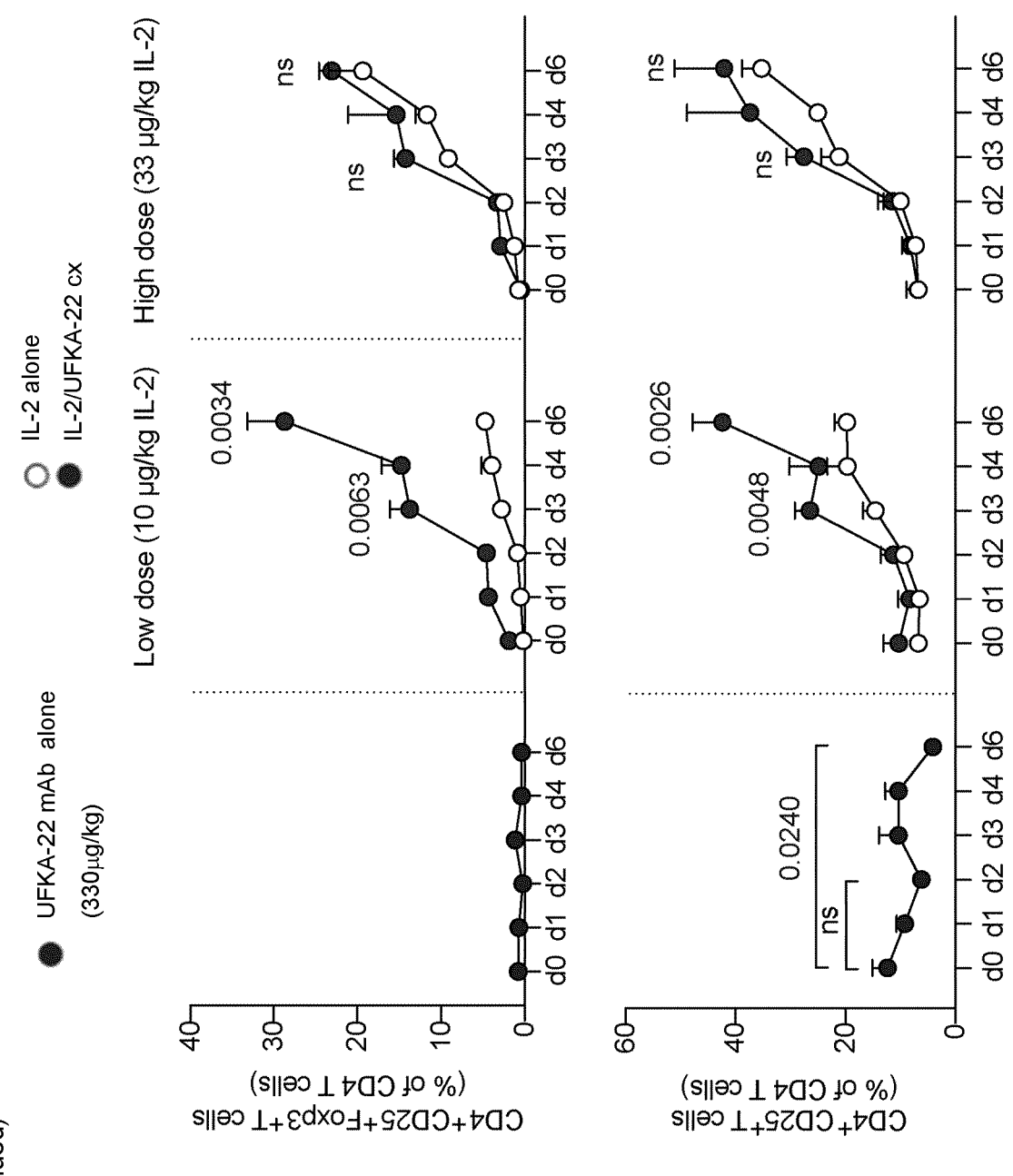

FIG. 8(A) Rhesus macaques received daily injections of IL-2 until day 6 or two injections of IL-2/UFKA-22 complexes or UFKA-22 mAb only on days 0 and 3. Blood was drawn and analysed at indicated timepoints. IL-2 and IL-2/UFKA-22 complex treatment groups were subdivided into two groups receiving low-dose (LD) or high-dose (HD) treatment, corresponding to 10 µg/kg or 33 µg/kg IL-2, respectively, whereas UFKA-22 mAb alone was injected at a dose of 330 µg/kg. EC50s of UFKA-20 (left table) and UFKA-22 (right table) towards human IL-2 and rhesus macaque IL-2 were determined using an IL-2 sandwich ELISA. (B) Representative flow cytometry plots of pSTAT5+ cells in CD4$^+$CD25$^+$ and CD8$^+$CD25$^+$ T cells in blood. Histograms of pSTAT5 levels at baseline measured on day-8 (top), and upon LD IL-2 (middle) and LD IL-2/UFKA-22 (bottom) treatment on day 1, n=3 per group. (C) Frequency of CD4$^+$CD25$^+$Foxp3$^+$ and CD4$^+$CD25$^+$ T cell populations in blood during the study period measured by flow cytometry. (D) gMFI of Foxp3, CTLA-4 and Ki-67 on CD4$^+$CD25$^+$ T cells at indicated time points in blood measured by flow cytometry. For (C) and (D) means±SEM are plotted as white dots (IL-2 treatment group), grey dots (IL-2/UFKA-22 complex treatment group), and dark grey dots (UFKA-22 mAb treatment group). Significance was determined by unpaired t-test, two-tailed, on day 6. ns, not significant. (E) Ratio of $T_{reg}$ (CD4$^+$CD25$^+$Foxp3$^+$ CD4 T) cells to CD8$^+$ T, NK and B cells counts on day 6. Means±SEM and individual values are plotted. Significance determined by one-way ANOVA, Dunnett's multiple comparison. ns, not significant.

Figure 9:
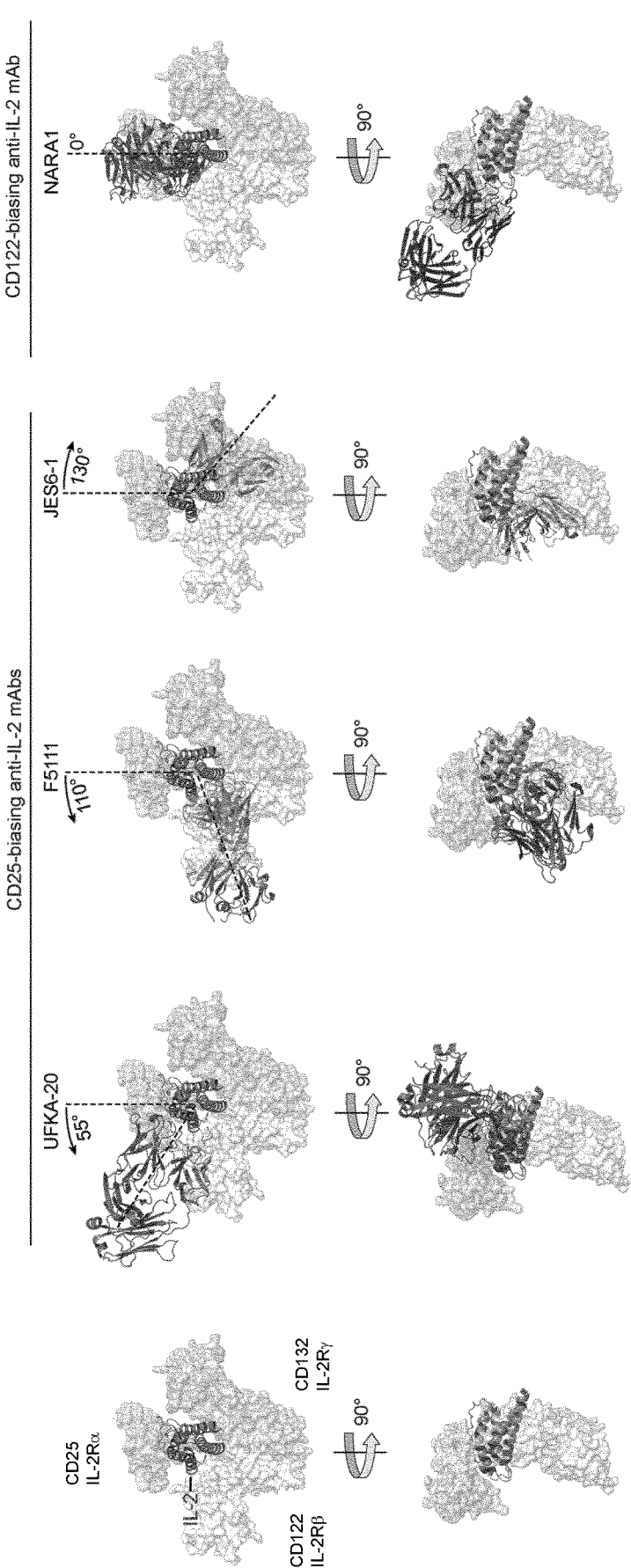
Figure 9:
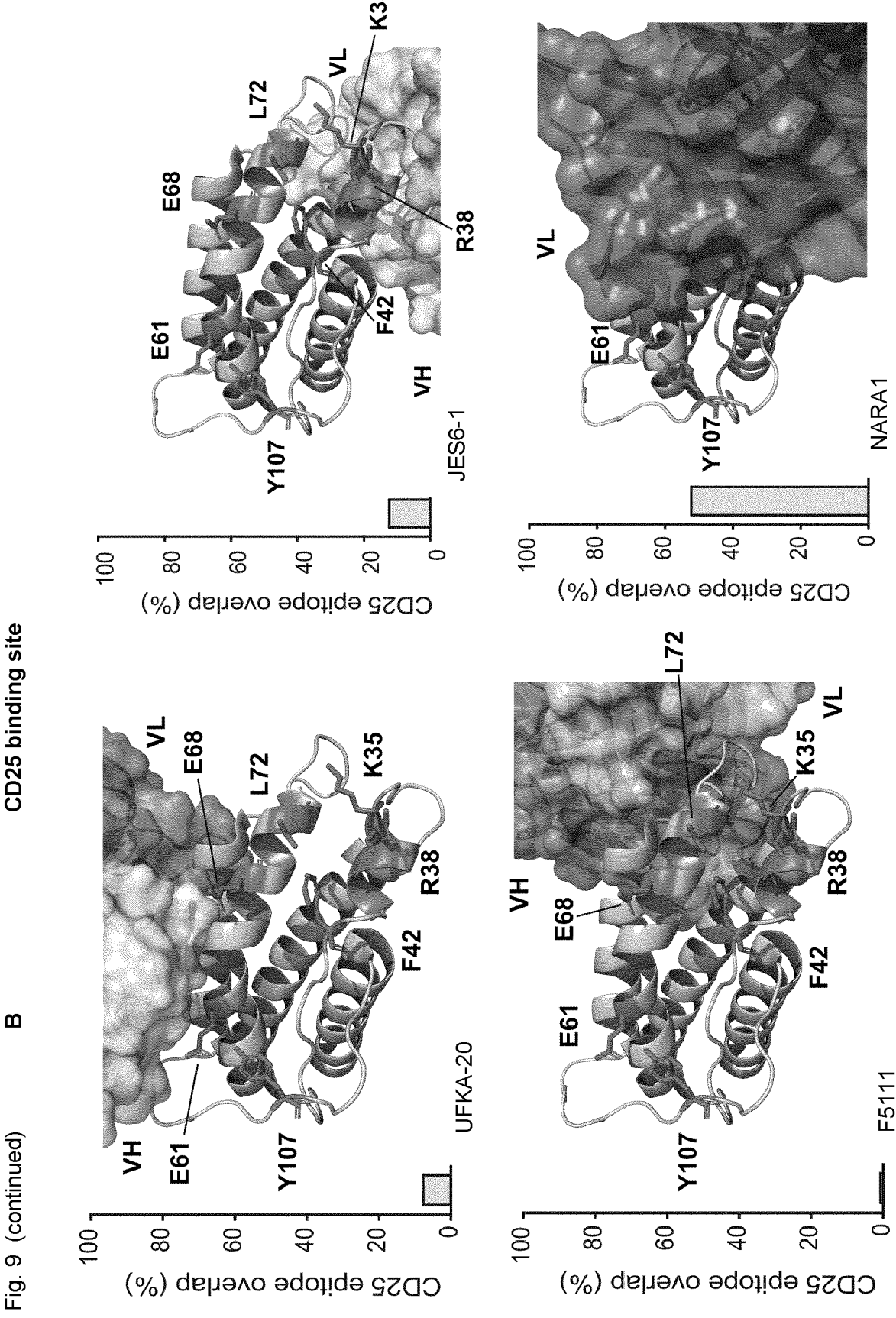
Figure 9:
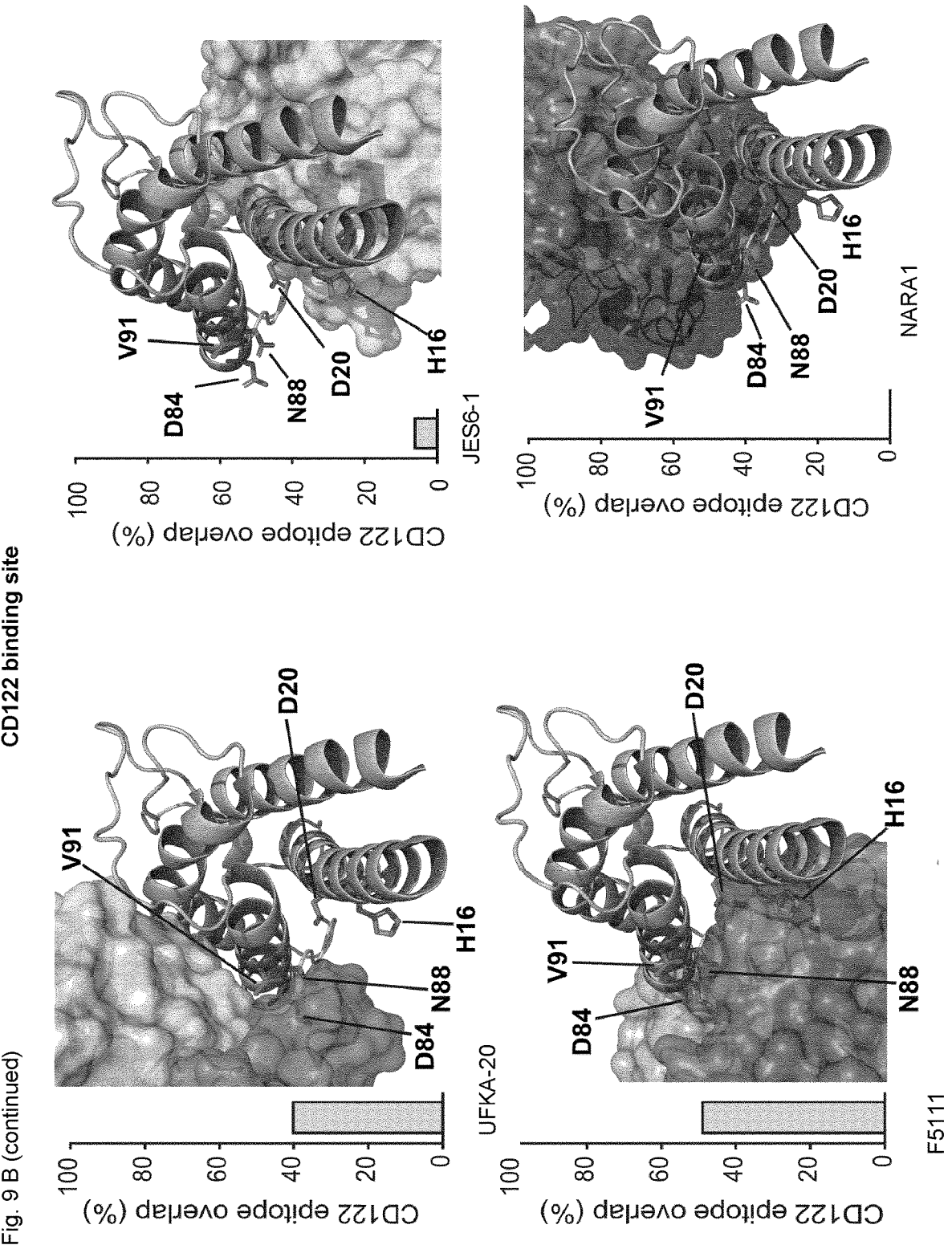
Figure 9:
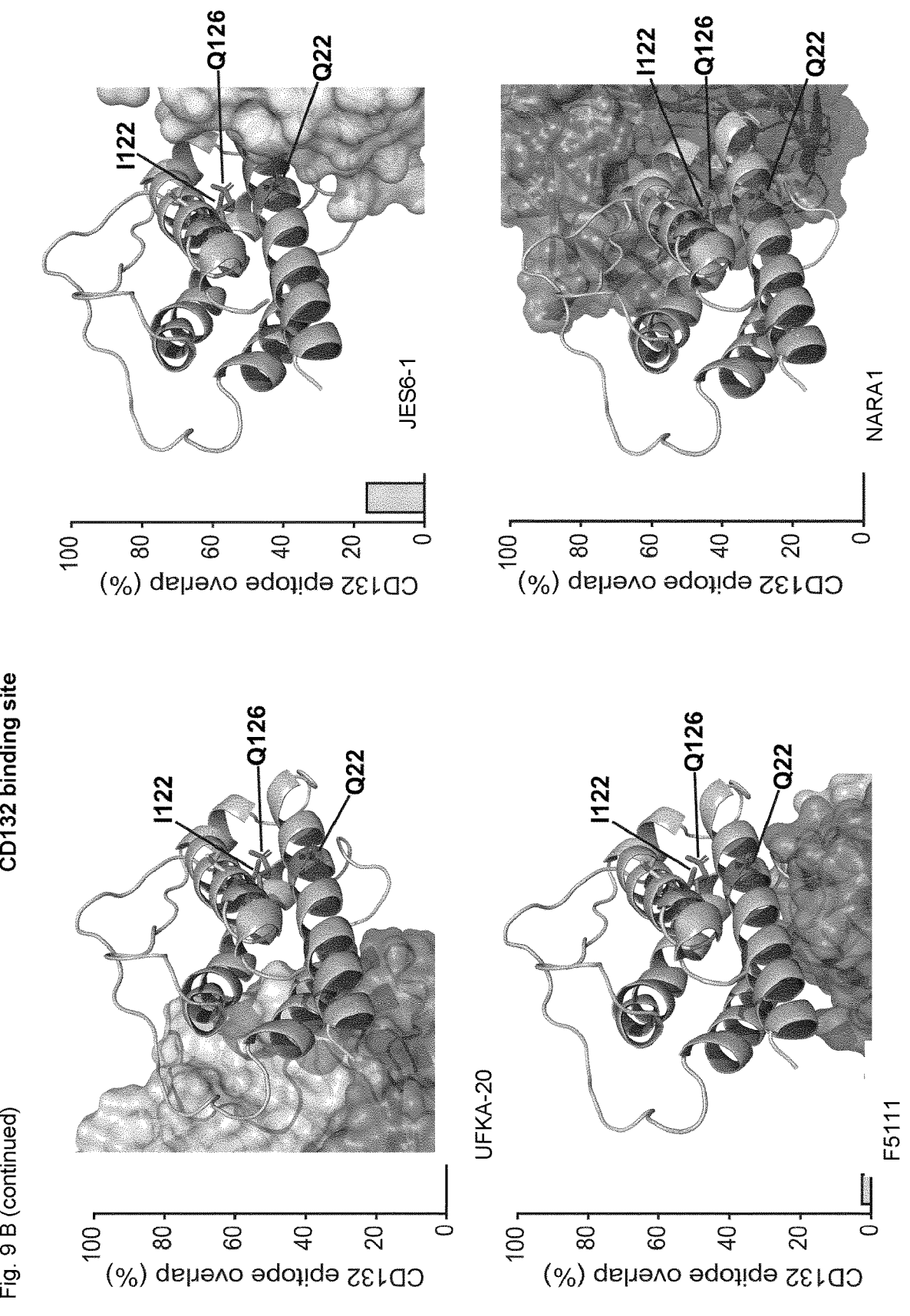
Figure 9:
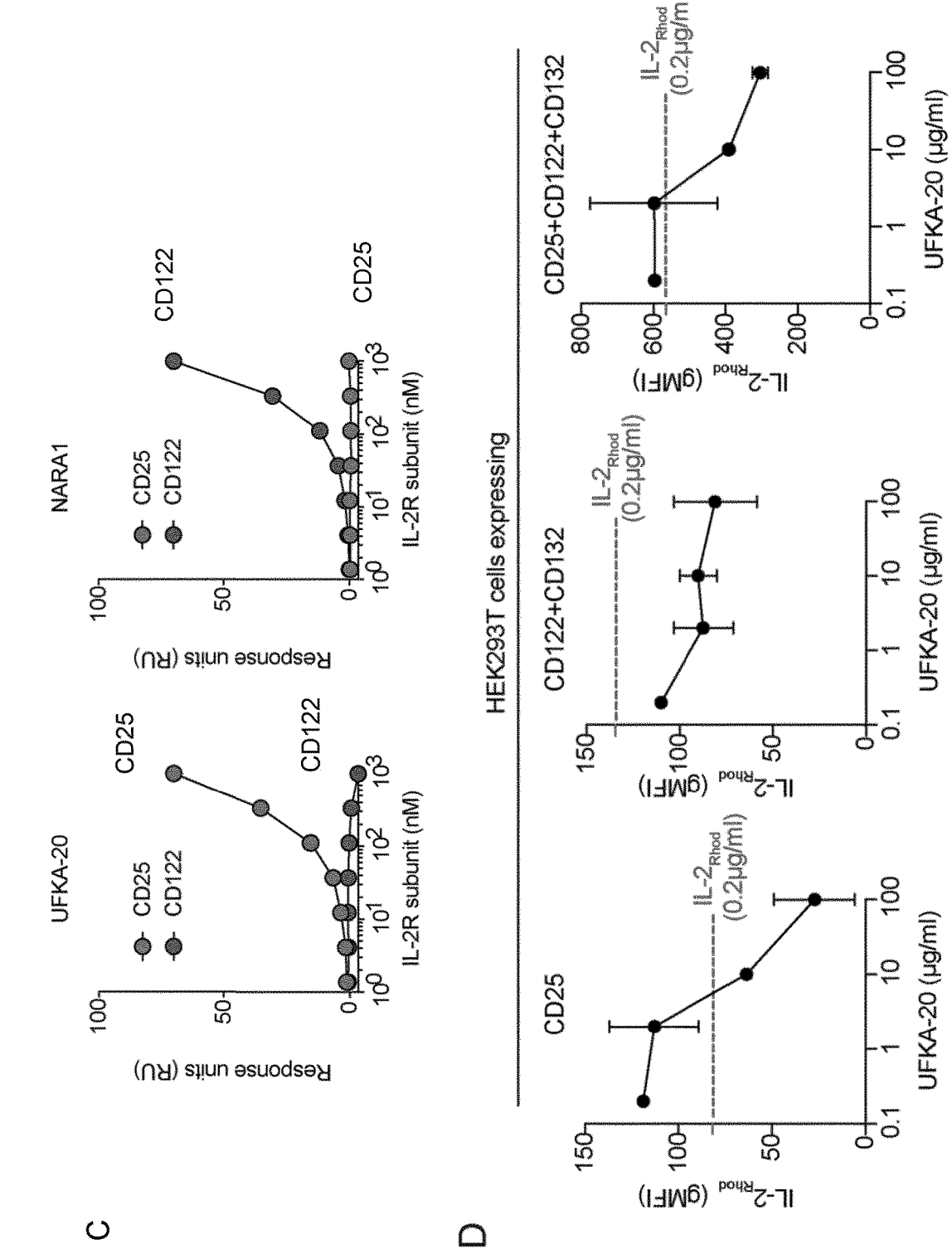

FIG. 9(A) Front and 90°-turned side view of IL-2/anti-IL-2 mAb complex structures superimposed on the human quaternary IL-2R complex comprised of IL-2 (purple), CD25 (IL-2Ra, light orange), CD122 (IL-2RB, white) and CD132 (IL-2Ry, gray). Comparison of IL-2-IL-2R complex (PDB: 2B51); IL-2/UFKA-20 complex (PDB: 6YE3); IL-2/F5111 complex (PDB: 5UTZ); IL-2/JES6-1 complex (PDB: 4YQX); IL-2/NARA1 complex (PDB: 5LQB). (B) Equilibrium surface plasmon resonance (SPR) quantification of IL-2-IL-2R binding epitope overlaps with IL-2/anti-IL-2 complexes. CD25$^-$, CD122- and CD132-binding sites. Bar graphs indicate the relative overlap between antibody and receptor epitope, calculated based on the buried surface area ($Å^2$) using PDBePISA. (C) SPR titration of CD25 and CD122 on IL-2 captured by immobilized UFKA-20 or NARA1, as indicated. Data are representative of 3 experiments. RU, resonance units. (D) IL-2 competition between UFKA-20 and CD25$^-$, CD122$^+$CD132- and CD25$^+$CD122$^+$ CD132-expressing HEK293T cells. A fixed concentration of IL-2$_{Rhod}$ (0.2 µg/ml) was mixed with titrated amounts of UFKA-20 and incubated with IL-2R-expressing HEK293T cells. Mean±SEM of 2 experiments are plotted.

Figure 10:
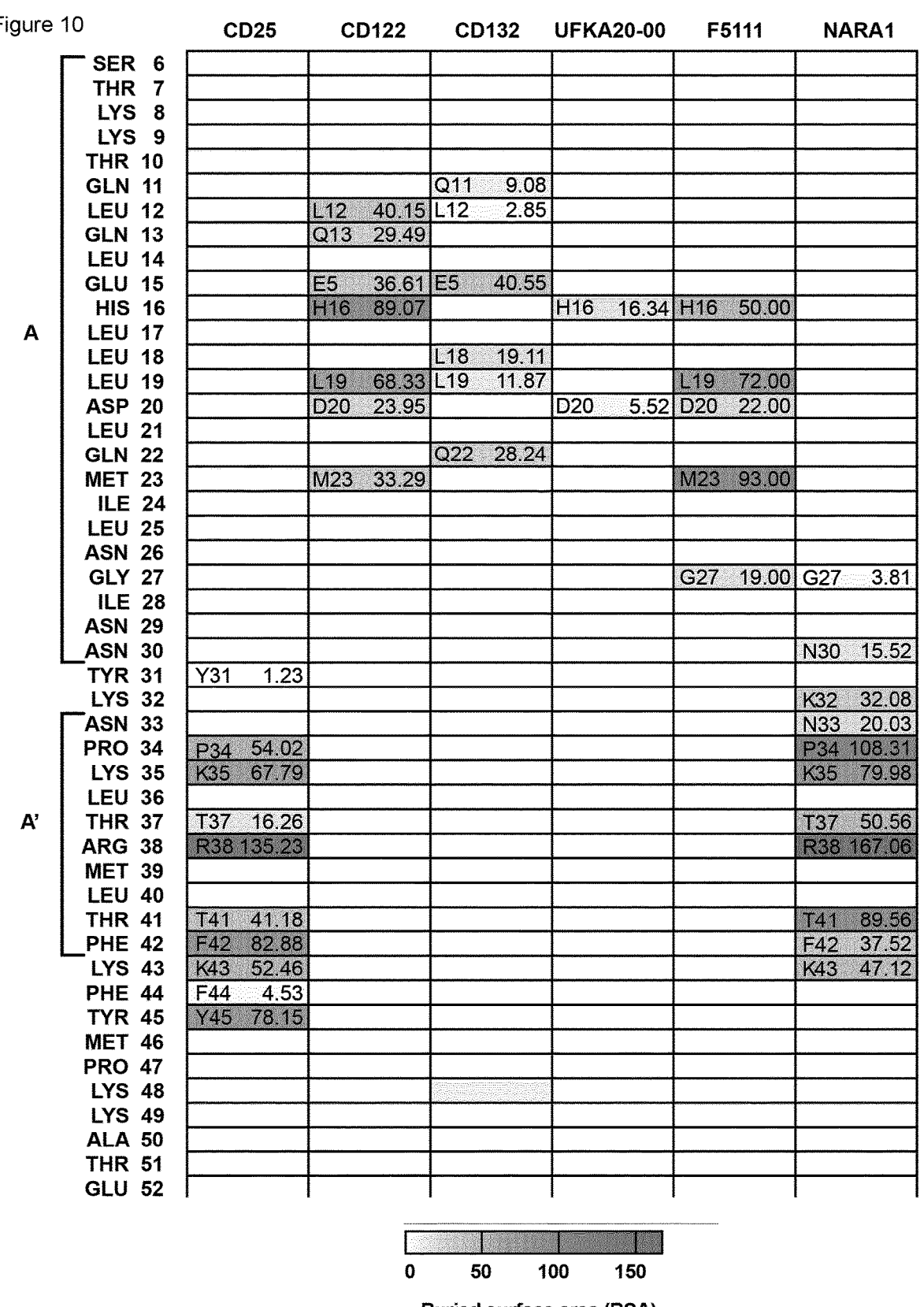

FIG. 10 Buried surface area (BSA) in square angstrom ($Å^2$) between human IL-2 and CD25, CD122, CD132, UFKA-20-00, F5111 and NARA1. Calculated using PDBePISA server and crystal structures of the quaternary IL-2-IL-2R complex (PDB: 2B51), IL-2/UFKA-20-00 complex (PDB: 6YE3), and IL-2/F5111 complex (PDB: 5UTZ). 3-letter amino acid code of the human IL-2 protein sequence with annotated helices A, A', B, B', C and D (Arenas-Ramirez et al. 2015). BSA values (above 0.00 $Å^2$) for amino acid residues of human IL-2 and their ligands (CD25, CD122, CD132, UFKA-20-00, F5111, NARA1) are shown. In addition, the one-letter amino acid code of the affected amino acid residue is indicated.

FIG. 11 Predicted Buried surface area in square angstrom ($Å^2$) showing the predicted UFKA20 binding site on hIL-2.

Figure 12:
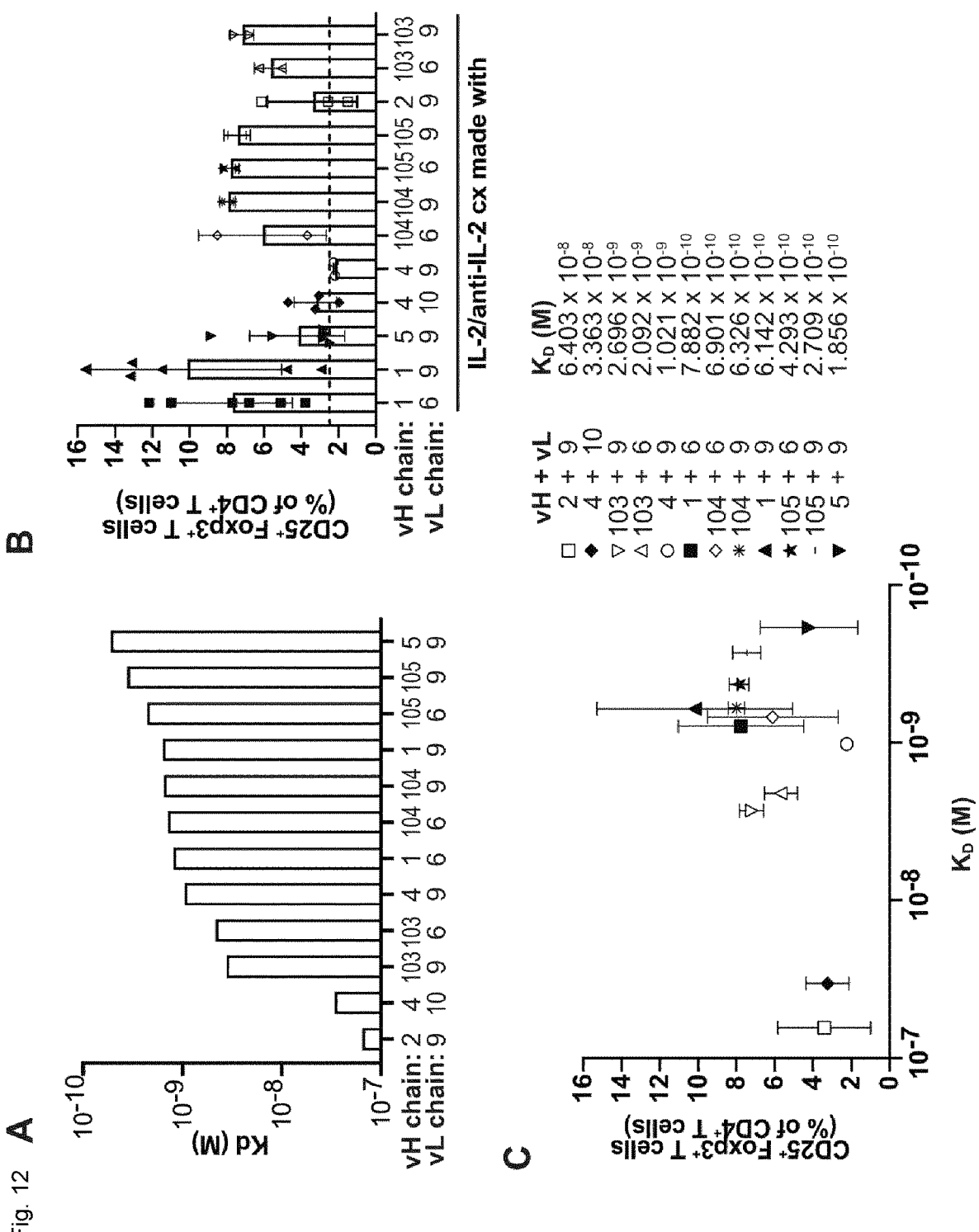

FIG. 12 shows optimal UFKA-20 affinity influences the ability to stimulate CD25$^+$Foxp3$^+$$T_{reg}$ cells in vivo. (A) Binding affinity Dissociation constants ($K_D$) of indicated UFKA-20 variants were determined using single-cycle surface plasmon resonance (SPR) measurement. (B) C57BL/6 wildtype mice received a single injection of IL-2/anti-IL-2cx (1 µg IL-2:10 µg UFKA-20 variant). Mean values±SD of the frequency of $CD4^+CD25^+Foxp3^+$ $T_{reg}$ cells in spleens was measured by flow cytometry at day 4. The dotted line indicates the mean value from PBS treated mice. (C) Correlation between antibody $K_D$ and the ability to induce $CD4^+CD25^+Foxp3^+$ $T_{reg}$ cells (mean values±SD of the $CD4^+CD25^+Foxp3^+$ frequency).

Figure 13:
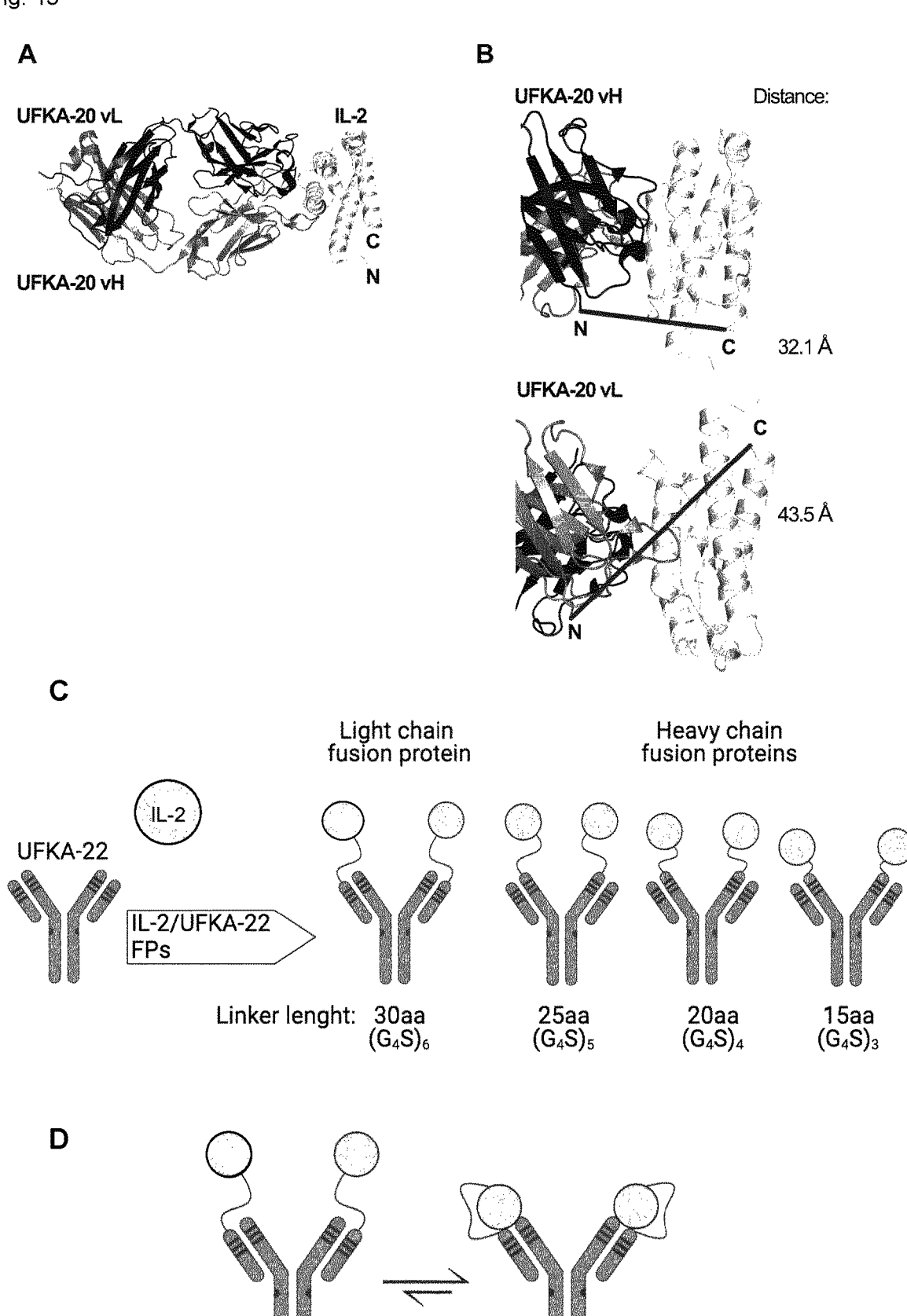

FIG. 13 shows distance measured using PyMOL software in Angstrom (Å) between IL-2's carboxy-(C—) terminus and the amino-(N—) terminus of UFKA-20's variable heavy (vH) or variable light (vL) chain. (A) Crystal structure of IL-2/UFKA-20 Fab complex (PDB: 6YE3). (B) Distance (dotted black line) between the C-terminus of IL-2 and the N-terminus of UFKA-20 vH (top panel) and UFKA-20 vL (bottom panel). UFKA-20 vH is shown in black, UFKA-20 vL in gray and IL-2 in white. (C) Schematic illustration of IL-2/UFKA-22 fusion proteins (FPs), where IL-2 is N-terminally linked to UFKA-22 light or heavy chain. (D) UFKA-22FP vL $(G_4S)_6$ at two different states. (Left) IL-2 is not associated with the binding pocket of the UFKA-22, or the IL-2 is associated with the binding pocket of the UFKA-22 (right).

Figure 14:
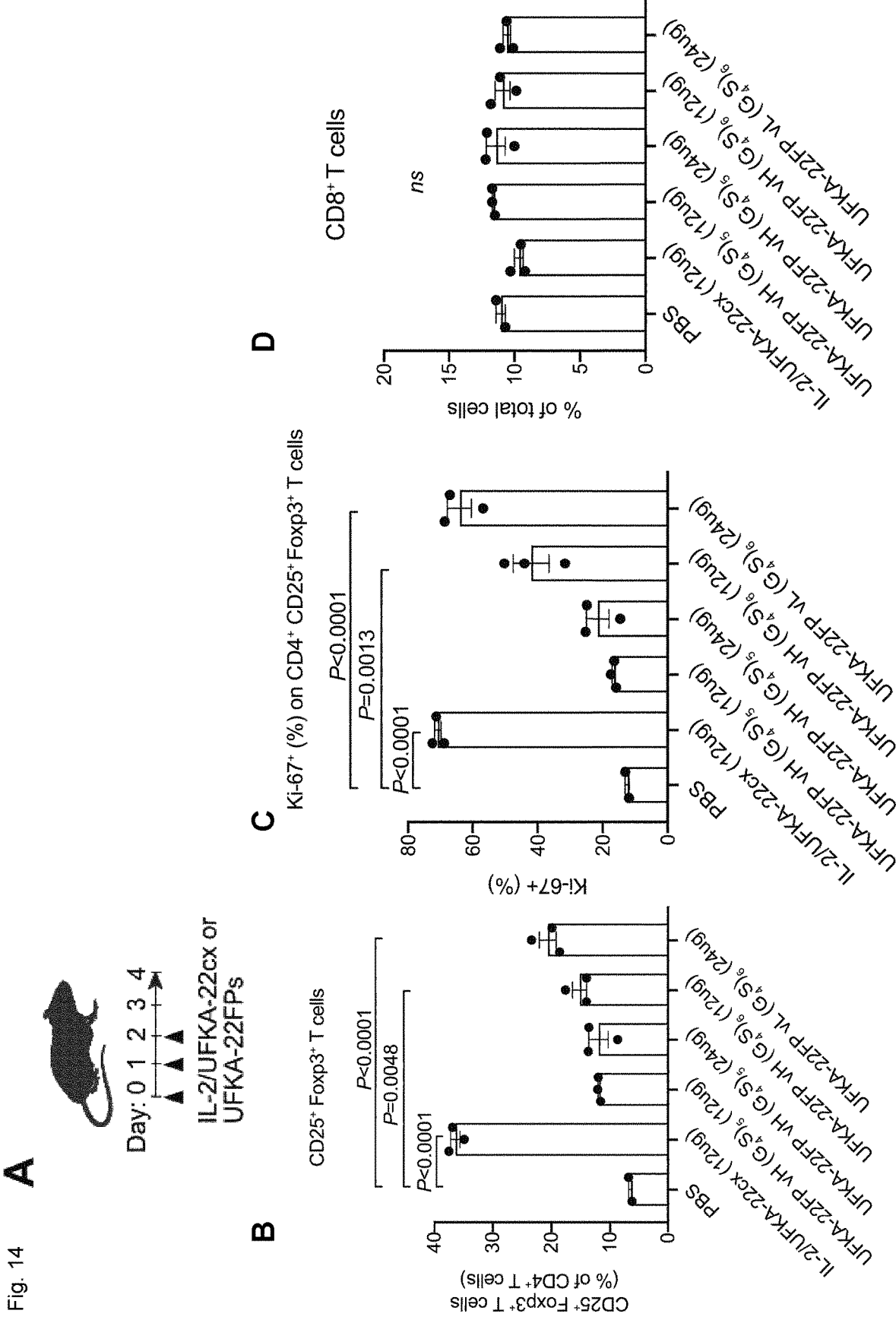

FIG. 14 shows comparison of IL-2/UFKA-22 and UFKA-22FPs in vivo in mice. (A) Experimental design: C57BL/6 mice were injected with IL-2/UFKA-22cx (12 µg [2 µg IL-2 and 10 µg UFKA-22]), UFKA-22FP vH (G4S) 5 (12 µg or 24 µg) and UFKA-22FP vL $(G_4S)_6$ (12 µg or 24 µg) on days 0, 1, and 2. Mice were euthanized on day 4, and frequencies of $CD4^+CD25^+Foxp3^+$ $T_{reg}$ cells and $CD8^+CD122^+CD44^{hi}$ T cells were analysed in spleens using flow cytometry. (B) Frequency of $CD25^+Foxp3^+$ among $CD4^+$ T cells, (C) Ki-67$^+$ on $CD25^+Foxp3^+$ $T_{reg}$ cells, and (D) $CD8^+$ T cells in the spleens of PBS, IL-2/UFKA-22 and UFKA-22FP treated mice as in (A), mean values ±SEM. P values were calculated using one-way ANOVA with Tukey's multiple comparison test; ns indicates not significant.

Figure 15:
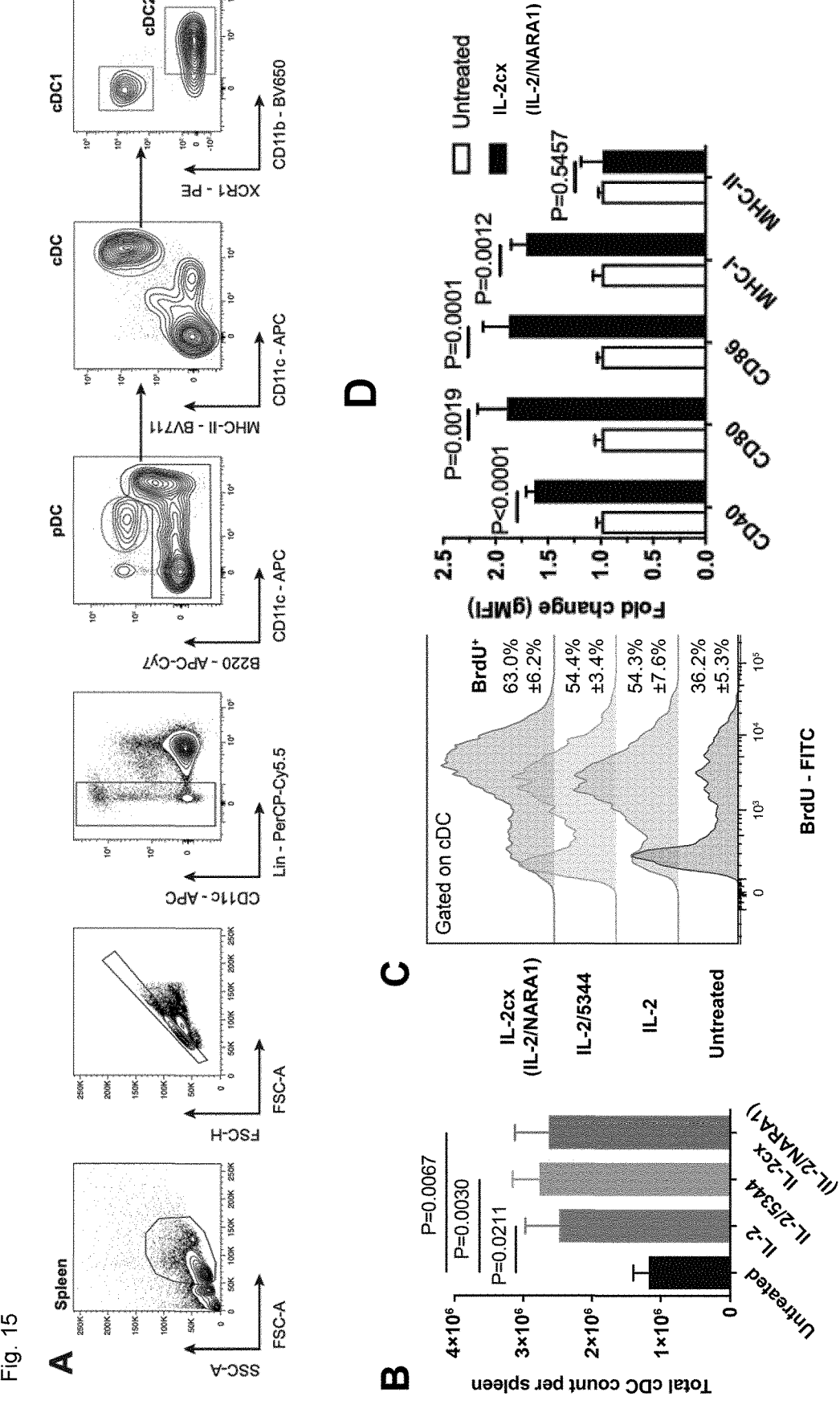

FIG. 15 shows (A) flow cytometry gating strategy for mouse splenic DC subsets including plasmacytoid DCs (pDC) and conventional type I and type II DCs (cDC1 and cDC2). (B) Splenic cDC expansion from mice treated with IL-2, CD25-biased IL-2/5344 complexes, or CD122-biased IL-2cx (IL-2/NARA1 complexes) (n=7 to 9 mice per group). (C) Proliferation of splenic cDCs from mice receiving the indicated treatments from (B) measured by BrdU incorporation over 3 days. (n=7 to 9 mice per group). (D) abundance of CD40, CD80, CD86, MHC-I, and MHC-II on splenic cDCs of untreated and IL-2cx-treated mice (IL-2/NARA1 complexes) displayed as representative histograms (left panel) and fold change of gMFI normalized to untreated (right panel). Data are presented as mean+/−SEM (n=9 mice per group).

Figure 16:
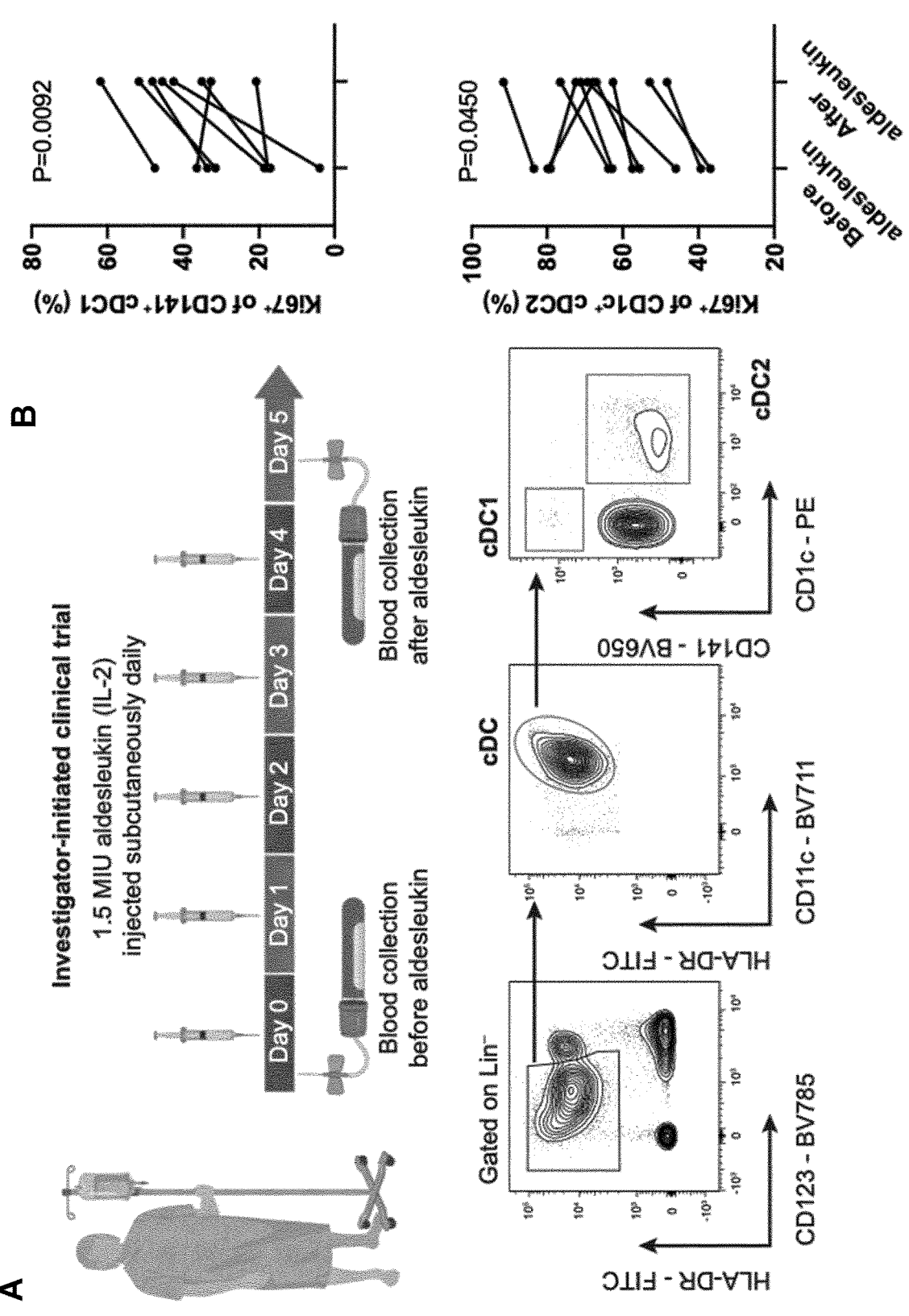

FIG. 16 shows (A) study design of the investigator-initiated clinical trial testing 1.5 million international units (MIU) aldesleukin injected subcutaneously daily on 5 consecutive days with blood draws before and after aldesleukin injection (upper panel). Corresponding gating strategy of human cDC subsets identifying CD141$^+$cDC1 and CD1c$^+$ cDC2 (lower panel). (B) Percentages of Ki67$^+$proliferating cDC1 (n=8) and cDC2 (n=10) in peripheral blood from patients before and after aldesleukin treatment.

Figure 17:
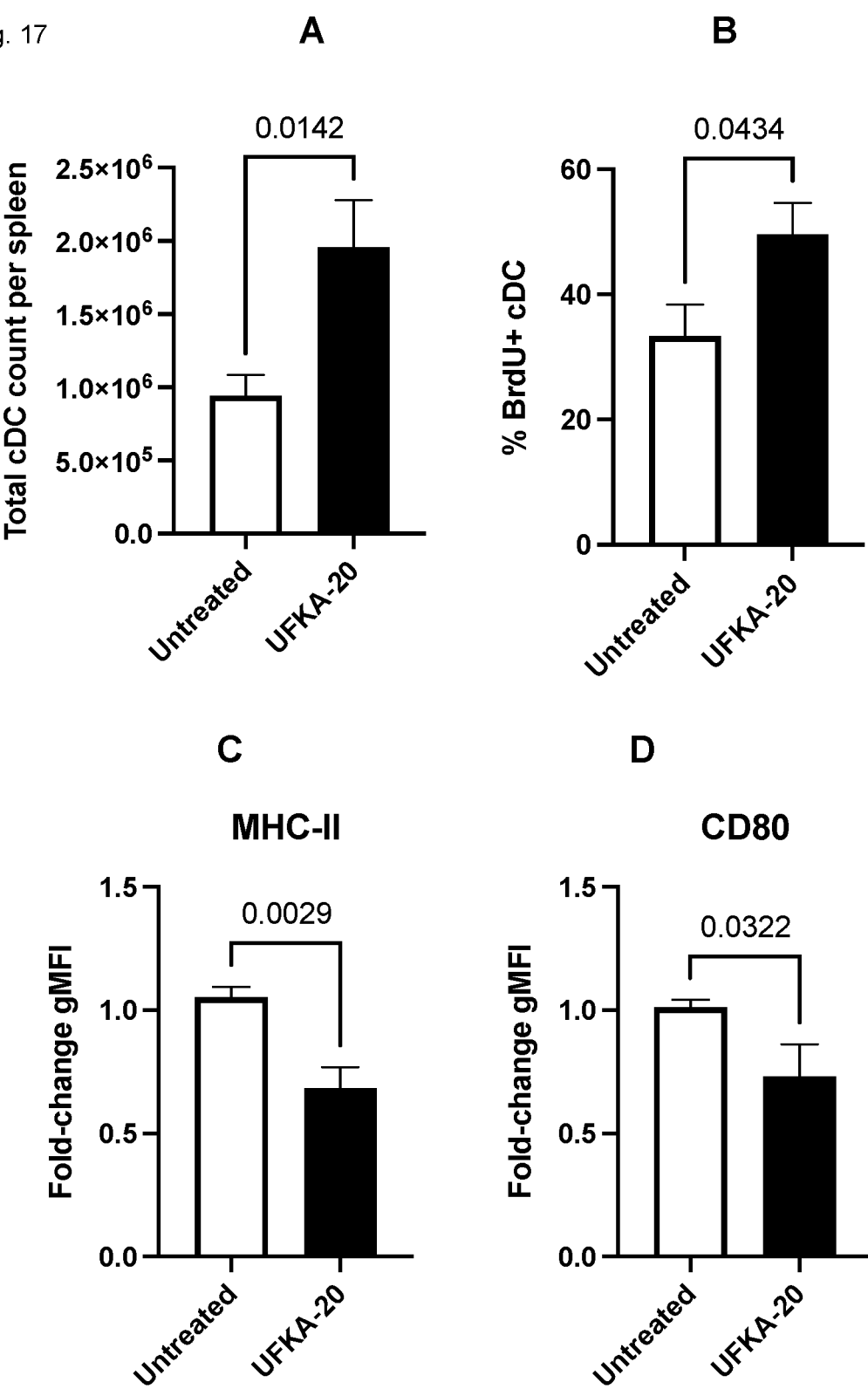

FIG. 17 shows (A) quantification of splenic cDCs after treatment with suppressive IL-2cx (IL-2/UFKA-20 complexes) on three consecutive days. (B) Proliferation of splenic cDCs from mice in (A) measured by BrdU incorporation over 3 days. Data are mean+/−SEM (n=7 mice per group). Surface expression of (C) MHC-II, (D) CD80, (E) PD-1, PD-L1, and PD-L2 on cDC by UFKA-20 complexes measured by flow cytometry on splenic cDCs of untreated and UFKA-20 complex-treated mice as in (A) displayed as fold change of geometric mean fluorescence intensity (gMFI) normalized to untreated. Data are presented as mean+/−SEM (n=5 to 8 mice per group). RNA sequencing of sorted conventional DCs (cDCs) isolated from mice 1 day following three days of UFKA-20 complexes treatment as in (F). Volcano plot of differentially expressed genes, with genes enriched in UFKA-20 complex treated mice on the right, and genes enriched in untreated mice depicted on the left. Each dot represents a single gene, with light grey marking genes that are non-significantly changed compared to untreated and black dots showing genes significantly (P<0.05) different from untreated. Genes coding representative pro- or anti-inflammatory proteins are indicated. Cut-offs were set at log 2 ratio of 0.5. Tgfbi, transforming growth factor beta-induced; Il1rn, Interleukin 1 receptor antagonist; Tab1, TGF-beta activated kinase 1/MAP3K7 binding protein 1; Il6st, interleukin 6 signal transducer; Ltb, lymphotoxin beta; Tnfsf14, tumor necrosis factor (ligand) superfamily, member 14; Csf1, colony stimulating factor 1; Fas, TNF receptor superfamily member 6.

Table 1. SPR analysis of anti-IL-2 mAbs UFKA-20, UFKA-22-00 (briefly, UFKA-22), UFKA-22-02, and UFKA-22-07, in comparison to the previously-reported anti-IL-2 mAbs JES6-1, F5111, and NARA1.

Table 2 shows IL-2 binding characteristics of UFKA-22 variants with framework mutations measured by surface plasmon resonance (SPR).

Table 3 shows $V_H$ (SEQ ID NO 019) and $V_L$ (SEQ ID NO 020) alterations in UFKA-20 variants.

Table 4 shows predicted role of amino acid substitutions in UFKA20 variants from Table 3.

Examples

Material and Methods

Cell Lines and Primary Cells

HEK293T cells obtained from the American Type Culture Collection (ATCC) were maintained in Dulbecco's modified Eagle medium supplemented with fetal calf serum (10% v/v, Thermo Scientific) and penicillin-streptomycin (100 U/ml, Thermo Scientific). Peripheral blood mononuclear cells (PBMCs) were isolated by Ficoll-Paque PLUS (GE Healthcare) gradient centrifugation from human peripheral blood collected from healthy individuals after prior informed consent and with approval of the Ethical Committee of the Canton of Zurich (BASEC no. 2016-01440).

Generation of Fluorescently-Tagged IL-2R Subunits

IL-2R subunits were C-terminally linked to fluorescent proteins with a flexible 15 amino acid (GGGGS) 3-spacer (motif SEQ ID NO 021). Sequences encoding CyPet, YPet or RFP657 (RFP) derived from plasmids pCEP4CyPet-MAMM and pCEP4yPET-MAMM (Addgene plasmids 14033 and 14032, respectively, kindly donated by P. Daugherty) and pSG4OC-RFP657 (kindly provided by D. Hecki, Hannover Medical School). CyPet was amplified using specific primers: forward 5'-CGTCTCGTGGT-GGTGGTTCTGGTGGTGGTGGTTC-TGTGACAAGG-3' (SEQ ID NO 022) and reverse 5'-GGTGGTCTCGAGTT-ATTTGTACA-GTTCGTCCATGCCG TG-3' (SEQ ID NO 023). The gene sequence of human CD25 was amplified from human PBMC RNA (RNeasy Plus Mini Kit, Qiagen), transcribed to complementary DNA (cDNA) using Quanti-Tect Reverse Transcription Kit (Qiagen), following PCR amplification using specific primer pairs for human CD25: forward 5'-CTAGGAAGCTTATCTATGGATTCAT- ACCTGCTG-3' (SEQ ID NO 024) and reverse 5'-ACCAGAACCACCACCACCAGAACCACCAC-CACCGATTGTTCTTCTA-CTCTTCCTCTG-3' (SEQ ID NO 025). PCR products were purified from 0.5-1% agarose gels by gel extraction (New England BioLabs), fragments were annealed using overlap extension PCR and cloned into a mammalian expression vector pCSCMV (Addgene plasmid 30530, kindly donated by G. Ryffel). Human CD122-CyPet and human CD132-RFP657 (termed CD132-RFP) were synthesized by GeneArt service (Thermo Scientific) and cloned into the mammalian expression vector pcDNA3.1.

Cell-Based IL-2R Binding Assay $0.75 \times 10^6$ HEK293T cells were co-transfected in six-well plates with each 1.3 µg pCD25-CyPet, pCD122-YPet and pCD132-RFP using a 1:3 DNA to ViaFect (Promega) ratio in Opti-MEM (Thermo Scientific). Total DNA amount was adjusted to 3.9 µg using empty vector pcDNA3.1, when one or two IL-2R subunits were transfected and culture at 37° C., 5% $CO_2$. Cells were detached 48 hours after transfection using enzyme-free cell dissociation buffer (Thermo Scientific) and collected in FACS buffer (PBS containing 2% FBS plus 2 mM EDTA). Rhodamine-labelled IL-2 (IL-$2_{Rhod}$) and anti-IL-2 mAbs were mixed in a 1:1 molar ratio and incubated for 15 minutes at room temperature (RT). To generate IL-$2_{Rhod}$, human IL-2 was reconstituted with sterile water and dialyzed into a 50 mM phosphate buffer (pH=6.5) to optimize for preferred N-terminal rhodamine coupling, followed by incubation with N-hydroxy-succinimidyl (NHS)-rhodamine (Thermo Scientific) for two hours on ice. Non-reacted NHS-rhodamine was removed by gel filtration (Zeba Spin Desalting Columns, 7K MWCO, Thermo Scientific). IL-$2_{Rhod}$/anti-IL-2 mAb complexes were incubated with $0.3 \times 10^6$ HEK293T cells (expressing IL-2R subunits or mock control) in V-bottom, 96-well plates for 10 minutes at 37° C., washed twice with cold FACS buffer and incubated for 20 minutes with BV605 rat anti-mouse IgG1 (BD Biosciences, clone X56) in the fridge. Following surface staining, cells were washed with PBS, fixed with 2% paraformaldehyde, acquired with a BD LSRFortessa and analysed using FlowJo software (both BD Biosciences).

Mice

C57Bl/6J mice were purchased from Charles River Laboratories. Female mice were used for experiments at two to five months of age. Experiments were approved by the Veterinary Office of the Canton of Zurich (license 246/2016) and conducted in accordance with Swiss Federal and Cantonal laws. Mice were randomized by unblinded investigators and held in a specific pathogen-free facility at the University Hospital Zurich following institutional guidelines.

Rhesus Macaques

The study with rhesus macaques (*Macaca* mulatta) was carried out at the Biomedical Primate Research Centre (BPRC) in 15 healthy female adults, aged four to 15 years and weighing five to 15 kg. Animals did not show circulating antibodies specific to STLV or SRV and had not received any immunosuppressive or antibody therapy before the study. All procedures and protocols complied with all relevant ethical regulations for animal testing of BPRC's Animal Experiments Committee. Animals were randomized into five groups of three animals each: group 1: LD IL-2 (10 µg/kg); group 2: HD IL-2 (33 µg/kg); group 3: LD IL-2/UFKA-22cx (10/100 µg/kg); group 4: HD IL-2/UFKA-22cx (33/330 µg/kg); and group 5: UFKA-22 (330 µg/kg). IL-2 was given daily by subcutaneous injection, while IL-2/

UFKA-22cx and UFKA-22 were injected intravenously on days 0 and 3. Animals were sedated for injections and bleedings.

Clinical Trial and Human Samples

Human samples were collected within the clinical trial "Open-label, Monocentric, Phase II, Investigator-initiated Clinical Trial on Unbiased Characterization of Immunological Parameters in Interleukin-2-treated Systemic Lupus Erythematosus" (Charact-IL-2, ClinicalTrials identifier: NCT03312335) and the "Fundamental research project for phenotypical and functional characterization of different leukocyte subsets in healthy and diseased individuals" (PFCL-1, BASEC no. 2016-01440). Both projects have been reviewed and approved by the competent Swiss authorities and have been carried out in accordance with principles enunciated in the current version of the Declaration of Helsinki, the guidelines of Good Clinical Practice, and Swiss legal requirements. Prior to enrolment into the clinical trial or sample collection, written informed consent was obtained. Human blood was collected into EDTA Vacutainer tubes (BD Biosciences) followed by Ficoll-Paque PLUS (GE Healthcare) gradient centrifugation for peripheral blood mononuclear cell (PBMC) isolation. Isolated PBMCs were frozen in foetal calf serum (FCS, Gibco) containing 10% dimethyl sulfoxide (Sigma) and stored for less than 1 year in liquid nitrogen prior to analysis. Serum was isolated from blood collected with Clot Activator Vacutainer tubes (BD Biosciences) and stored for less than 18 months at −80° C. prior to analysis. For evaluation of IL-2-mediated expansion of cDCs and lymphocytes, blood from patients with systemic lupus erythematosus (SLE) was collected prior and after a 5-day course of daily 1.5 million international units (MIU) of aldesleukin (Proleukin®, Novartis Pharma), according to the study protocol.

IL-2 mAb Complex Formation

For the HEK cell-based assay IL-$2_{Rhod}$ was mixed with anti-hIL-2 antibodies at a 1:1 ratio in FACS buffer (1×PBS, 2% FBS, 2 mM EDTA) and incubated at room temperature for at least 15 minutes. For in vivo applications, hIL-2 was mixed with anti-hIL-2 antibodies at a 1:1 ratio in sterile PBS and incubated at room temperature for at least 15 minutes. Injection volume was 200 microliter per intraperitoneal injection. Recombinant human IL-2 (teceleukin, Roche) was obtained from the National Cancer Institute of the National Institutes of Health. Antibody complexes were prepared by mixing 15,000 IU IL-2 and 15 µg anti-IL-2 monoclonal antibodies (mAbs) per injection, as previously described (Arenas-Rameriz N. *Sci Transl Med* 2016, 8:367ra166). IL-2cx, or 200,000 IU IL-2 were injected daily for three consecutive days. BrdU-incorporated cells were measured using the FITC BrdU Flow Kit (BD Biosciences) according to manufacturer's instructions.

Flow Cytometry

Single cell suspensions of LNs and spleens were prepared and stained for surface markers and intracellular Foxp3 and Ki-67, using a Foxp3/transcription factor intracellular staining kit according the manufacturers' instructions (Thermo Fisher). To detect pSTAT5 in mice or macaques, cells were immediately fixed using Phosflow Lyse/Fix Buffer (BD Biosciences) or lysing solution (Becton Dickinson), and further processed for intracellular staining according to manufacturer's instructions. To measure pSTAT5 in vitro, $10^6$ magnetically-purified human CD3+ T cells (BioLegend) were seeded in 96-well, V-bottom plates and stimulated for 15 minutes at 37° C. using IL-2, IL-2/UFKA-20cx, or IL-2/UFKA-22cx. Intracellular pSTAT5 was stained as aforementioned using anti-STAT5 (pY694) mAb (Thermo Fisher). For surfaces staining of macaque cells, we incubated mAbs with 200 µl EDTA blood, followed by red blood cells lysis, fixation and permeabilization for intracellular staining of Foxp3 and Ki-67, according to standard protocols. Samples were acquired on a BD LSRFortessa and analysed using FlowJo. Antibodies and fluorescent dyes used for flow cytometry were purchased from ebioscience, BD Biosciences, Biolegend or Miltenyi.

ELISA

Flat-bottom Nunc MaxiSorp 96-well plates (Thermo Scientific) were coated overnight at 4° C. with NARA1 anti-human IL-2 mAb (capture). After washing the plates with PBS, 0.1% Tween 20 (Sigma-Aldrich), wells were blocked for >1 hour at RT with PBS, 1% BSA (Sigma-Aldrich), 0.1% Tween 20 solution, shaking at 450 rpm. Cell supernatants or purified UFKA mAbs were incubated for one to two hours on plates, where IL-2 was directly coated or captured by plate-coated NARA1. After washing the plates, IL-2 or competitive binding was assessed by incubating the plates with anti-mouse IgG (BioLegend) or biotinylated anti-IL-2 detection mAb (clone 5344.111, BD Biosciences) for one hour at RT and 450 rpm. After an additional wash, plates were incubated with streptavidin-conjugated horseradish peroxidase (BD Biosciences) for 45 minutes at RT in the dark. Finally, after a last wash, plates were developed with TMB Peroxidase EIA substrate (BioRad) for two to five minutes, and stopped by adding $H_2SO_4$ (1.8 M, Sigma-Aldrich). Absorbance at 450 nm was read using an iMark microplate reader (BioRad). Serum half-life of IL-2 or IL-2/UFKA-20cx was measured using a sandwich ELISA, where NARA1 served as capture and a biotinylated anti-IL-2 mAb (clone 5334, R&D Systems) as detection mAb, followed by development, as above.

Surface Plasmon Resonance

For SPR studies, UFKA-20 or NARA1 were directly immobilized onto a CMD200 chip (XanTec bioanalytics) and titrated IL-2 concentrations starting from 300 nM followed by 2-fold dilutions were injected. To measure CD25 and CD122 binding, IL-2 (1000 nM) was captured for 60 seconds on the anti-IL-2 mAb-coated chip, followed by serial injections of recombinant CD25 or CD122 (R&D Systems), starting with 333 nM and followed by three-fold dilutions. Chip surface was regenerated after every cycle using glycine buffer pH 1.5. Measurements were acquired at 20° C. and analysed using a Biacore T100 (GE Healthcare).

Structural Analysis of the IL-2/UFKA-20cx

Fab fragments of UFKA-20 were generated by papain cleavage of the full-length mAb followed by Protein A purification. 1.5 ml UFKA-20 (15.3 mg/ml in 50 mM with 90 mM NaCl at pH 7.0) was mixed with dichlorodiphenyltrichloroethane (DDT) and papain (Roche) to reach a final concentration of 5 mM and 1.5 mg/ml, respectively. After 16 hours of digestion at RT, papain was deactivated using 56 mM E64 solution (Roche) and diluted ten times with Tris/NaCl buffer (25 mM Tris, 25 mM NaCl, pH 8.0). The mixture was loaded on a Protein A column equilibrated with Tris/NaCl buffer, and the flow-through fraction harbouring the Fab fragments was collected and further purified by sized exclusion chromatography (SEC). IL-2/UFKA-20 Fab complexes, formed by mixing purified UFKA-20 Fab with a 10-fold molar excess of human IL-2 dissolved in water, were purified by SEC using a Superdex 200 10/300 GL column on an Äkta pure chromatography system (GE Healthcare). Fractions containing the complexes were pooled and dialyzed overnight at 4° C. against Tris/NaCl buffer (pH 7.4) and concentrated using Amicon Ultra-Centrifugal Filter Units (10-kDa, MerckMillipore) to a final protein concentration of 10 mg/ml as measured by absorption at 280 nm. Various crystallization buffers were screened and refined to find optimal crystallization conditions. Finally, the IL-2/UFKA-20 Fab complex solution was mixed 1:1 with a crystallization buffer comprising 10.86% (v/v) PEG 8000, 5.76% (v/v) ethylene glycol, 100 mM HEPES (pH 7.48). Crystals were grown by sitting-drop vapor diffusion in 96-well plated at 20° C., harvested and cryoprotected using reservoir solution supplemented with 30% (v/v) ethylene glycol and immediately frozen in liquid nitrogen. Diffraction data were collected at a wavelength of 1 Å at beamline X06DA (Swiss Light Source, Paul Scherrer Institut, Villigen, Switzerland), which is equipped with a Pilatus 2M detector (Dectris, Baden-Wättwil, Switzerland). Data processing was done using XDS and Aimless. The IL-2/UFKA-20 Fab complex structure was solved by molecular replacement using MOLREP, first with the structure of a Fab fragment of an anti-leukotriene antibody (PDB: 5B6F) and subsequently with the structure of human IL-2 (PDB: 1M47) (Arkin M. R. et al. PNAS 2003 100:1603) as search models. Model building was done in Coot and refined using REFMAC5, BUSTER, and PHENIX. We used TLS refinement where each domain was defined as an individual TLS group. The final structure contained three IL-2/UFKA-20 complexes in the asymmetric unit. Epitope overlaps of IL-2R subunits with anti-IL-2 mAbs were quantified using the protein interfaces, surfaces and assemblies' service (PISA) at the European Bioinformatics Institute (http://www.ebi-.ac.uk/pdbe/prot_int/pistart.html), and further computed using Excel (Microsoft).

RNA Sequencing (RNA-seq)

Forty thousand splenic mouse cDCs from untreated and UFKA20 complex-treated wild-type mice were separated by FACS in RLT Plus lysis buffer (Qiagen) containing 1% 2-mercaptoethanol (Sigma-Aldrich). Subsequently, RNA was isolated using the RNeasy Plus Micro Kit (Qiagen). The RNA extracted from sorted cells was quantified for quality and concentration using the TapeStation RNA high sensitivity kit (Agilent). SMARTer Stranded Total RNA Seq Kit v2 (Takara Bio) was used to prepare cDNA by universal priming (with 3 min fragmentation) and to deplete ribosomal cDNA with ZapR v2 and R Probes v2. The libraries were quantified by Tapestation D1000 (Agilent) measurements, and sequenced on a HiSeq 4000 platform using 125 cycles single-read targeting ~40M reads per sample. Adapters and low-quality tails were trimmed from reads prior to read alignment. STAR aligner (v2.5.4b) was used to align the RNA-seq dataset to Ensembl genome build GRCh38.p10 (Release 91). Gene expression counts were calculated with feature counts from Bioconductor package Rsubread (v1.32.1). A gene was considered as expressed if, in at least one group of the comparison, it had more than 10 counts in more than half of the samples. Differentially expressed genes were detected using Bioconductor package EdgeR (v3.20.6). Gene set enrichment analysis was done with Gene Ontology analyser for RNA-seq and other length biased data (goseq, v1.30.0).

Quantification and Statistical Analysis

Statistical testing was performed using the Prism software (GraphPad). As indicated in the figure legends, most experiments were analysed by one-way ANOVA with Tukey's or Dunnett's multiple comparison, or with two-tailed unpaired Student's t-test. For datasets where the count was too small for the normality test, normal distribution was assumed based on data distribution. $p < 0.05$ was considered significant.

Example 1: Generation and Selection of Anti-Human IL-2 Monoclonal Antibodies Balb/c mice were immunized with human IL-2 in complete Freund's adjuvant (Sigma-Aldrich) and boosted twice with IL-2 emulsified in incomplete Freund's adjuvant (Sigma-Aldrich). Four to five weeks after the first immunization, mice were sacrificed to collect spleens. Splenocytes were mixed with myeloma cells at a 5:1 ratio with polyethylene glycol 1500 (Roche). Clones were cultured in Iscove's modified Dulbecco's medium supplemented with 10% fetal bovine serum (FBS), 50 mM mercaptoethanol, 1:100 insulin-transferrin-selenium, 2% IL-6-conditioned medium, penicillin-streptomycin, gentamicin (all from Life Technologies), and hypoxanthine-aminopterin-thymidine (HAT) (Sigma-Aldrich). B cell hybridoma supernatants were screened for IL-2 reactivity using a direct IL-2-binding ELISA and for specificity using a competition ELISA, followed by subcloning of positive hits. mAbs were expanded in hypoxanthine-thymidine (HT) medium (LifeTechnologies). After retesting, anti-IL-2 mAbs were purified from cell supernatants using Protein G agarose purification (Thermo Fisher). Antibodies were produced by transiently transfected HEK293F cells, affinity-purified using Protein A MabSelect SuRe resin (GE Healthcare) and fractionated. Purity was analysed by sodium dodecyl sulfate (SDS)-polyacrylamide gel electrophoresis.

Example 2: Biasing Anti-IL-2 mAbs have Distinct Properties of IL-2R-Binding and IL-2 Delivery Using a competition enzyme-linked immunosorbent assay (ELISA), over ten thousand anti-human IL-2 mAbs, including those generated in Example 1, proprietary antibodies and publicly available clones from mouse hybridoma libraries were assessed for their IL-2 and IL-2R binding properties. Unless otherwise specified, all IL-2 and IL-2R subunits in the examples refer to human molecules. To identify and compare CD25-biasing anti-IL-2 mAbs, a novel cell-based in vitro screening platform where monomeric CD25, dimeric $CD122^+CD132$ and trimeric $CD25^+CD122^+CD132$ were expressed on human cells was developed. Fluorescently-tagged IL-2R subunits were generated, and transiently expressed in human embryonic kidney (HEK) 293T cells, enabling precise identification by flow cytometry of cells expressing defined IL-2R subsets and quantification of the binding of rhodamine-labelled IL-2 ($IL-2_{Rhod}$), either alone or in complex with an anti-IL-2 mAb. CD25-biased IL-2cx associated with CD25 but not with $CD122^+CD132$, whereas CD122-biased IL-2cx showed the opposite pattern (FIG. 1A). Five anti-IL-2 mAbs were selected on their different binding patterns, termed UFKA-10, UFKA-20 (heavy chain SEQ ID N019, light chain SEQ ID NO 020), UFKA-30, UFKA-40, and UFKA-50, which fell into three broad categories: unbiased (UFKA-10), CD25-biased (UFKA-20, UFKA-30, and UFKA-40), and CD122-biased (UFKA-50) (FIG. 1B). As expected, $IL-2_{Rhod}$ alone showed low binding to CD25, intermediate association with $CD122^+$ CD132, and strong binding to $CD25^+CD122^+CD132$ (FIG. 1C). Next, $IL-2_{Rhod}$ was complexed at a 1:1 ratio with our different anti-IL-2 mAbs and tested them on IL-2R subunit-expressing HEK293T cells. Compared to $IL-2_{Rhod}$, complexes of $IL-2_{Rhod}$ with UFKA-10 showed a slightly reduced binding to CD25 and $CD122^+CD132$, suggesting mild interference of UFKA-10 with these receptor subunits, whereas association of $IL-2_{Rhod}$ with $CD25^+CD122^+CD132$ was unaltered by this mAb (FIG. 1C). A clear pattern of CD25 bias emerged when testing the mAbs UFKA-20, UFKA-30 and UFKA-40, although with distinct differences between the mAbs (FIGS. 1C and 1D). Thus, $IL-2_{Rhod}$/UFKA-30cx and $IL-2_{Rhod}$/UFKA-40cx bound preferentially to CD25 and $CD25^+CD122^+CD132$ and remained bound to 74.5% and 93.2% as complexes, respectively, whereas their association with $CD122^+CD132$ was either slightly reduced (as with UFKA-30) or remained unchanged (as with UFKA-40) (FIG. 1C-1E). Notably, $IL-2_{Rhod}$/UFKA-20cx preferentially associated with CD25, with about two thirds of the measured interactions being made by $IL-2_{Rhod}$/UFKA-20cx, while in less than a third $IL-2_{Rhod}$ alone was detected on CD25. However, $IL-2_{Rhod}$/UFKA-20cx appeared to rapidly dissociate upon interaction with trimeric $CD25^+CD122^+CD132$, as evidenced by less than 8.4% of this interaction being formed by $IL-2_{Rhod}$/UFKA-20cx and 91.6% by uncomplexed, free $IL-2_{Rhod}$ binding to $CD25^+CD122^+CD132$ (FIG. 1C-1E); yet, binding of $IL-2_{Rhod}$/UFKA-20cx to $CD122^+CD132$ was disfavoured by the presence of UFKA-20 compared to $IL-2_{Rhod}$ (FIG. 1C), suggesting that UFKA-20 conferred a "CD25 bias" to $IL-2_{Rhod}$ and, simultaneously, allowed $IL-2_{Rhod}$ to dissociate from UFKA-20 and bind to trimeric $CD25^+CD122^+CD132$, thereby allowing "IL-2 delivery" to a signalling IL-2R complex (FIG. 1F-1H). Conversely, UFKA-30 and UFKA-40 enforced an even stronger CD25 bias upon $IL-2_{Rhod}$, but they failed to dissociate and deliver IL-2 to trimeric IL-2R (FIG. 1F-1H). Unlike the aforementioned CD25-biasing anti-IL-2 mAbs, $IL-2_{Rhod}$/UFKA-50cx showed reduced CD25 binding and clearly favoured association with dimeric $CD122^+CD132$ and trimeric $CD25^+CD122^+CD132$ IL-2Rs (FIG. 1C-1H), similar to IL-2cx with the well-characterized CD122-biasing NARA1 mAb (Arena-Ramirez et al. *Sci. Transl. Med.* 2006 8:367). Taken together, distinct differences were observed in mechanisms of CD25-biasing mAbs in terms of the two features CD25 bias, and IL-2 delivery to signalling IL-2Rs.

Example 3: CD25 Bias and IL-2 Delivery are Key for Selective Stimulation of Mouse $T_{reg}$ Cells The in vivo activity our CD25-biasing mAbs in mice was then assessed. C57BL/6 WT mice received daily injections for three days of IL-2 alone or in complex with UFKA-10, UFKA-20, UFKA-30, UFKA-40, and NARA1, followed by flow cytometry analysis of $CD4^+CD25^+Foxp3^+$ $T_{reg}$, $CD8^+$ $CD44^{hi}$ $CD122^+$ memory T, and CD3-NK1.1+$CD122^+$NK cells in lymph nodes (LNs) and spleens of treated animals (FIGS. 2A, 3A, and 3B). Controls receiving saline showed on average 8.7% $CD4^+CD25^+Foxp3^+$ $T_{reg}$ cells and 7% $CD8^+CD44^{hi}$ $CD122^+$ memory T cells in their LNs, as well as 8.6% $CD4^+CD25^+Foxp3^+$ $T_{reg}$ cells, 13.4% $CD8^+CD44^{hi}$ $CD122^+$ memory T cells and 2.8% NK cells in their spleens (FIGS. 2A, 3A, and 3B). Upon LD IL-2 treatment (1.5 µg per mouse daily), percentages and counts of $CD4^+CD25^+$ $Foxp3^+$ $T_{reg}$ and $CD8^+CD122^+$ memory T cells increased about two to three-fold in both LNs and spleens (FIGS. 2A, 2B and 3A). IL-2cx made with UFKA-10, UFKA-30, and UFKA-40 only discretely improved the stimulation of $CD4^+$ $CD25^+Foxp3^+$ $T_{reg}$ cells over that seen with LD IL-2 (FIGS. 2A and 2B), although these IL-2cx were able to curtail the expansion of $CD8^+CD44^{hi}$ $CD122^+$ memory T cells (FIG. 2A-2C). However, IL-2/UFKA-20cx induced a vigorous expansion of $CD4^+CD25^+$ $Foxp3^+$ $T_{reg}$ cells, reaching a total of almost $20 \times 10^6$ $T_{reg}$ cells in LNs and spleens, compared to $1.5 \times 10^6$ in saline- and $3 \times 10^6$ in LD IL-2-treated animals, whereas percentages and counts of $CD8^+CD44^{hi}$ $CD122^+$ memory T cells remained unaltered compared to IL-2 alone (FIG. 2A-2C). As expected, the CD122-biased IL-2/NARA1cx induced preferential stimulation of CD8$^+$ CD44$^{hi}$ CD122$^+$ memory T cells, although some CD4$^+$CD25$^+$ Foxp3$^+$ T$_{reg}$ cell expansion was observed (FIG. 2A-2C), probably due to dissociation of IL-2 from NARA1 (Arenas-Ramirez N. et al. *Trends Immunol.* 2015 36:763). Collectively, these data demonstrate that CD25 bias alone, as seen with IL-2/UFKA-30cx and IL-2/UFKA-40cx in vitro, is insufficient to stimulate T$_{reg}$ cells in vivo. Rather, an IL-2cx's capacity to confer mild CD25 bias and deliver IL-2 efficiently to trimeric IL-2Rs, as with IL-2/UFKA-20cx, appear to be necessary features for their in vivo selectivity and efficacy. Hence, these screening assays identified UFKA-20 as a candidate mAb for further characterization as an improved method to increase IL-2 signalling to T$_{reg}$ cells to inhibit inflammation.

Figure 4:
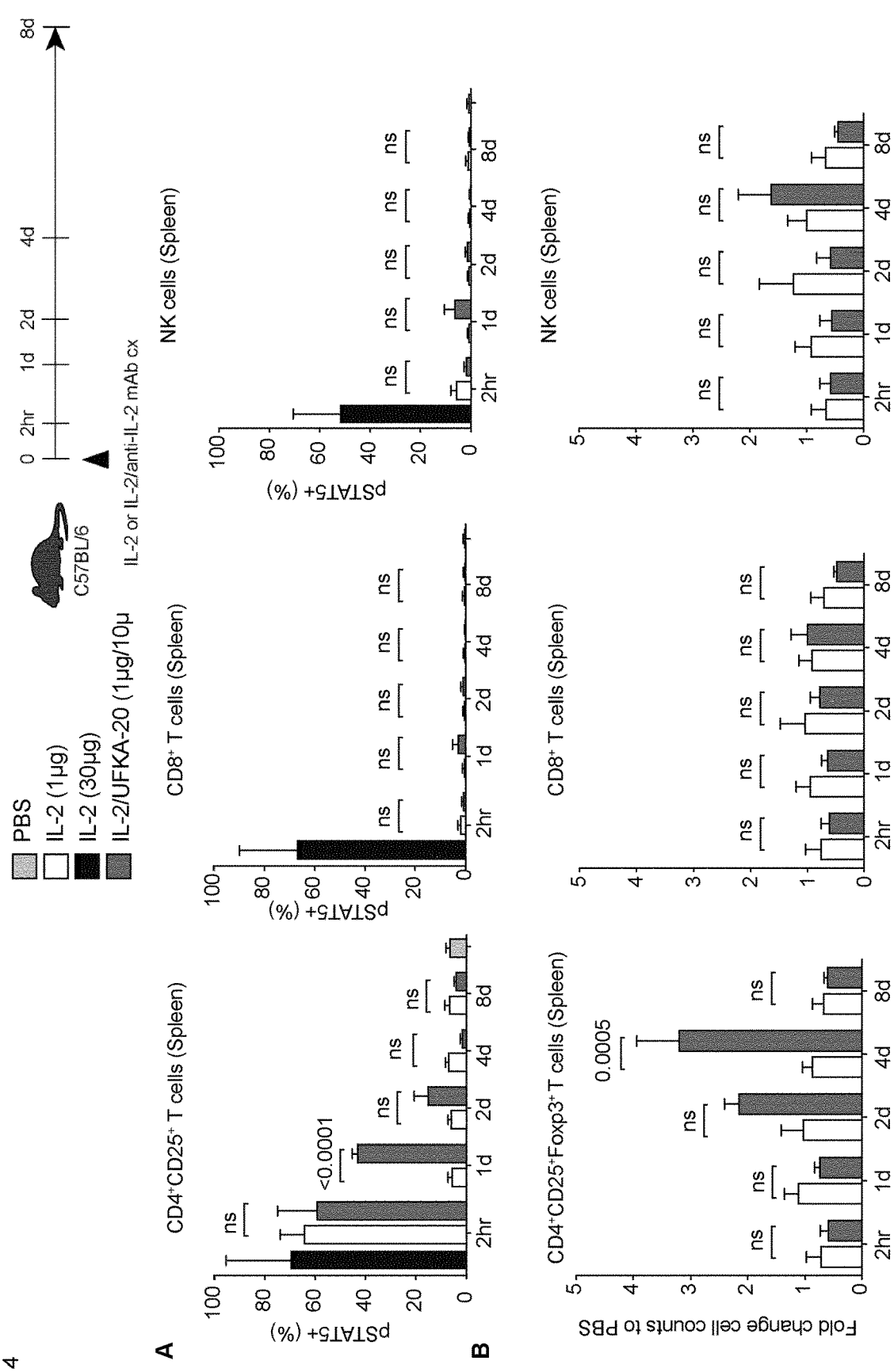

Example 4: IL-2/UFKA-20cx Provide Improved Signalling to Mouse T$_{reg}$ Cells In Vivo In a time-course experiment, we compared the capacity of a single intraperitoneal injection of LD IL-2 (1 μg) versus IL-2/UFKA-20cx (1 μg/10 μg) to induce signalling as measured by intracellular staining of phosphorylated STAT5 (pSTAT5) in CD4$^+$CD25$^+$ T, CD8$^+$ T, and NK cells in spleens of mice (FIG. 4). In mice receiving LD IL-2, we observed a preferential stimulation of CD4$^+$CD25$^+$ T cells at two hours after injection, but this effect had already disappeared on day 1 (FIG. 4A). CD8$^+$ T and NK cells did not phosphorylate STAT5 in response to LD IL-2, however, using a single injection of HD IL-2 (30 μg) resulted in robust signalling in all three lymphocyte subsets, including CD8$^+$ T and NK cells (FIG. 4A). IL-2/UFKA-20cx showed a high selectivity for CD4$^+$CD25$^+$ T cells that was apparent at two hours after injection and lasted for at least two days, whereas pSTAT5 levels in CD8$^+$ T and NK cells remained unaffected by this treatment (FIG. 4A). As a consequence, cell counts of CD4$^+$CD25$^+$ T cells increased on day two, peaked on day 4 and had returned to baseline on day 8 after a single injection of IL-2/UFKA-20cx, whereas CD8$^+$ T and NK cell counts did not change significantly over the course of the experiment, compared to IL-2 (FIG. 4B). The pSTAT5 signalling profile not only confirmed the selectivity of IL-2/UFKA-20cx for CD4$^+$CD25$^+$ T cells but also suggested IL-2/UFKA-20cx had a much longer in vivo half-life than IL-2. To test this, a single injection of IL-2 or IL-2/UFKA-20cx was given to mice, followed by measurement of free or UFKA-20-complexed IL-2 by a sandwich ELISA using NARA1 as capture mAb and MAB202 as detection mAb. IL-2 was only detectable at 30 minutes after injection and had disappeared within four hours, whereas IL-2/UFKA-20cx peaked at four hours and were present for over 24 hours after injection (FIG. 5). The estimated in vivo half-life of IL-2/UFKA-20cx was 30 hours compared to roughly 30 minutes for IL-2. Serum half-life of IL-2/UFKA-22cx was about 21 hours.

Figure 7:
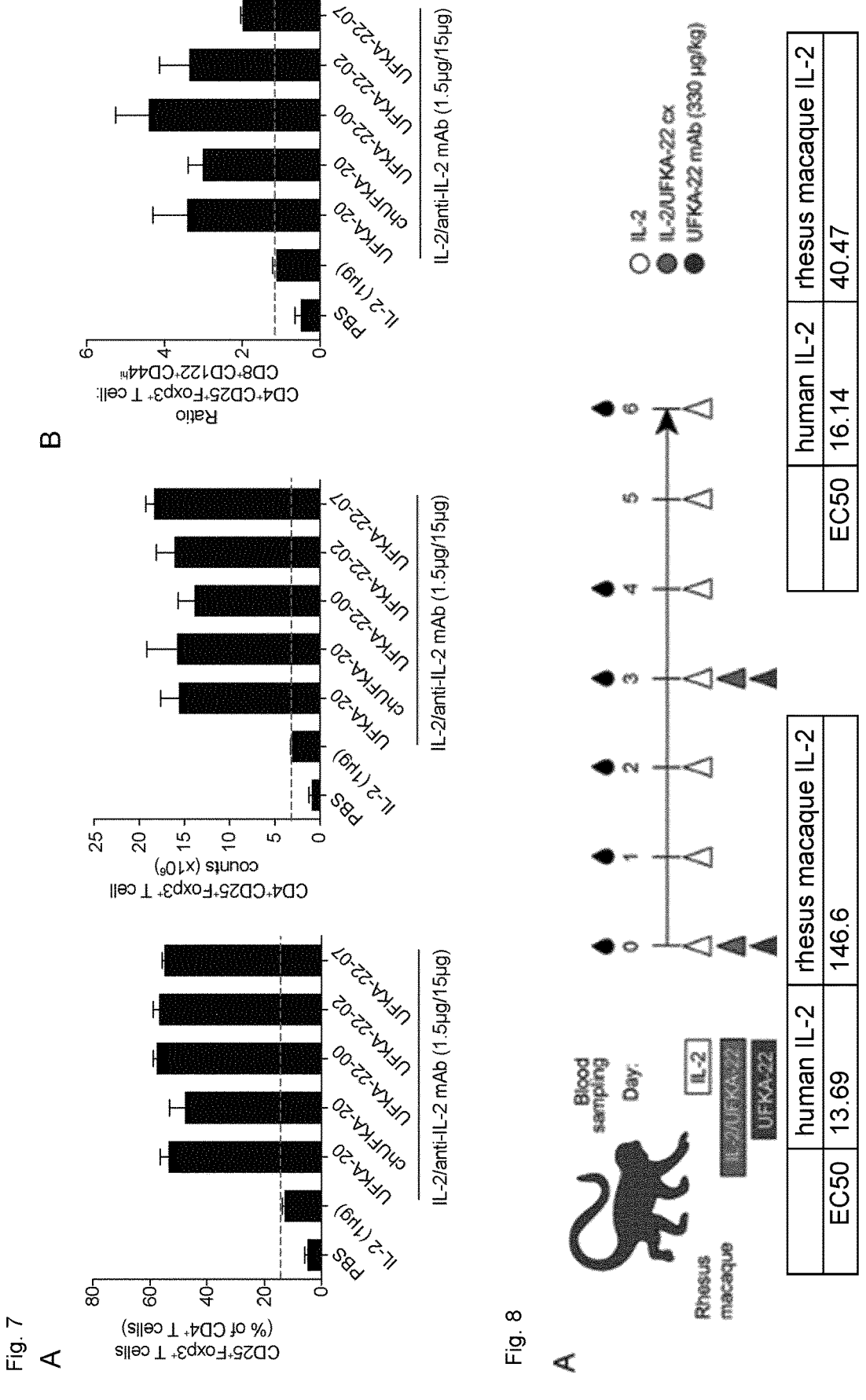

Example 5: IL-2/UFKA-20cx Selectively Stimulate Human T$_{reg}$ Cells In Vitro The activity of IL-2/UFKA-20cx was assessed on freshly-isolated resting human T cell subsets, including CD4$^+$ CD25$^+$ T cells that carry trimeric IL-2Rs and CD8$^+$ T cells that are equipped with dimeric (CD122$^+$CD132) IL-2Rs, as previously shown (Arena-Ramirez, 2006). CD3$^+$ T cells were purified from peripheral blood of healthy human donors and stimulated with titrated IL-2 and IL-2/UFKA- 20cx (at a 1:1 molar ratio of IL-2 and UFKA-20) for 15 minutes, followed by flow cytometry assessment of intracellular pSTAT5 on gated CD4$^+$CD25$^+$CD127l Foxp3$^+$ T$_{reg}$ and CD8$^+$ T cells. IL-2 at a concentration as low as 0.1 ng/ml was able to induce half-maximal STAT5 activation in CD4$^+$ T$_{reg}$ cells, whereas about 1000-fold higher concentrations were needed to achieve a comparable STAT5 activation in CD8$^+$ T cells (FIG. 6), consistent with a previous publication (Yu, Diabetes 2015 64:2172). IL-2/UFKA-20cx were comparably efficient as IL-2 in stimulating pSTAT5 in human CD4$^+$ T$_{reg}$ cells (FIG. 6). Contrarily, roughly 17-fold higher concentrations of IL-2/UFKA-20cx were necessary to achieve 50% pSTAT5$^+$CD8$^+$ T cells, based on half maximal effective concentrations (EC50) (FIG. 6). The demonstrable improved CD25-biasing selectivity and efficacy of UFKA-20 in vitro measured using human IL-2R-bearing cell lines, in different in vivo experiments in mice, and in vitro using freshly-isolated primary T cell subsets from different healthy donors was followed by generation of several humanized versions of UFKA-20. Human germline genes sharing the highest level of identity with the V$_L$ (SEQ ID NO 020) and V$_H$ (SEQ ID NO 019) framework sequences of UFKA-20 were identified, codon optimized, and synthesized by GeneScript Custom Gene Synthesis and cloned into an expression vector containing Fc-silent (N297A) human IgG1. The complementarity-determining regions (CDR) of UFKA-20 were transferred onto a human immunoglobulin G1 (IgG1) backbone carrying an N297A mutation, which prevents glycosylation at this site and hence largely diminishes Fc γ receptor binding and effector functions (Park H. I. et al. *Trends Biotenchol* 2016 34:895; Arnold J. N. et al. *Annu. Rev. Immunol.* 2007 25:21). The best humanized candidate was named UFKA-22-00, shortened to UFKA-22, bearing a heavy chain of SEQ ID NO 017, and a light chain of SEQ ID NO 018. IL-2/UFKA-22cx and a similar clones sharing the same CDR but bearing framework mutations showed comparable stimulatory activity and selectivity as IL-2/UFKA-20cx in kinetic binding analysis with IL-2 (Table 2), in vitro using freshly-isolated human T cells (FIG. 6), or injected in mice (FIG. 7). Altogether, complexes of IL-2 with UFKA-20 and its humanized version UFKA-22 show strong in vitro activity on human T$_{reg}$ cells, whereas their activity on human CD8$^+$ T cells is markedly reduced compared to uncomplexed, free IL-2.

Example 6: Humanized IL-2/UFKA-22cx Show In Vivo Selectivity for T$_{reg}$ Cells in Rhesus Macaques IL-2R subunits share a high degree of homology between humans and rhesus macaques. Accordingly, a homology search on National Center for Biotechnology Information (NCBI) was performed using the Basic Local Alignment Search Tool (BLAST), finding that identity of CD25, CD122 and CD132 was 91.9% (accession number NP 001028089.1), 94.2% (NP 001244989.1) and 97.3% (NP001030606.1), respectively, between these two species. Both the mouse antibody UFKA-20 and humanized UFKA-22 clone showed similar binding to either macaque or human IL-2 in vitro (data not shown). To compensate for the difference in in vivo half-lives between IL-2 and IL-2/UFKA-22cx, animals were injected daily on days 0 to 6 with IL-2 (aldesleukin) at 10 μg/kg (LD) or 33 μg/kg (HD), whereas IL-2/UFKA-22cx at 10 g/kg IL-2 and 100 μg/kg mAb (LD) or 33 μg/kg IL-2 and 330 μg/kg mAb (HD) were administered on days 0 and 3 (FIG. 8A). Injection of UFKA-22 at 330 μg/kg (without IL-2) on days 0 and 3 served to assess whether it bound endogenous macaque IL-2. Assessment of parameters on day-8 served as baseline and untreated control. pSTAT5 levels were measured one day after the first injection, significantly increased pSTAT5 levels were observed in $CD4^+CD25^+$ T cells following HD IL-2 as well as LD and HD IL-2/UFKA-22cx (FIG. 8B), whereas LD IL-2 or UFKA-22 alone did not alter pSTAT5 levels of $CD4^+CD25^+$ T cells over what was measured at baseline on day-8 (FIG. 8B). Overall, the increase in pSTAT5 levels in $CD4^+CD25^+$ T cells was more pronounced with IL-2/UFKA-22cx than with IL-2. In contrast to $CD4^+$ $CD25^+$ T cells, pSTAT5 levels in $CD4^+CD25^-$, $CD8^+$ $CD25^+$, and $CD8^+CD25^-$ T cells were not significantly changed by IL-2, IL-2/UFKA-22cx or UFKA-22 compared to baseline (FIG. 8B). To assess selectivity of IL-2/UFKA-22cx for $T_{reg}$ cells, dose- and time-dependent changes of $T_{reg}$ cells in the blood of macaques were quantified. We observed the strongest changes on day 6 where percentages of $CD4^+CD25^+Foxp3^+$ T cells and $CD4^+CD25^+$ T cells were significantly higher in animals receiving LD IL-2/UFKA-22cx compared to LD IL-2 (FIG. 8C). $CD4^+CD25^+Foxp3^+$ T cells increased on average up to 29% of total $CD4^+$ T cells after two injections of LD IL-2/UFKA-22cx, whereas seven daily low-dose IL-2 injections only resulted in 4.8% $CD4^+$ $CD25^+$ $Foxp3^+$ T cells (FIG. 8C). HD IL-2 and HD IL-2/ UFKA-22cx resulted in comparable $T_{reg}$ cell responses, although they did not surpass the effects seen with LD IL-2/UFKA-22cx (FIG. 8C). Levels of Foxp3 and cytotoxic T-lymphocyte-associated antigen 4 (CTLA-4) significantly increased in $CD4^+CD25^+$ T cells on days 3 and 6 after injection of LD IL-2/UFKA-22cx compared to LD IL-2, whereas HD IL-2/UFKA-22cx and HD IL-2 did not provide any further advantage (FIG. 8D). Similarly, $CD4^+CD25^+$ T cells became Ki-67+ from day 2 on, with Ki-67 levels peaking on days 3 and 6 (FIG. 8D), which most likely reflected IL-2 signalling-induced cell cycle and proliferation. Injection of UFKA-22 without IL-2 led to a small but distinct reduction of $CD4^+CD25^+$ T cell frequencies (FIG. 8C), which was probably caused by mild neutralization of endogenous macaque IL-2 by UFKA-22. Foxp3, CTLA-4 and Ki-67 expression levels remained unchanged in the UFKA-22 group (FIG. 8D). Calculating the ratios of CD4+ $CD25^+Foxp3^+$ $T_{reg}$ cells to $CD8^+$ T cells, NK cells, and B cells, showed that LD IL-2/UFKA-22cx achieved the best $T_{reg}$ cell selectivity (FIG. 8E). Humanized IL-2/UFKA-22cx in rhesus macaques confirmed the selectivity of these IL-2cx for $CD4^+CD25^+Foxp3^+$ $T_{reg}$ cells, and their superiority over IL-2.

Example 7: UFKA-20 Sterically Interferes with IL-2 Binding to CD122 and CD25

To obtain structural and further mechanistic insight into the IL-2/UFKA-20 interaction, a fragment antigen-binding (Fab) variant of UFKA-20 was generated and complexed with IL-2. The IL-2/UFKA-20 Fab complex was then crystalized for structural analysis. Crystals grew at physiological pH (pH 7.48) and diffracted to 2.89 Å resolution. The structure was solved by molecular replacement and comprised three IL-2/UFKA-20 Fab complexes in the asymmetric unit. Compared to the crystal structure of the human IL-2 quaternary, UFKA-20 bound IL-2 dorsolaterally, with an angle of about 55° anti-clockwise to the vertical axis, and differed markedly from those of IL-2 in complex with F5111 (worldwide protein databank PDB: 5UTZ), JES6-1 (PDB: 4YQX), or NARA1 (PDB: 5LQB) (FIG. 9A). Next, a close analysis of the $CD25^-$, CD122-, and CD132-binding sites was performed. Epitope overlaps were assessed between the anti-IL-2 mAbs and the IL-2R subunits, quantified based on buried surface areas within IL-2cx and the quaternary IL-2R complex using the protein interfaces, surfaces and assemblies software tool. UFKA-20 overlaid strongly with the CD122-binding site of IL-2, resulting in an overlap calculated at 40%, whereas UFKA-20 interference with the CD25-binding site of IL-2 was rather mild and amounted to only 6.3% (FIG. 9B). There was no overlap evident of UFKA-20 with IL-2's CD132-binding site. Thus, via its CDR1-3 of the variable heavy (VA) and CDR1 and CDR3 of the variable light ($V_L$) chain, UFKA-20 predominantly contacted the C- and B-helices of IL-2 thereby forming a 'clamp' around the C-helix (FIG. 9B). The IL-2 residues D84, N88 and V91, usually involved in CD122 interaction, were closely engaged with UFKA-20 (FIG. 9A). These interactions very likely abrogated IL-2 binding to CD122, as shown by surface plasmon resonance (SPR) measurements (FIG. 9C). Furthermore, UFKA-20's $V_H$ chain clashed to a minor but significant extent with CD25 through close contact with IL-2 residues E60, E61 and K64, which locate to the IL-2-CD25 interface (FIG. 9B). However, as measured by SPR, IL-2/UFKA-20cx efficiently bound to recombinant human CD25 in a dose-dependent manner (FIG. 9C). As a result of its multiple contacts, UFKA-20 associated with a high affinity with IL-2, resulting in a $K_d$ of about $10^{-9}$ M (Table 1). F5111 bound to IL-2 at a different angle than UFKA-20, and the F5111 and CD122 epitopes overlapped significantly (calculated at 48.5%), whereas for the CD132 epitope this overlap was very mild (2.5%) and there was no significant overlap with the CD25 epitope (0.85%) (FIGS. 9A and B). JES6-1 interacted with mouse IL-2 in a manner very different from UFKA-20 and F5111. Compared to UFKA-20, JES6-1 bound to the opposite side of IL-2, mainly interfering with CD132 (18%), followed by CD25 (16%) and CD122 (8%) (FIGS. 9A and B). As the quaternary mouse IL-2R complex is unavailable, the IL-2R overlaps of the mouse IL-2/JES6-1cx were calculated using the quaternary human IL-2R crystal. IL-2/NARA1 fully overlapped with CD25, thus 'mimicking' CD25's binding to IL-2. At close observation, NARA1 largely overlapped with the CD25-binding site of IL-2 (52.5%), whereas the CD122- and CD132-binding sites remained fully accessible (0%) (FIGS. 9A and B). Consequently, on SPR, IL-2/NARA1cx very efficiently bound to recombinant human CD122 but not to CD25 (FIG. 9C).

To assess whether UFKA-20 functionally competed with both CD122- and CD25-binding sites of IL-2 as suggested by structural analysis, a competition assay was performed on HEK293T cells expressing different IL-2R subunits using a set concentration of $IL-2_{Rhod}$ and titrated concentrations of UFKA-20. $IL-2_{Rhod}$ binding to $CD122^+CD132$ was diminished already at a 10:1 and 1:1 molar ratio of IL-2 to UFKA-20, thus confirming UFKA-20's functional interference with CD122 (FIG. 9D, middle panel). Conversely, $IL-2_{Rhod}$ binding to CD25 was unperturbed at molar ratios of IL-2 to UFKA-20 of 10:1 and 1:1, whereas five to 50-fold higher UFKA-20 concentrations were needed to compete with CD25-binding (9D, left panel); a similar pattern emerged with HEK293T cells expressing $CD25^+CD122^+$ CD132 (FIG. 9D, right panel). The results of the UFKA20 epitope overlap and buried surface areas within IL-2cx and the quaternary IL-2R complex suggest binding was occurring at three sites of the hIL-2 sequence:

Epitope A comprising H16, D20.

Epitope B comprising Q57, E60, E61, L63, K64, E67, E68.

Epitope C comprising L80, R81, R83, D84, 186, S87, N88, N90, V91, L94, E95, K97, T101, T102, M104.

Epitope A and C overlap the region of IL-2 important for binding with CD122 and CD132 (targeted by F5111), whereas epitope B overlapping the CD25 binding site is uniquely targeted by UFKA-20 compared to existing antibody clones (FIGS. 9, 10 and 11) and is likely to be associated with enhanced effect generated by this clone compared to the >10000 alternatives screened.

Example 8. CDR Mutations Altering UFKA20 Binding to Specific hIL-2 Epitopes

UFKA-20 variants that contain specific amino acid substitutions in $V_H$ (SEQ ID NO 019) and $V_L$ (SEQ ID NO 020) chain were created to investigate the effect of weaker or stronger polar and non-polar interactions between specific CDR loops and the proposed epitopes on hIL-2 (Table 3 and 4). The 7 $V_H$ chain variants contained between 1-3 and 4 $V_L$ chain variants with 2-4 amino acid substitutions. Collectively, 12 different UFKA-20 variants, including the original UFKA-20 mAb, were expressed, purified and subsequently their affinity and in vivo activity (FIG. 12) was determined. The affinities of the variant antibodies ranged from $6.403\times10^{-8}$ M to $1.856\times10^{-10}$ M, 2+9 was the lowest and 5+9 the highest among variants tested. Most of the antibody variants bind in the 10-10 M range, clustering around the affinity of the unmodified original 1+6 (UFKA-20) antibody. C57BL/6 wildtype mice were administered a single dose of IL-2/anti-IL-2cx of the UFKA-20 variants. Frequencies of $CD4^+$ $CD25^+Foxp3^+$ cells were not significantly altered by antibodies comprising variants 5+9; 4+9; 4+10; 2+9 (FIG. 12B), indicating that these variants lacked optimal interactions with residues in the hIL-2 epitopes B (for example E61, Q57, R83) and C (L94, and E95) which were affected by the residue substitutions in these variant chains (Table 4), and that interaction with both is essential for high efficacy of hIL-2 complexes formed with the antibody according to the invention. Of note, epitope B is uniquely targeted by UFKA-20 derived antibodies compared to known clones with capacity to form CD25-targeted complexes (FIG. 10). Most of the tested antibodies, including 105+6, 105+9, 2+9, 103+6, and 103+9 were very similar to UFKA-20 (1+6) in terms of $CD4+CD25^+Foxp3^+$ $T_{reg}$ cell stimulation, showing the sequence is tolerant to certain amino acid changes in the CDR regions, provided the residues S56, M100, Y102, in humanized antibodies derived from SEQ ID NO 019, and K36, F56, S32, A33, and A100 of SEQ ID NO 020 maintain their optimal orientation to interact with IL-2 epitopes B and C.

A correlation could be observed between $K_D$ values and a capacity to increase the frequency of $CD4^+CD25^+Foxp3^+$ $T_{reg}$ cells in the mediated by $T_{reg}$ cell stimulation (FIG. 12C). Excepting antibodies 2+9 and 4+10, the antibodies' activity clustered around the UFKA-20 (1+6) antibody, suggesting that the optimal affinity lies in the 10-10M range. However, the 5+9 antibody that bound IL-2 with the highest affinity had reduced in vivo activity with regards to $CD4^+$ $CD25^+Foxp3^+$ $T_{reg}$ cell stimulation, suggesting an upper affinity limit of $1.856^{-10}$.

Example 9. Fusion Proteins of IL-2 and UFKA-22 Antibody

Although CD25-biased immune complexes have excellent immunomodulatory potential, they are yet to gain approval for use inhibiting inflammatory responses in humans, as several aspects of their biology create problems which have impeded clinical development. Firstly, IL-2 antibody complexes formed by incubating IL-2 with anti-IL-2 antibodies at 37 degrees must be prepared immediately prior to administration to avoid degradation into separate components. This is inconvenient in a clinical setting, and can lead to small differences in activity between batches. In addition, the complexes may dissociate in vivo, producing soluble IL-2 with the potential to produce undesirable off-target signalling. To overcome these problems, a single-agent drug compound was developed to replace IL-2/ UFKA-22cx therapy—a two component immunotherapy consisting of recombinant human IL-2 and the humanized CD25-biased anti-IL-2 antibody UFKA-22—with IL-2/ UFKA-22 fusion proteins retaining optimal signalling through CD25, combined with improved stability (UFKA-22FP).

For the UFKA-22FP design, the IL-2 protein and the UFKA-22 antibody must be connected by a flexible linker facilitating optimal rates of not just IL-2-association, but importantly, dissociation from the IL-2-binding groove of the UFKA-22 antibody, such that IL-2 signalling through the dimeric IL-2R ($CD122^+CD132$) is not impeded by the joined antibody structure. The crystal structure of the IL-2/ UFKA-20cx (PDB: 6YE3) was analysed to determine the distance between N-terminus of the UFKA-20 variable heavy ($V_H$) and variable light ($V_L$) chain to the C-terminus of IL-2 with 32.2 Å and 43.5 Å, respectively (FIGS. 12A and B). Subsequently, UFKA-22FPs joining an N-terminal IL-12 polypeptide (Uniprot P60568) to the UFKA-22 $V_H$ (SEQ ID NO 017), or $V_L$ chains (SEQ ID NO 018) with flexible glycine (G) serine(S) linkers consisting of (G4S)$_n$ (SEQ ID NO 023), with n number of repeats ranging from 3 to 6 were generated to test which linker offers optimal CD25-targeted signalling though IL-2R (FIGS. 13C and D, and 14). UFKA-22FP vH (G$_4$S)$_3$, UFKA-22FP vH (G4S) 4, UFKA-22FP vH (G4S) 5 and UFKA-22FP vL (G4S) 6, were expressed downstream of a secretion signal (SEQ ID NO 027), and obtained from suspension cultures of HEK293 FreeStyle cells purified over a HiTrap® Protein G column. The UFKA-22FPs were tested for binding the CD25 mimo-body-NARA1-in an ELISA. All four UFKA-22FP variants bound NARA1, indicating that the IL-2 domain of UFKA-22FPs was folded correctly. IL-2 bioactivity was measured in a cell proliferation assay using mouse CTLL-2 cells that express all three IL-2R subunits, an induction of STAT5 signalling assay in HEK-Blue IL-2 reporter cells that express human IL-2RaBy, and $T_{reg}$ stimulation was confirmed in human PBMCs. Once the activity and $T_{reg}$-selectivity of fusion proteins was confirmed for all fusion proteins, and the most promising candidates were selected for further testing in mice.

C57BL/6 WT mice received daily injections for three days of IL-2/UFKA-22cx, UFKA-22FP vH (G4S) 5 and UFKA-22FP vL (G4S) 6 (comprising hIL-2 LC fusion SEQ ID NO 028), followed by flow cytometry analysis of $CD4^+$ $CD25^+Foxp3^+$ $T_{reg}$, $CD8^+CD44^{hi}$ $CD122^+$ memory T, and $CD3-NK1.1^+$ $CD122^+NK$ cells in spleens of treated animals. Because UFKA-22FP molecules constitute one UFKA-22 antibody and two IL-2 molecules, a 2:1 molar ratio of IL-2 to UFKA-22 antibody was used for the IL-2/UFKA-22cx formulation. Three injections of UFKA-22FP vH (G$_4$S)$_5$ slightly increased the $CD25^+Foxp3^+$ $T_{reg}$ cell compartment but the changes were not significant at the applied doses. In contrast, UFKA-22FP vL (G$_4$S)$_6$ significantly increased $CD25^+Foxp3^+$ $T_{reg}$ cell frequencies to 15.2±1.2% in the spleen at the 12 µg dose, and the 24 µg dose reached 20.6±1.4%. Treatment with UFKA-22FP vL (G4S) 6 induced a dose-dependent increase in Ki-67 expression in CD4$^+$CD25$^+$Foxp3$^+$ T$_{reg}$ cells, with 42.0±5.5% and 64.1±3.7% of CD4$^+$CD25$^+$Foxp3$^+$ T$_{reg}$ cells upregulating Ki-67 in response to 12 μg and 24 μg UFKA-22FP vL (G4S) 6, respectively. A significant increase in Ki-67+CD4$^+$CD25$^+$ Foxp3$^+$ T$_{reg}$ cells was observed in mice that received 24 μg UFKA-22FP vL (G4S) 6 was very comparable to the 70.9±1.1% Ki-67+observed in mice injected with 12 μg of IL-2/UFKA-22cx. No significant changes in the CD8$^+$ T cell frequencies were observed, demonstrating the fusion protein did not create off-target effects on cytotoxic CD8$^+$ T cells. UFKA-22FP activity was reduced compared to IL-2/UFKA-22cx, but UFKA-22FP vL (G4S) 6 approached a similar activity at a slightly higher dose (FIG. 14). In summary, a peptide linker length of 30 amino acids to the light chain is preferable. The linkage of IL-2 to the antibody heavy chain is feasible as well. These results suggest that a fusion protein with desirable manufacturing and pharmaceutical safety properties can achieve equivalent effect in vivo in comparison to a two-component IL-2cx, albeit at a moderately increased dosage.

Example 10: IL-2 Immunotherapy Expands cDCs in Mice and Humans

DCs are characterized by the absence of lineage (Lin) markers, have intermediate (int) or high (hi) CD11c, and can further be subdivided into CD11c$^{int}$ B220$^{hi}$ pDCs, CD11c$^{hi}$ major histocompatibility class II (MHC-II) hi cDCs, CD11b$^{low}$ XCR1$^+$CD8α$^+$DNGR-1 (CLEC9A)$^+$cDC1s, and CD11b$^{hi}$ XCR1$^-$ cDC2s (FIG. 15A). A short course of three injections of recombinant human IL-2 (IL-2; teceleukin) increased total counts of cDCs in spleens of adult wild-type (WT) mice (FIG. 15B). This expansion was due to active proliferation of cDCs, as evidenced by increased incorporation of the thymidine analogue bromodeoxyuridine (BrdU) into cDCs (FIG. 15C). To assess whether this IL-2 effect was caused by binding of IL-2 to CD25$^{hi}$ or CD122$^{hi}$ cells, CD25-biased IL-2/anti-IL-2 (5344) antibody complexes (IL-2/5344) and CD122-biased IL-2/anti-IL-2 (NARA1) antibody complexes (IL-2/NARA1) were tested (Letourneau E. M. PNAS 2010, 107:11906; Krieg C. PNAS 2010, 107:11906, Arenas-Ramirez N. Sci Transl Med 2016). Both IL-2/5344 and IL-2/NARA1 mouse IL-2/antibody complexes stimulated quantitatively comparable expansion and proliferation of splenic DCs as unbiased IL-2 (FIG. 15B, C): Treatment of mice with IL-2cx comprising an inflammatory, CD122-targeted IL-2 antibody induced upregulation of CD40, CD80, CD86, and MHC class I (MHC-I), but not MHC-II, on cDCs (FIG. 15D), indicating maturation of cDCs with increased potential of cross-presentation and co-stimulation for T cell activation.

Human CD11c$^+$ MHC-II (HLA-DR)+DCs were examined within an investigator-initiated clinical trial (termed Charact-IL-2; NCT 03312335) using recombinant hIL-2 (aldesleukin) immunotherapy (FIG. 16A). Clinical trials testing aldesleukin have reported the proliferation of CD4$^+$ and CD8$^+$ T cells and NK cells upon aldesleukin immunotherapy (Klatzmann D. et al. Nat Rev Immunol 2015, 15:283; Humrich J. Y et al. Lancet Rheumatol 2019, 1: e44). However, by comparing Ki67$^+$ DCs on day 0 (before) and day 5 (1 day after the last injection) of a 5-day course of daily aldesleukin, an increase of proliferating cDC1s and cDC2s was observed (FIG. 16B).

The parenteral administration of UFKA20 complexes (IL-2 bound to the CD25-biased antibody UFKA20) also expanded cDCs in the spleen of murine recipients (FIG. 17A), inducing proliferation of cDCs, as measured by BrdU incorporation (FIG. 17B). Treatment with a pharmaceutical composition comprising UFKA20 complexes downregulated MHC-II and CD80 (FIGS. 17C and D), indicating complexes with CD25-targeted antibodies reduce the capacity of cDCs to present antigen and transmit co-stimulatory signals to T cells. Treatment with UFKA20 complexes further induced upregulation of the immune regulatory protein programmed cell death protein 1 (PD-1), programmed cell death ligand 1 (PD-L1) and PD-L2 expressed on cDCs (FIG. 17E). Immunoregulatory genes were upregulated in UFA20 complex treated mice (positive values on x-axis) including transforming growth factor beta-induced (Tgfbi), interleukin 1 receptor antagonist (Il1rn), and TGF-beta activated kinase 1/MAP3K7 binding protein 1 (Tab1). Immunostimulatory genes including interleukin 6 signal transducer (Il6st), lymphotoxin beta (Ltb), tumor necrosis factor (ligand) superfamily member 14 (Tnfsf14), and colony stimulating factor 1 (Csf1) were downregulated in UFKA20 complex treated mice (negative values on x-axis). Additionally, UFKA20 complex treated cDCs downregulated TNF receptor superfamily member 6 (Fas), suggesting prolonged survival (FIG. 17F). In summary, the presented data shows that a pharmaceutical compound comprising UFKA20 promotes proliferation of cDCs with a tolerogenic phenotype and immunoregulatory properties.

TABLE 1

| Anti-IL-2 mAb | | | |
| --- | --- | --- | --- |
| clone | ka (1/Ms) | kd (1/s) | KD (M) |
| JES6-1 | | | $5.60 \times 10^{-9}$ |
| UFKA-20 | $2.57 \times 10^5$ | $3.91 \times 10^{-4}$ | $2.30 \times 10^{-9}$ |
| UFKA-22-00 | $4.66 \times 10^5$ | $2.39 \times 10^{-3}$ | $5.13 \times 10^{-9}$ |
| UFKA-22-02 | $4.12 \times 10^5$ | $2.27 \times 10^{-3}$ | $5.51 \times 10^{-9}$ |
| UFKA-22-07 | $4.86 \times 10^5$ | $2.51 \times 10^{-3}$ | $4.45 \times 10^{-9}$ |
| NARA1 | $3.00 \times 10^4$ | $1.17 \times 10^{-4}$ | $4.20 \times 10^{-9}$ |
| F5111 | $3.78 \times 10^6$ | $7.11 \times 10^{-3}$ | $1.88 \times 10^{-9}$ |

TABLE 2

| IL-2 binding properties of UFKA-22 variants Variants in bold were evaluated in vivo, in mice or rhesus macaques. | | | | | | | |
| --- | --- | --- | --- | --- | --- | --- | --- |
| mAb ID | VH | SEQ NO ID | VL | SEQ NO ID | ka (1/Ms) | kd (1/s) | KD (M) |
| UFKA-22-00 (UFKA-22) | VH1 | 007 | zVK1 | 015 | 4.66E+05 | 2.39E−03 | 5.13E−09 |
| UFKA-22-01 | VH2 | 008 | VK1 | 015 | 4.75E+05 | 2.52E−03 | 5.31E−09 |
| UFKA-22-02 | VH3 | 009 | VK1 | 015 | 4.12E+05 | 2.27E−03 | 5.51E−09 |
| UFKA-22-03 | VH4 | 010 | VK1 | 015 | 5.90E+05 | 2.79E−03 | 4.73E−09 |
| UFKA-22-04 | VH5 | 011 | VK1 | 015 | 4.79E+05 | 2.41E−03 | 5.03E−09 |

TABLE 2-continued

IL-2 binding properties of UFKA-22 variants
Variants in bold were evaluated in vivo, in mice or rhesus macaques.

| mAb ID | VH | SEQ NO ID | VL | SEQ NO ID | ka (1/Ms) | kd (1/s) | KD (M) |
|---|---|---|---|---|---|---|---|
| UFKA-22-05 | VH6 | 012 | VK1 | 015 | 4.52E+05 | 2.20E−03 | 4.86E−09 |
| UFKA-22-06 | VH7 | 013 | VK1 | 015 | 5.67E+05 | 2.52E−03 | 4.45E−09 |
| UFKA-22-07 | VH1 | 007 | VK2 | 016 | 4.86E+05 | 2.51E−03 | 5.17E−09 |
| UFKA-22-08 | VH2 | 008 | VK2 | 016 | 5.15E+05 | 2.75E−03 | 5.33E−09 |
| UFKA-22-09 | VH3 | 009 | VK2 | 016 | 4.66E+05 | 2.46E−03 | 5.27E−09 |
| UFKA-22-10 | VH4 | 010 | VK2 | 016 | 5.48E+05 | 2.83E−03 | 5.16E−09 |
| UFKA-22-11 | VH5 | 011 | VK2 | 016 | 5.17E+05 | 2.75E−03 | 5.31E−09 |
| UFKA-22-12 | VH6 | 012 | VK2 | 016 | 4.74E+05 | 2.40E−03 | 5.05E−09 |
| UFKA-22-13 | VH7 | 013 | VK2 | 016 | 6.07E+05 | 2.77E−03 | 4.56E−09 |
| UFKA-22-14 | VH8 | 014 | VK2 | 016 | 5.60E+05 | 2.40E−03 | 4.30E−09 |

$V_H$ heavy variable chain,
$V_L$ light variable chain

TABLE 3

VH (SEQ ID NO 019) and VL (SEQ ID NO 020)
alterations in UFKA-20 variants

| Variant | Variable chain | Amino acid substitution |
|---|---|---|
| 1 | vH | — |
| 2 | vH | S56R-Y102K |
| 3 | vH | S56R-M100L-Y102K |
| 4 | vH | S56R-Y102H |
| 5 | vH | S56R-M100L-Y102H |
| 6 | vL | — |
| 7 | vL | S32V-A33S-A100C |

TABLE 3-continued

VH (SEQ ID NO 019) and VL (SEQ ID NO 020)
alterations in UFKA-20 variants

| Variant | Variable chain | Amino acid substitution |
|---|---|---|
| 8 | vL | S32V-A33S-K36R-F56W-A100C |
| 9 | vL | K36R-F56W |
| 10 | vL | S32V-A33S-K36R-A100C |
| 103 | vH | N103A |
| 104 | vH | D104L |
| 105 | vH | Y105A |

TABLE 4

Role of amino acid substitutions in UFKA20 variants

| Amino acid substitution | Purpose of substitution |
|---|---|
| vH S56R | Positively charged side chain to strengthen interaction with epitope B (e.g. E61) on hIL-2 |
| vH M100L | Hydrophobic side chain to optimize interaction with epitope C (e.g. L94) on hIL-2 |
| vH Y102K | Positively charged side chain to strengthen interaction with epitope B (e.g. E61, Q57) on hIL-2 |
| vH Y102H | Positively charged side chain to strengthen interaction with epitope B (e.g. E61, Q57) on hIL-2 |
| vH N103A | Hydrophobic side chain to reduce interaction with epitope B on hIL-2 |
| vH D104L | Hydrophobic side chain to reduce interaction with epitope B on hIL-2 |
| vH Y105A | Hydrophobic side chain to reduce interaction with epitope B on hIL-2 |
| vL S32V | Hydrophobic side chain to optimize interaction with epitope C on hIL-2 |
| vL A33S | Polar uncharged side chain to optimize interaction with epitope C on hIL-2 |
| vL K36R | Positively charged side chain to strengthen interaction with epitope C (e.g. E95) on hIL-2 |
| vL F56W | Hydrophobic side chain to optimize interaction with epitope C on hIL-2 |
| vL A100C | Side chain to optimize interaction with epitope B (e.g. R83) on hIL-2 |

| SEQ ID NO | NAME | SEQUENCE |
|---|---|---|
| 001 | CDR$_H$1 | GFSFSNYAMS |
| 002 | CDR$_H$2 | LISGGGSYSYYPDSLKG |
| 003 | CDR$_H$3 | HMGYNDYLAWFAY |
| 004 | CDR$_L$1 | KSSQSLLNSANQKNYLA |
| 005 | CDR$_L$2 | FASTRES |
| 006 | CDR$_L$3 | QQYYSAPPWT |

-continued

| SEQ ID NO | NAME | SEQUENCE |
|---|---|---|

007    V$_H$1

EVQLVESGGGLVKPGGSLRLSCAASGFSFSNYAMSWVRQAPGKGLEWVS**LI
SGGGSYSYYPDSLKGRFTISRDNAKNSLYLQMNSLRAEDTAVYYCARHMGY
NDYLAWFAY**WGQGTLVTVSS

008    V$_H$2

EVQLVESGGGLVKPGGSLRLSCAASGFSFSNYAMSWVRQAPGKGLEWVS**LI
SGGGSYSYYPDSLKGRFTISRDSAKNSLYLQMNSLRAEDTAVYYCARHMGY
NDYLAWFAY**WGQGTLVTVSS

009    V$_H$3

EVQLVESGGGLVKPGGSLRLSCAASGFSFSNYAMSWVRQAPGKGLEWVS**LI
SGGGSYSYYPDSLKGRFTISRDNAKNSLYLQMSSLRAEDTAVYYCARHMGY
NDYLAWFAY**WGQGTLVTVSS

010    V$_H$4

EVQLVESGGGLVKPGGSLRLSCAASGFSFSNYAMSWVRQAPGKGLEWVS**LI
SGGGSYSYYPDSLKGRFTISRDSAKNSLYLQMSSLRAEDTAVYYCARHMGY
NDYLAWFAY**WGQGTLVTVSS

011    V$_H$5

EVQLVESGGGLVKPGGSLRLSCAASGFSFSNYAMSWVRQAPGKGLEWVS**LI
SGGGSYSYYPDSLKGRFTISRDSAKNSLYLQMNSLRAEDTAMYYCARHMGY
NDYLAWFAY**WGQGTLVTVSS

012    V$_H$6

EVQLVESGGGLVKPGGSLRLSCAASGFSFSNYAMSWVRQAPGKGLEWVS**LI
SGGGSYSYYPDSLKGRFTISRDNAKNSLYLQMSSLRAEDTAMYYCARHMGY
NDYLAWFAY**WGQGTLVTVSS

013    V$_H$7

EVQLVESGGGLVKPGGSLRLSCAASGFSFSNYAMSWVRQAPGKGLEWVS**LI
SGGGSYSYYPDSLKGRFTISRDSAKNSLYLQMSSLRAEDTAMYYCARHMGY
NDYLAWFAY**WGQGTLVTVSS

014    V$_H$8

EVQLVESGGGLVKPGGSLRLSCAASGFSFSNYAMSWVRQAPGKGLEWVS**LI
SGGGSYSYYPDSLKGRFTISRDNAKNSLYLQMNSLRAEDTAVYYCARHMGY
NDYLAWFAY**WGQGTLVTVSA

015    V$_L$1

DIVMTQSPDSLAVSLGERATINCKSSQSLLNSANQKNYLAWYQQKPGQPPK
LLIYFASTRESGVPDRFSGSGSGTDFTLTISSLQAEDVAVYYC**QQYYSAPP
WT**FGGGTKVEIK

016    V$_L$2

DIVMTQSPDSLAVSLGERATINCKSSQSLLNSANQKNYLAWYQQKPGQPPK
LLIYFASTRESGVPDRFIGSGSGTDFTLTISSLQAEDVAVYYC**QQYYSAPP
WT**FGGGTKVEIK

017    V$_H$

EVQLVESGGGLVKPGGSLRLSCAASGFSFSNYAMSWVRQAPGKGLEWVS**LI
SGGGSYSYYPDSLKGRFTISRDNAKNSLYLQMNSLRAEDTAVYYCARHMGY
NDYLAWFAY**WGQGTLVTVSSASTKGPSVFPLAPSSKSTSGGTAALGCLVKD
YFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDT
LMISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK

018    V$_L$

DIVMTQSPDSLAVSLGERATINCKSSQSLLNSANQKNYLAWYQQKPGQPPK
LLIYFASTRESGVPDRFSGSGSGTDFTLTISSLQAEDVAVYYC**QQYYSAPP
WT**FGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEVT
HQGLSSPVTKSFNRGEC

019    UFKA-20 HC

EVMLVESGGGLVKPGGSLKLSCAASGFSFSNYAMSWVRQTPERRLEWVA**LI
SGGGSYSYYPDSLKGRFTISRDSARNSLYLQMSSLRSEDTAMYYCARHMGY
NDYLAWFAY**WGQGTLVTVSSAKTTPPSVYPLAPGSAAQTNSMVTLGCLVKG
YFPEPVTVTWNSGSLSSGVHTFPAVLQSDLYTLSSSVTVPSSTWPSQTVTC
NVAHPASSTKVDKKIVPRDCGCKPCICTVPEVSSVFIFPPKPKDVLMISLT
PKVTCVVVDISKDDPEVQFSWFVDDVEVHTAQTKPREEQINSTFRSVSELP
ILHQDWLNGKEFKCRVNSAAFPAPIEKTISKTKGRPKAPQVYTIPPPKEQM
AKDKVSLTCMITNFFPEDITVEWQWNGQPAENYKNTQPIMDTDGSYFVYSK
LNVQKSNWEAGNTFTCSVLHEGLHNHHTEKSLSHSPGK

020    UFKA-20 LC

DIVMTQSPSSLAVSVGQKVTMSCKSSQSLLNSANQKNYLAWYQQKPGQSPK
LLIYFASTRESGVPDRFIGSGSGTDFTLNISSVQAEDLADYFC**QQYYSAPP
WT**FGGGTKLEIKRADAAPTVSIFPPSSEQLTSGGASVVCFLNNFYPKDINV
KWKIDGSERQNGVLNSWTDQDSKDSTYSMSSTLTLTKDEYERHNSYTCEAT
HKTSTSPIVKSFNRNEC

021    Spacer motif

GGGGS

-continued

| SEQ ID NO | NAME | SEQUENCE |
|---|---|---|
| 022 | Cypet primer f | CGTCTCGTGGTGGTGGTTCTGGTGGTGGTGGTTCTGTGACAAGG |
| 023 | Cypet primer r | GGTGGTCTCGAGTTATTTGTACAGTTCGTCCATGCCG |
| 024 | CD25 primer f | CTAGGAAGCTTATCTATGGATTCATACCTGCTG |
| 025 | CD25 primer r | ACCAGAACCACCACCACCAGAACCACCACCACCGATTGTTCTTCTACTCTT CCTCTG |
| 026 | linker | GGGGSGGGGSGGGGSGGGGSGGGGSGGGGS |
| 027 | Signal peptide | MPLLLLLPLLWAGALA |
| 028 | hIL2 fusion protein (G₄S)₆ | PTSSSTKKTQLQLEHLLLDLQMILNGINNYKNPKLTRMLTFKFYMPKKATE LKHLQCLEEELKPLEEVLNLAQSKNFHLRPRDLISNINVIVLELKGSETTF MCEYADETATIVEFLNRWITFSQSIISTLTGGGGSGGGGSGGGGSGGGGSG GGGSGGGGSDIVMTQSPDSLAVSLGERATINCKSSQSLLNSANQKNYLAWY QQKPGQPPKLLIYFASTRESGVPDRFSGSGSGTDFTLTISSLQAEDVAVYY CQQYYSAPPWTFGGGTKVEIKRTVAAPSVFIFPPSDEQLKSGTASVVCLLN NFYPREAKVQWKVDNALQSGNSQESVTEQDSKDSTYSLSSTLTLSKADYEK HKVYACEVTHQGLSSPVTKSFNRGEC |

---

The invention claimed is:

1. A human interleukin-2 (hIL-2)-specific monoclonal antibody (mAb), or antigen-binding fragment thereof, wherein the hIL-2-specific mAb interacts with hIL-2 amino acid residues to provide an epitope, and wherein the epitope comprises the hIL-2 residues H16, D20,
Q57, E60, E61, L63, K64, E67, E68, and
L80, R81, R83, D84, I86, S87, N88, N90, V91, L94, E95, K97, T101, T102, M104;

wherein the hIL-2-specific mAb, or antigen-binding fragment thereof comprises a heavy chain variable ($V_H$) region comprising a $V_H$ complementarity determining region $CDR_H1$, $CDR_H2$ and $CDR_H3$, and a variable light chain ($V_L$) region comprising a $V_L$ complementarity determining region $CDR_L1$, $CDR_L2$ and $CDR_L3$, and wherein a. $CDR_H1$ comprises, or is identical to SEQ ID NO 001; and
b. $CDR_H2$ comprises, or is identical to SEQ ID NO 002, and
c. $CDR_H3$, comprises, or is identical to SEQ ID NO 003; and
d. $CDR_L1$ comprises, or is identical to SEQ ID NO 004; and
e. $CDR_L2$ comprises, or is identical to SEQ ID NO 005; and
f. $CDR_L3$ comprises, or is identical to SEQ ID NO 006.

2. A hIL-2-specific mAb, or antigen-binding fragment thereof, according to claim 1, wherein the binding of the hIL-2-specific mAb to hIL-2 is characterized by:
a dissociation constant ($K_D$) equal or smaller than ($\leq$) $5.51 \times 10^{-9}$,
an on-rate ($K_{on}$) equal or greater than ($\geq$) $4.12 \times 10^5$ $Ms^{-1}$, and
an off-rate ($K_{off}$)$\leq$$83 \times 10$–3 $s^{-1}$.

3. The hIL-2-specific mAb, or antigen-binding fragment thereof, according to claim 1, wherein a complex of the hIL-2-specific mAb and hIL-2 combined in a ratio between 2:1 to 1:2 is characterized by:

a ratio of binding to the high-affinity hIL-2 receptor compared to the intermediate-affinity hIL-2 receptor of between 20 to 121, and/or a ratio of binding affinity for CD25 alone, compared to the intermediate-affinity hIL-2 receptor of between 277 to 483, and/or dissociation of the hIL-2 mAb from hIL-2 on binding of the complex to the high-affinity hIL-2 receptor, and/or activating human $CD3^+CD4^+CD127^{low}$ $Foxp3^+$ $T_{reg}$ cells with an $EC50{\leq}0.154$, and human $CD8^+$ T cells with an $EC50{\geq}442.9$.

4. A hIL-2-specific mAb, or antigen-binding fragment thereof, which comprises a heavy chain variable ($V_H$) region comprising a $V_H$ complementarity determining region $CDR_H1$, $CDR_H2$ and $CDR_H3$, and a variable light chain ($V_L$) region comprising a $V_L$ complementarity determining region $CDR_L1$, $CDR_L2$ and $CDR_L3$, and wherein a. $CDR_H1$ comprises, or is identical to SEQ ID NO 001; and b. $CDR_H2$ comprises, or is identical to SEQ ID NO 002, and c. $CDR_H3$, comprises, or is identical to SEQ ID NO 003; and d. $CDR_L1$ comprises, or is identical to SEQ ID NO 004; and e. $CDR_L2$ comprises, or is identical to SEQ ID NO 005; and f. $CDR_L3$ comprises, or is identical to SEQ ID NO 006.

5. A hIL-2-specific mAb, or antigen-binding fragment thereof, according to claim 1, wherein a. the $CDR_H1$, $CDR_H2$ and $CDR_H3$ are comprised in a $V_H$ sequence selected from SEQ ID NO 007, SEQ ID NO 008, SEQ ID NO 009, SEQ ID NO 010, SEQ ID NO 011, SEQ ID NO 012, SEQ ID NO 013, and SEQ ID NO 014, and wherein, b. the $CDR_L1$, $CDR_L2$ and $CDR_L3$ are comprised in a $V_L$ sequence selected from SEQ ID NO 015, and SEQ ID NO 016.

6. The hIL-2-specific mAb, or antigen-binding fragment thereof, according to claim 1, and further comprising a. a first sequence $\geq$90% identical, to at least one of SEQ ID NO 007, SEQ ID NO 008, SEQ ID NO 009, SEQ ID NO 010, SEQ ID NO 011, SEQ ID NO 012, SEQ ID NO 013, SEQ ID NO 014, and SEQ ID NO 017; and b. a second sequence $\geq$90% identical to at least one of SEQ ID NO 015, SEQ ID NO 016, and SEQ ID NO 018.

7. The hIL-2-specific mAb according to claim 1, wherein the hIL-2-specific mAb comprises:

a. a heavy chain, said heavy chain comprising or consisting of SEQ ID NO 017; and b. a light chain, said light chain comprising or consisting of SEQ ID NO 018.

8. A nucleic acid molecule encoding the hIL-2-specific mAb, or antigen-binding fragment thereof, according to claim 1.

9. A method of treatment for immune-mediated diseases comprising:

administrating to a patient in need an effective amount of a pharmaceutical composition a. the hIL-2-specific mAb, or antigen-binding fragment thereof, according to claim 1, and b. hIL-2, wherein the immune-mediated disease is selected from systemic lupus erythematosus, rheumatoid arthritis, ankylosing spondylitis, autoimmune hepatitis, amyotrophic lateral sclerosis, type-1 diabetes mellitus, type-2 diabetes mellitus, atherosclerosis, multiple sclerosis, inflammatory and autoimmune myopathies, alopecia areata, psoriasis or inflammatory bowel disease thereby treating the immune-mediated diseases.

10. The method of claim 9, wherein the IL-2 and the hIL-2-specific mAb are covalently associated.

11. The method of claim 9, wherein the allograft related disorder is diagnosed in a patient receiving a solid organ transplant procedure.

\* \* \* \* \*

SEQUENCE LISTING

<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: Antibody

<400> SEQUENCE: 1

Gly Phe Ser Phe Ser Asn Tyr Ala Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Antibody

<400> SEQUENCE: 2

Leu Ile Ser Gly Gly Gly Ser Tyr Ser Tyr Tyr Pro Asp Ser Leu Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Antibody

<400> SEQUENCE: 3

His Met Gly Tyr Asn Asp Tyr Leu Ala Trp Phe Ala Tyr
1               5                   10

<210> SEQ ID NO 4

```
<211> LENGTH: 17
<212> TYPE: PRT
<213> ORGANISM: Artificial Sequence
<220> FEATURE:
<223> OTHER INFORMATION: Antibody

<400> SEQUENCE: 4

Lys Ser Ser Gln Ser Leu Leu Asn Ser Ala Asn Gln Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Antibody

<400> SEQUENCE: 5

Phe Ala Ser Thr Arg Glu Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Antibody

<400> SEQUENCE: 6

Gln Gln Tyr Tyr Ser Ala Pro Pro Trp Thr
1               5                   10

<210> SEQ ID NO 7
<211> LENGTH: 122
<212> TYPE: PRT
<213> ORGANISM: Artificial Sequence
<220> FEATURE:
<223> OTHER INFORMATION: Heavy chain variable

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val
            35                  40                  45

Ser Leu Ile Ser Gly Gly Gly Ser Tyr Ser Tyr Tyr Pro Asp Ser Leu
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Met Gly Tyr Asn Asp Tyr Leu Ala Trp Phe Ala Tyr Trp
                100                 105                 110

Gly Gln Gly Thr Leu Val Thr Val Ser Ser
        115                 120

<210> SEQ ID NO 8
<211> LENGTH: 122
<212> TYPE: PRT
<213> ORGANISM: Artificial Sequence
<220> FEATURE:
```

<223> OTHER INFORMATION: Heavy chain variable

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val
        35                  40                  45

Ser Leu Ile Ser Gly Gly Gly Ser Tyr Ser Tyr Tyr Pro Asp Ser Leu
    50                  55                  60

Lys Gly Arg Phe Thr Ile Ser Arg Asp Ser Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Met Gly Tyr Asn Asp Tyr Leu Ala Trp Phe Ala Tyr Trp
            100                 105                 110

Gly Gln Gly Thr Leu Val Thr Val Ser Ser
        115                 120

<210> SEQ ID NO 9
<211> LENGTH: 122
<212> TYPE: PRT
<213> ORGANISM: Artificial Sequence
<220> FEATURE:
<223> OTHER INFORMATION: heavy chain variable

<400> SEQUENCE: 9

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val
        35                  40                  45

Ser Leu Ile Ser Gly Gly Gly Ser Tyr Ser Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg His Met Gly Tyr Asn Asp Tyr Leu Ala Trp Phe Ala Tyr Trp
            100                 105                 110

Gly Gln Gly Thr Leu Val Thr Val Ser Ser
        115                 120

<210> SEQ ID NO 10
<211> LENGTH: 122
<212> TYPE: PRT
<213> ORGANISM: Artificial Sequence
<220> FEATURE:
<223> OTHER INFORMATION: Heavy chain

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val

-continued

```
            35                  40                  45
Ser Leu Ile Ser Gly Gly Gly Ser Tyr Ser Tyr Tyr Pro Asp Ser Leu
    50                  55                  60

Lys Gly Arg Phe Thr Ile Ser Arg Asp Ser Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg His Met Gly Tyr Asn Asp Tyr Leu Ala Trp Phe Ala Tyr Trp
            100                 105                 110

Gly Gln Gly Thr Leu Val Thr Val Ser Ser
        115                 120
```

```
<210> SEQ ID NO 11
<211> LENGTH: 122
<212> TYPE: PRT
<213> ORGANISM: Artificial Sequence
<220> FEATURE:
<223> OTHER INFORMATION: Heavy chain variable

<400> SEQUENCE: 11

Glu Val Gln Leu Val Glu Ser Gly Gly Gly Leu Val Lys Pro Gly Gly
1                   5                   10                  15

Ser Leu Arg Leu Ser Cys Ala Ala Ser Gly Phe Ser Phe Ser Asn Tyr
                20                  25                  30

Ala Met Ser Trp Val Arg Gln Ala Pro Gly Lys Gly Leu Glu Trp Val
            35                  40                  45

Ser Leu Ile Ser Gly Gly Gly Ser Tyr Ser Tyr Tyr Pro Asp Ser Leu
    50                  55                  60

Lys Gly Arg Phe Thr Ile Ser Arg Asp Ser Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg His Met Gly Tyr Asn Asp Tyr Leu Ala Trp Phe Ala Tyr Trp
            100                 105                 110

Gly Gln Gly Thr Leu Val Thr Val Ser Ser
        115                 120
```

```
<210> SEQ ID NO 12
<211> LENGTH: 122
<212> TYPE: PRT
<213> ORGANISM: Artificial Sequence
<220> FEATURE:
<223> OTHER INFORMATION: Heavy chain variable

<400> SEQUENCE: 12

Glu Val Gln Leu Val Glu Ser Gly Gly Gly Leu Val Lys Pro Gly Gly
1                   5                   10                  15

Ser Leu Arg Leu Ser Cys Ala Ala Ser Gly Phe Ser Phe Ser Asn Tyr
                20                  25                  30

Ala Met Ser Trp Val Arg Gln Ala Pro Gly Lys Gly Leu Glu Trp Val
            35                  40                  45

Ser Leu Ile Ser Gly Gly Gly Ser Tyr Ser Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Met Tyr Tyr Cys
                85                  90                  95
```

-continued

```
Ala Arg His Met Gly Tyr Asn Asp Tyr Leu Ala Trp Phe Ala Tyr Trp
            100                 105                 110

Gly Gln Gly Thr Leu Val Thr Val Ser Ser
        115                 120

<210> SEQ ID NO 13
<211> LENGTH: 122
<212> TYPE: PRT
<213> ORGANISM: Artificial Sequence
<220> FEATURE:
<223> OTHER INFORMATION: Heavy chain variable

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val
        35                  40                  45

Ser Leu Ile Ser Gly Gly Gly Ser Tyr Ser Tyr Tyr Pro Asp Ser Leu
    50                  55                  60

Lys Gly Arg Phe Thr Ile Ser Arg Asp Ser Ala Lys Asn Ser Leu Tyr
65                  70                  75                  80

Leu Gln Met Ser Ser Leu Arg Ala Glu Asp Thr Ala Met Tyr Tyr Cys
                85                  90                  95

Ala Arg His Met Gly Tyr Asn Asp Tyr Leu Ala Trp Phe Ala Tyr Trp
            100                 105                 110

Gly Gln Gly Thr Leu Val Thr Val Ser Ser
        115                 120

<210> SEQ ID NO 14
<211> LENGTH: 122
<212> TYPE: PRT
<213> ORGANISM: Artificial Sequence
<220> FEATURE:
<223> OTHER INFORMATION: Heavy chain variable

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val
        35                  40                  45

Ser Leu Ile Ser Gly Gly Gly Ser Tyr Ser Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Met Gly Tyr Asn Asp Tyr Leu Ala Trp Phe Ala Tyr Trp
            100                 105                 110

Gly Gln Gly Thr Leu Val Thr Val Ser Ala
        115                 120

<210> SEQ ID NO 15
<211> LENGTH: 114
<212> TYPE: PRT
<213> ORGANISM: Artificial Sequence
```

<220> FEATURE:
<223> OTHER INFORMATION: light chain variable

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Pro Trp Thr Phe Gly Gly Gly Thr Lys Val Glu
            100                 105                 110

Ile Lys

<210> SEQ ID NO 16
<211> LENGTH: 114
<212> TYPE: PRT
<213> ORGANISM: Artificial Sequence
<220> FEATURE:
<223> OTHER INFORMATION: light chain variable

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Pro Trp Thr Phe Gly Gly Gly Thr Lys Val Glu
            100                 105                 110

Ile Lys

<210> SEQ ID NO 17
<211> LENGTH: 452
<212> TYPE: PRT
<213> ORGANISM: Artificial Sequence
<220> FEATURE:
<223> OTHER INFORMATION: variable heavy chain

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val
            35                  40                  45

```
Ser Leu Ile Ser Gly Gly Gly Ser Tyr Ser Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Met Gly Tyr Asn Asp Tyr Leu Ala Trp Phe Ala Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450
```

```
<210> SEQ ID NO 18
<211> LENGTH: 221
<212> TYPE: PRT
<213> ORGANISM: Artificial Sequence
<220> FEATURE:
<223> OTHER INFORMATION: variable light chain

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Pro Trp Thr Phe Gly Gly Gly Thr Lys Val Glu
            100                 105                 110

Ile Lys Arg Thr Val Ala Ala Pro Ser Val Phe Ile Phe Pro Pro Ser
            115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
            195                 200                 205

Ser Ser Pro Val Thr Lys Ser Phe Asn Arg Gly Glu Cys
    210                 215                 220

<210> SEQ ID NO 19
<211> LENGTH: 452
<212> TYPE: PRT
<213> ORGANISM: Artificial Sequence
<220> FEATURE:
<223> OTHER INFORMATION: Heavy chain

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Tyr
            20                  25                  30

Ala Met Ser Trp Val Arg Gln Ala Pro Gly Lys Gly Leu Glu Trp Val
            35                  40                  45

Ser Leu Ile Ser Gly Gly Gly Ser Tyr Ser Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg His Met Gly Tyr Asn Asp Tyr Leu Ala Trp Phe Ala Tyr Trp
            100             105             110

Gly Gln Gly Thr Leu Val Thr Val Ser Ser Ala Ser Thr Lys Gly Pro
            115             120             125

Ser Val Phe Pro Leu Ala Pro Ser Ser Lys Ser Thr Ser Gly Gly Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
                165             170             175

Ala Val Leu Gln Ser Ser Gly Leu Tyr Ser Leu Ser Ser Val Val Thr
            180             185             190

Val Pro Ser Ser Ser Leu Gly Thr Gln Thr Tyr Ile Cys Asn Val Asn
            195             200             205

His Lys Pro Ser Asn Thr Lys Val Asp Lys Arg Val Glu Pro Lys Ser
    210             215             220

Cys Asp Lys Thr His Thr Cys Pro Pro Cys Pro Ala Pro Glu Leu Leu
225             230             235             240

Gly Gly Pro Ser Val Phe Leu Phe Pro Pro Lys Pro Lys Asp Thr Leu
                245             250             255

Met Ile Ser Arg Thr Pro Glu Val Thr Cys Val Val Val Asp Val Ser
            260             265             270

His Glu Asp Pro Glu Val Lys Phe Asn Trp Tyr Val Asp Gly Val Glu
            275             280             285

Val His Asn Ala Lys Thr Lys Pro Arg Glu Glu Gln Tyr Ala Ser Thr
    290             295             300

Tyr Arg Val Val Ser Val Leu Thr Val Leu His Gln Asp Trp Leu Asn
305             310             315             320

Gly Lys Glu Tyr Lys Cys Lys Val Ser Asn Lys Ala Leu Pro Ala Pro
                325             330             335

Ile Glu Lys Thr Ile Ser Lys Ala Lys Gly Gln Pro Arg Glu Pro Gln
            340             345             350

Val Tyr Thr Leu Pro Pro Ser Arg Glu Glu Met Thr Lys Asn Gln Val
            355             360             365

Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
                405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
            435             440             445

Ser Pro Gly Lys
    450
```

<210> SEQ ID NO 20
<211> LENGTH: 221
<212> TYPE: PRT
<213> ORGANISM: Artificial Sequence
<220> FEATURE:
<223> OTHER INFORMATION: light chain

<400> SEQUENCE: 20

-continued

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Ala Asn Gln Lys Asn Tyr Leu Ala Trp Tyr Gln Gln Lys Pro Gly Gln
            35                  40                  45

Pro Pro Lys Leu Leu Ile Tyr Phe Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Pro Trp Thr Phe Gly Gly Gly Thr Lys Val Glu
            100                 105                 110

Ile Lys Arg Thr Val Ala Ala Pro Ser Val Phe Ile Phe Pro Pro Ser
            115                 120                 125

Asp Glu Gln Leu Lys Ser Gly Thr Ala Ser Val Val Cys Leu Leu Asn
        130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
            195                 200                 205

Ser Ser Pro Val Thr Lys Ser Phe Asn Arg Gly Glu Cys
    210                 215                 220

<210> SEQ ID NO 21
<211> LENGTH: 5
<212> TYPE: PRT
<213> ORGANISM: Artificial Sequence
<220> FEATURE:
<223> OTHER INFORMATION: Flexible spacer

<400> SEQUENCE: 21

Gly Gly Gly Gly Ser
1               5

<210> SEQ ID NO 22
<211> LENGTH: 44
<212> TYPE: DNA
<213> ORGANISM: Artificial Sequence
<220> FEATURE:
<223> OTHER INFORMATION: primer

<400> SEQUENCE: 22
cgtctcgtgg tggtggttct ggtggtggtg gttctgtgac aagg                    44

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23
ggtggtctcg agttatttgt acagttcgtc catgccg                            37
```

```
<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
ctaggaagct tatctatgga ttcatacctg ctg                                    33

<210> SEQ ID NO 25
<211> LENGTH: 57
<212> TYPE: DNA
<213> ORGANISM: Artificial Sequence
<220> FEATURE:
<223> OTHER INFORMATION: primer

<400> SEQUENCE: 25
accagaacca ccaccaccag aaccaccacc accgattgtt cttctactct tcctctg        57

<210> SEQ ID NO 26
<211> LENGTH: 30
<212> TYPE: PRT
<213> ORGANISM: Artificial Sequence
<220> FEATURE:
<223> OTHER INFORMATION: linker

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 27
<211> LENGTH: 16
<212> TYPE: PRT
<213> ORGANISM: Artificial Sequence
<220> FEATURE:
<223> OTHER INFORMATION: signal peptide

<400> SEQUENCE: 27

Met Pro Leu Leu Leu Leu Leu Pro Leu Leu Trp Ala Gly Ala Leu Ala
1               5                   10                  15

<210> SEQ ID NO 28
<211> LENGTH: 383
<212> TYPE: PRT
<213> ORGANISM: Artificial Sequence
<220> FEATURE:
<223> OTHER INFORMATION: hIL2 fusion protein (G4S)6

<400> SEQUENCE: 28

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80
```

```
Pro Arg Asp Leu Ile Ser Asn Ile Asn Val Ile Val Leu Glu Leu Lys
              85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr Gly Gly Gly Gly Ser Gly Gly Gly Ser Gly Gly
    130                 135                 140

Gly Gly Ser Gly Gly Gly Ser Gly Gly Gly Gly Ser Gly Gly Gly
145                 150                 155                 160

Gly Ser Asp Ile Val Met Thr Gln Ser Pro Asp Ser Leu Ala Val Ser
            165                 170                 175

Leu Gly Glu Arg Ala Thr Ile Asn Cys Lys Ser Ser Gln Ser Leu Leu
            180                 185                 190

Asn Ser Ala Asn Gln Lys Asn Tyr Leu Ala Trp Tyr Gln Gln Lys Pro
            195                 200                 205

Gly Gln Pro Pro Lys Leu Leu Ile Tyr Phe Ala Ser Thr Arg Glu Ser
    210                 215                 220

Gly Val Pro Asp Arg Phe Ser Gly Ser Gly Ser Gly Thr Asp Phe Thr
225                 230                 235                 240

Leu Thr Ile Ser Ser Leu Gln Ala Glu Asp Val Ala Val Tyr Tyr Cys
            245                 250                 255

Gln Gln Tyr Tyr Ser Ala Pro Pro Trp Thr Phe Gly Gly Gly Thr Lys
            260                 265                 270

Val Glu Ile Lys Arg Thr Val Ala Ala Pro Ser Val Phe Ile Phe Pro
            275                 280                 285

Pro Ser Asp Glu Gln Leu Lys Ser Gly Thr Ala Ser Val Val Cys Leu
    290                 295                 300

Leu Asn Asn Phe Tyr Pro Arg Glu Ala Lys Val Gln Trp Lys Val Asp
305                 310                 315                 320

Asn Ala Leu Gln Ser Gly Asn Ser Gln Glu Ser Val Thr Glu Gln Asp
            325                 330                 335

Ser Lys Asp Ser Thr Tyr Ser Leu Ser Ser Thr Leu Thr Leu Ser Lys
            340                 345                 350

Ala Asp Tyr Glu Lys His Lys Val Tyr Ala Cys Glu Val Thr His Gln
            355                 360                 365

Gly Leu Ser Ser Pro Val Thr Lys Ser Phe Asn Arg Gly Glu Cys
    370                 375                 380
```